(12) United States Patent
Black et al.

(10) Patent No.: US 9,138,494 B2
(45) Date of Patent: Sep. 22, 2015

(54) RADIOLABELED PDE10A LIGANDS

(71) Applicant: AbbVie Inc., North Chicago, IL (US)

(72) Inventors: Lawrence A. Black, Libertyville, IL (US); Berthold Behl, Wiesbaden (DE); Jill Wetter, North Chicago, IL (US)

(73) Assignees: AbbVie Inc., North Chicago, IL (US); AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 13/723,406

(22) Filed: Dec. 21, 2012

(65) Prior Publication Data
US 2013/0343992 A1    Dec. 26, 2013

Related U.S. Application Data

(60) Provisional application No. 61/579,799, filed on Dec. 23, 2011.

(51) Int. Cl.
| | |
|---|---|
| *A61K 51/00* | (2006.01) |
| *A61M 36/14* | (2006.01) |
| *A61K 51/04* | (2006.01) |
| *C07D 471/04* | (2006.01) |
| *C07D 413/14* | (2006.01) |
| *C07D 401/14* | (2006.01) |
| *C07D 417/14* | (2006.01) |
| *C07B 59/00* | (2006.01) |

(52) U.S. Cl.
CPC ......... *A61K 51/0455* (2013.01); *A61K 51/0459* (2013.01); *A61K 51/0465* (2013.01); *C07B 59/002* (2013.01); *C07D 401/14* (2013.01); *C07D 413/14* (2013.01); *C07D 417/14* (2013.01); *C07D 471/04* (2013.01)

(58) Field of Classification Search
None
See application file for complete search history.

(56) References Cited

U.S. PATENT DOCUMENTS

2006/0154931 A1*  7/2006  Verhoest et al. ............. 514/249
2007/0155779 A1*  7/2007  Verhoest et al. ............. 514/303

FOREIGN PATENT DOCUMENTS

| WO | 03/093499 | 11/2003 |
| WO | 2005/002579 | 1/2005 |
| WO | WO 2010097367 A1 * | 9/2010 |
| WO | WO 2011150156 A2 * | 12/2011 |

OTHER PUBLICATIONS

Ishiwata et al. App. Rad. Isotop. 50 (1999) 693-697.*
Patani et al. Chem. Rev. 1996, 96, 3147-3176.*
Zhang et al. Curr. Top. Med. Chem. 2007, 7, 1817-1828.*
Turan-Zitouni et al. Eur. J. Med. Chem. 39 (2003) 267-272.*
Tu et al. Bioorg. Med. Chem. 19 (2011) 1666-1673.*
Burns, H.D., "PET ligands for assessing receptor occupancy in vivo," Ann. Reports in Medicinal Chem. (2001) 36:267-276.
Burns, H.D., "Positron emission tomography neuroreceptor imaging as a tool in drug discovery, research and development," Curr. Opin. Chem. Biol. (1999) 3(4):388-394.
Fujishige, K. et al., "Striatum- and testis-specific phosphodiesterase PDE10A. Isolation and characterization of a rat PDE10A," Eur. J. Biochem. (1999) 266:1118-1127.
Hietala, J., "Ligand-receptor interactions as studied by PET implications for drug development," Annals of med. (1999) 31(6):438-443.
Higuchi, T. et al., editors, Pro-drugs as Novel Drug Delivery Systems, vol. 14 of the ACS Symposium Series; American Chemical Socity, Washington, D.C., (1975) Table of Contents.
IUPAC, International Union of Pure and Applied Chemistry, Rules for the Nomenclature of Organic Chemistry, Section E: stereochemistry, Pergamon Press, Oxford, Pure & Applied Chem. (1976) 45:11-30.
Kehler, J. et al., "PDE10A inhibitors: novel therapeutic drugs for schizophrenia," Curr. Pharm. Design (2011) 17:137-150.
Kotera, J. et al., "Characterization and phosphorylation of PDE10A2, a novel alternative splice variant of human phosphodiesterase that hydrolyzes cAMP and cGMP," Biochem. Biophys. Res. Comm. (1999) 261:551-557.
Loughney, K. et al., "Isolation and characterization of PDE10A, a novel human 3', 5'-cyclic nucleotide phosphodiesterase," Gene (1999) 234:109-117.

(Continued)

Primary Examiner — Michael G Hartley
Assistant Examiner — Sean R Donohue
(74) Attorney, Agent, or Firm — Lisa V. Mueller; Michael Best & Friedrich LLP

(57) ABSTRACT

Compounds of formula (I) are disclosed

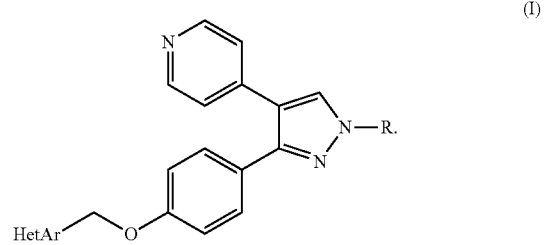

Compounds of formula (I) are useful in treating conditions and disorders prevented by or ameliorated by PDE10A ligands. Radiolabeled compounds of formula (I) are also useful as diagnostic tools as PDE10A positron emission tomography ligands. Also disclosed are pharmaceutical compositions comprising compound of formula (I), methods for using such compounds and compositions, and a process for preparing compounds within the scope of formula (I).

17 Claims, No Drawings

(56) References Cited

OTHER PUBLICATIONS

Roche, E.B., editor, Bioreversible Carriers in Drug Design, American Pharmaceutical Association and Pergamon Press (1987).

Rodefer, J.S. et al., "PDE10A inhibition reverses subchronic PCP-induced deficits in attentional set-shifting in rats," Eur. J. Neurosci. (2005) 21:1070-1076.

Schmidt, C.J. et al., "Preclinical characterization of selective phosphodiesterase 10a inhibitors: a new therapeutic approach to the treatment of schizophrenia," J. Pharm. Exp. Thera. (2008) 325(2):681-690.

Seeger, T.F. et al., "Immunohistochemical localization of PDE10A in the rat brain," Brain Res. (2003) 985:113-126.

Siuciak, J.A. et al., "Inhibition of the striatum-enriched phosphodiesterase PDE10A: a novel aproach to the treatment of psychosis," Neuropharm. (2006) 51:386-396.

Soderling, S.H. et al., "Isolation and characterization of a dual-substrate phosphodiesterase gene family: PDE10A," Proc. Natl. Acad. Sci. USA (1999) 96:7071-7076.

* cited by examiner

RADIOLABELED PDE10A LIGANDS

CROSS-REFERENCE TO RELATED APPLICATION

This claims priority to U.S. Provisional Patent Application No. 61/579,799, filed on Dec. 23, 2011, the contents of which are herein fully incorporated by reference.

TECHNICAL FIELD

The invention relates to pyrazole derivatives, and more particularly, to radiolabeled pyrazole derivatives, compositions comprising such compounds, methods of using such compounds and compositions, and processes for preparing such compounds.

BACKGROUND

Cyclic-adenosine monophosphate (cAMP) and cyclic-guanosine monophosphate (cGMP) are second messengers that regulate a vast array of cellular responses, particularly within the central nervous system. These cyclic nucleotides mediate biological response to extracellular signals (e.g., hormones, light, neurotransmitters) and influence processes such as ion channel function, muscle contraction, learning, differentiation, apoptosis, lipogenesis, glycogenolysis, gluconeogenesis, and proinflammatory mediator production and action (Kehler, J., Nielsen, J., Curr. Pharm. Des. 2011, 17, 137-150).

Phosphodiesterases (PDEs) are a family of enzymes that render cAMP and cGMP inactive through hydrolysis of the cyclic nucleotide 3',5'-phosphodiester bond, and thus play a crucial role in controlling intracellular levels of cAMP/cGMP. Phosphodieasterase-10A (PDE10A), a dual-specificity phosphodiesterase, can convert both cAMP to AMP and cGMP to GMP (Loughney, K. et al. Gene 1999, 234, 109-117; Fujishige, K. et al. Eur. J. Biochem. 1999, 266, 1118-1127 and Soderling, S. et al. Proc. Natl. Acad. Sci. 1999, 96, 7071-7076). PDE10A is primarily expressed in the brain in the medium spiny neurons of the striatum, nucleus accumbens, and olfactory tubercle (Kotera, J. et al. Biochem. Biophys. Res. Comm. 1999, 261, 551-557 and Seeger, T. F. et al. Brain Research, 2003, 985, 113-126). These constitute the core of the basal ganglia system, which is involved in the regulation of motor, appetitive, and cognitive processes.

The activity of PDE10A can be modified or regulated by the administration of PDE10A inhibitors. PDE10A inhibitors have therapeutic potential for the treatment for disorders and conditions mediated in part by dysfunction of the basal ganglia, other parts of the central nervous system and other PDE10A expressing tissues. Such disorders and conditions include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. PDE10A inhibitors are also suitable for the treatment of diabetes and related disorders such as obesity by regulating the cAMP signaling system. PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, Alzheimer's disease, Huntington's disease, Parkinson's disease, multiple sclerosis, stroke and spinal cord injury. The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

Although various classes of compounds demonstrating PDE10A inhibitory activity exist, it would be beneficial to provide additional compounds demonstrating PDE10A modulation that can be incorporated into pharmaceutical compositions useful for therapeutic methods. A useful tool for assessing the ability of a compound to modulate a particular receptor in humans and animals is positron emission tomography (PET). Positron emission tomography includes the use of positron or gamma emitting radiolabeled compounds to study the interaction between an unlabeled compound and the radiolabeled compound for binding to the receptor of interest. This information is valuable for clinical candidate selection, determination of first-in-human dosing levels, proof of concept studies, and assessment of probability of success of a drug candidate relative to its therapeutic index. The topic and use of positron-emitting ligands for this purpose has been generally reviewed, for example in "PET ligands for assessing receptor occupancy in vivo" Burns, et al Annual Reports in Medicinal Chemistry (2001), 36, 267-276; "Ligand-receptor interactions as studied by PET: implications for drug development" by Jarmo Hietala, Annals of Medicine (Helsinki) (1999), 31(6), 438-443; "Positron emission tomography neuroreceptor imaging as a tool in drug discovery, research and development" Burns, et al. Current Opinion in Chemical Biology (1999), 3(4), 388-394.

Although compounds potentially useful as PDEA10 PET ligands are known, in general, these tracers suffer from high lipophilicity that can lead to poor specific/nonspecific binding ratios. Furthermore, the kinetics of these tracers and existence of significant quantities of brain-penetrant labeled metabolites may hinder their effectiveness for quantitatively evaluating enzyme occupancy in humans. Accordingly, it would be beneficial to provide additional compounds useful for noninvasive imaging of PDE10A receptor occupancy in humans and animals. In particular, it would be beneficial to provide PDEA10A PET ligands having optimal lipophilicity, protein binding, permeability glycoprotein (P-gp) interaction, free brain concentrations, specific/nonspecific binding ratios, and human hepatocyte metabolic stability.

SUMMARY

This invention is directed to pyrazole derivatives, and more particularly, to radiolabeled pyrazole derivatives, compositions comprising such compounds, methods of using such compounds and compositions, and processes for preparing such compounds.

In one aspect, the invention relates to pyrazole derivatives having a compound of formula (I):

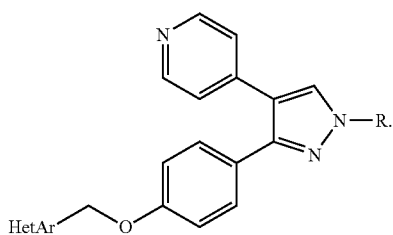

or a pharmaceutically acceptable salt, ester, amide, prodrug, or radiolabeled form thereof, wherein R is selected from the group consisting of hydrogen, $C_1$-$C_6$ alkyl, and $C_3$-$C_8$ cycloalkyl;

HetAr is a heteroaryl group selected from the group consisting of formula (i) and formula (ii);

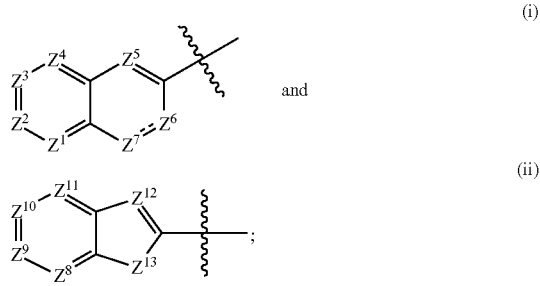

- - - is absent or a bond;

$Z^1, Z^2, Z^3, Z^4, Z^5, Z^8, Z^9, Z^{10}, Z^{11}$, and $Z^{12}$ are each independently selected from the group consisting of N and $CR^2$;

$Z^6$ and $Z^7$ are each independently selected from the group consisting of N, $NR^1$, $CR^2$, $CHR^3$, $SO_2$, and C=O;

$Z^{13}$ is selected from the group consisting of $NR^1$, $CHR^3$, and O; and $R^1$, $R^2$, and $R^3$ are each independently selected from the group consisting of hydrogen, halogen, $C_1$-$C_6$ alkyl, and $C_3$-$C_8$ cycloalkyl;

provided that at least two of $Z^1, Z^2, Z^3, Z^4, Z^5, Z^6$, and $Z^7$ are heteroatoms; and provided that the following non-radiolabeled compounds are excluded:

2-((4-(1-methyl-4-(pyridin-4-yl)-1H-pyrazol-3-yl)phenoxy)methyl)quinazoline; and 1-methyl-2-((4-(1-methyl-4-(pyridin-4-yl)-1H-pyrazol-3-yl)phenoxy)methyl)-1H-benzo[d]imidazole.

Another aspect of the invention relates to pharmaceutical compositions comprising compounds of the invention. Such compositions can be administered in accordance with a method of the invention as part of a therapeutic regimen for treatment or prevention of conditions and disorders related to PDE10A activity. Such compositions can be administered in a diagnostic procedure, such as positron emission tomography (PET) or single photon emission computed tomography (sPECT).

Another aspect of the invention relates to use of the compounds and compositions of the invention as diagnostic tools. The compounds of the invention, synthesized with $^{11}C$, $^{18}F$, or other positron-emitting isotopes are suitable ligand tools for PET. Especially suitable compounds of the invention for this use are those wherein a $^{11}CH_3$ group can be incorporated into the compound by reaction with $^{11}CH_3I$. Also, especially suitable compounds of the use are those wherein a $^{18}F$ group can be incorporated into the compound by reaction with $^{18}F$-fluoride anion. The incorporation of $^{11}CH_3$ can be carried out according to a method known to those skilled in the art. According to one method, compounds of formula (I) can be treated with base and an alkyl iodide such as $^{11}CH_3I$ to prepare ligands for use in PET studies. For incorporation of $^{18}F$ into compounds or compositions of the invention, compounds of formula (I) can be treated with methanesulfonic anhydride or triflic anhydride and a base in an inert solvent such as dichloromethane, and the resulting compound (a methanesulfonate or triflate) can be treated with $^{18}F$-fluoride by methods well known to skilled in the art of synthetic organic chemistry or medicinal chemistry.

Yet another aspect of the invention relates to a method of selectively modulating PDE10A activity. The method is useful for treating, or preventing conditions and disorders related to PDE10A modulation in mammals. More particularly, the method is useful for treating or preventing conditions and disorders related to central nervous system function, including memory, cognition processes and neurological processes.

Processes for making compounds of the invention also are contemplated.

The compounds, compositions comprising the compounds, methods for making the compounds, methods for treating or preventing conditions and disorders by administering the compounds, radiolabeled forms of the compounds, compositions containing radiolabeled forms of the compounds, and methods of using radiolabeled forms of the compounds are further described herein.

DETAILED DESCRIPTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. Each of the carbon atoms of the alkyl group is substituted with hydrogen or with 0, 1, or 2 substituents selected from acyl, acyloxy, alkoxy, alkoxyalkoxy, alkoxyalkyl, alkoxycarbonyl, alkoxyimino, alkoxysulfonyl, alkylcarbonyl, alkylsulfonyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, $NR_AR_B$, $(NR_AR_B)$carbonyl, $(NR_AR_B)$sulfonyl, —OS(O)$_2$-alkyl, and —OS(O)$_2$-aryl.

The term "alkylene" means a divalent group derived from a straight or branched chain hydrocarbon of from 1 to 10 carbon atoms. Representative examples of alkylene include, but are not limited to, —CH$_2$—, —CH(CH)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH)CH$_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —NH$_2$ group.

The term "aryl," as used herein, means phenyl, a bicyclic aryl, or a tricyclic aryl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is a tricyclic aryl ring system such as anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, anthracenyl, phenanthrenyl, azulenyl, dihydroanthracenyl, fluorenyl, and tetrahydrophenanthrenyl.

The carbon atoms of the aryl groups of this invention are substituted with hydrogen or are optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_AR_B$, $(NR_AR_B)$carbonyl, —SO$_2$N($R_{14a}$)($R_{14b}$), and N($R_{14a}$)SO$_2$($R_{14b}$). Where the aryl group is a phenyl group, the number of substituents is 0, 1, 2, 3, 4, or 5. Where the aryl group is a bicyclic aryl, the number of substituents is 0, 1, 2, 3, 4, 5, 6, 7, 8, or 9. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —CO$_2$H group, which may be protected as an ester group —CO$_2$-alkyl.

The term "cyano" as used herein means a —CN group, attached to the parent molecular moiety through the carbon.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

Each of the carbon atoms of the cycloalkyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —NR$_A$R$_B$, (NR$_A$R$_B$)carbonyl, —SO$_2$N(R$_{14a}$)(R$_{14b}$), and N(R$_{14a}$)SO$_2$(R$_{14b}$).

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, as defined herein, appended to the parent molecular moiety through an alkyl group, as defined herein. Representative examples of fluoroalkyl include, but are not limited to, fluoromethyl, difluoromethyl, trifluoromethyl, pentafluoroethyl, 2-fluoroethyl, and 2,2,2-trifluoroethyl.

The term "fluoroalkoxy" as used herein means at least one fluoro group, as defined herein, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, heptafluoropropyloxy, and 2,2,2-trifluoroethoxy.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle", as used herein, refers to aromatic or non-aromatic cyclic groups that contain at least one heteroatom. Examples of aromatic heterocycles are, for example, heteroaryl groups as further defined below. Non-aromatic heterocycles are non-aromatic cyclic groups that contain at least one heteroatom; examples of non-aromatic heterocyclic groups or non-aromatic heterocycles are further defined below. Heterocyclic rings are connected to the parent molecular moiety through a carbon atom, or alternatively in the case of heterocyclic rings that contain a bivalent nitrogen atom having a free site for attachment, the heterocyclic ring may be connected to the parent molecular moiety though a nitrogen atom. Additionally, the heterocycles may be present as tautomers.

The term "heteroaryl", as used herein, refers to an aromatic ring containing one or more heteroatoms independently selected from nitrogen, oxygen, or sulfur, or a tautomer thereof. Such rings can be monocyclic or bicyclic as further described herein.

The terms "monocyclic heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or S atom; one, two, or three N atoms are arranged in a suitable manner to provide an aromatic ring; or a ring wherein two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five-membered rings containing one to four nitrogen atoms; and five-membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring containing at least 3 double bonds, and wherein the atoms of the ring include one or more heteroatoms independently selected from oxygen, sulfur, and nitrogen. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, may be substituted with hydrogen, or optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —NR$_A$R$_B$, (NR$_A$R$_B$)carbonyl, —SO$_2$N(R$_{14a}$)(R$_{14b}$), and N(R$_{14a}$)SO$_2$(R$_{14b}$). Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the present invention may be present as tautomers.

The terms "non-aromatic heterocyclic ring" and "non-aromatic heterocycle", as used herein, refer to a 4- to 12-membered monocyclic or bicyclic ring containing at least one saturated carbon atom, and also containing one, two, three, four, or five heteroatoms independently selected from the group consisting of nitrogen, oxygen, and sulfur. Four- and five-membered rings may have zero or one double bond. Six-membered rings may have zero, one, or two double bonds. Seven- and eight-membered rings may have zero, one, two, or three double bonds. The non-aromatic heterocycle groups of the invention can be attached through a carbon atom or a nitrogen atom. The non-aromatic heterocycle groups may be present in tautomeric form. Representative examples of nitrogen-containing heterocycles include, but are not limited to, azepanyl, azetidinyl, aziridinyl, azocanyl, morpholinyl, piperazinyl, piperidinyl, pyrrolidinyl, pyrrolinyl, dihydrothiazolyl, dihydropyridinyl, and thiomorpholinyl. Representative examples of non-nitrogen containing non-aromatic heterocycles include, but are not limited to, dioxanyl, dithianyl, tetrahydrofuryl, dihydropyranyl, tetrahydropyranyl, and [1,3]dioxolanyl.

The non-aromatic heterocycles of the invention may be substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —$NR_AR_B$, $(NR_AR_B)$carbonyl, —$SO_2N(R_{14a})(R_{14b})$, and $N(R_{14a})SO_2(R_{14b})$.

Additional examples of heterocycles include, but are not limited to, isoindoline-1,3-dione, (Z)-1H-benzo[e][1,4]diazepin-5(4H)-one, pyrimidine-2,4(1H,3H)-dione, benzo[d]thiazol-2(3H)-one, pyridin-4(1H)-one, imidazolidin-2-one, 1H-imidazol-2(3H)-one, pyridazin-3(2H)-one, tetrahydropyrimidin-2(1H)-one, and 1H-benzo[d]imidazol-2(3H)-one.

The term "heterocyclealkyl" as used herein means a heterocycle group, as defined herein, appended to the parent molecular moiety through an alkyl group, as defined herein. Representative examples of heterocyclealkyl include, but are not limited to, 2-thienylmethyl, 2-thienylethyl, 2-furylethyl, and 2-furylmethyl.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "$(NR_AR_B)$" as used herein means an amino group substituted by $R_A$ and $R_B$. $R_A$ and $R_B$ are independently selected from hydrogen, alkyl, acyl, cycloalkyl, and formyl.

The term "$(NR_AR_B)$alkyl" as used herein means an —$NR_AR_B$ group, as defined herein, appended to the parent molecular moiety through an alkyl group, as defined herein. Representative examples of $(NR_AR_B)$alkyl include, but are not limited to, 2-(methylamino)ethyl, 2-(dimethylamino)ethyl, 2-(amino)ethyl, 2-(ethylmethylamino)ethyl, and the like.

The term "$(NR_AR_B)$carbonyl" as used herein means an —$NR_AR_B$ group, as defined herein, appended to the parent molecular moiety through a carbonyl group, as defined herein. Representative examples of $(NR_AR_B)$carbonyl include, but are not limited to, aminocarbonyl, (methylamino)carbonyl, (dimethylamino)carbonyl, (ethylmethylamino)carbonyl, and the like.

The term "$(NR_AR_B)$sulfonyl" as used herein means a —$NR_AR_B$ group, as defined herein, appended to the parent molecular moiety through a sulfonyl group, as defined herein. Representative examples of $(NR_AR_B)$sulfonyl include, but are not limited to, aminosulfonyl, (methylamino)sulfonyl, (dimethylamino)sulfonyl and (ethylmethylamino)sulfonyl.

The term "—$N(R_{14a})SO_2(R_{14b})$" as used herein means an amino group attached to the parent moiety to which is further appended with an $R_{14a}$ group as defined herein, and a $SO_2$ group to which is appended an $(R_{14b})$ group as defined herein. $R_{14a}$ and $R_{14b}$ are each independently hydrogen, alkyl, or cycloalkyl. Representative examples of —$N(R_{14a})SO_2(R_{14b})$ include, but are not limited to, N-methylmethanesulfonamide.

The term "—$SO_2N(R_{14a})(R_{14b})$" as used herein means a $N(R_{14a})(R_{14b})$ group attached to a $SO_2$ group, appended to the parent moiety through the sulfonyl group. $R_{14a}$ and $R_{14b}$ are each independently hydrogen, alkyl, or cycloalkyl. Representative examples of $SO_2N(R_{14a})(R_{14b})$ include, but are not limited to (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —$S(O)_2$— group.

The term "radiolabel" as used herein refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3H$ (tritium), $^{14}C$, $^{11}C$, $^{15}O$, $^{18}F$, $^{35}S$, $^{123}I$, and $^{125}I$.

Compounds of the Invention

Compounds of formula (I) are disclosed,

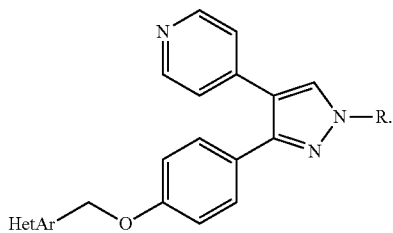

(I)

wherein HetAr and R are as described in the Summary of the Invention.

In certain embodiments, the compounds of formula (I) are radiolabeled.

In certain embodiments, R comprises a radiolabeled substituent group. Preferably, R comprises a [$^{11}$C]-radiolabeled or a [$^{18}$F]-radiolabeled substituent group. More preferably, R is selected from [$^{11}$C]methyl and 2-[$^{18}$F]fluoroethyl.

In certain embodiments, HetAr comprises a radiolabeled substituent group. Preferably, HetAr comprises a [$^{11}$C]-radiolabeled or a [$^{18}$F]-radiolabeled substituent group. More preferably, HetAr comprises a radiolabeled group selected from [$^{11}$C]methyl and 2-[$^{18}$F]fluoroethyl.

In certain embodiments, HetAr is a heteroaryl group selected from the group consisting of

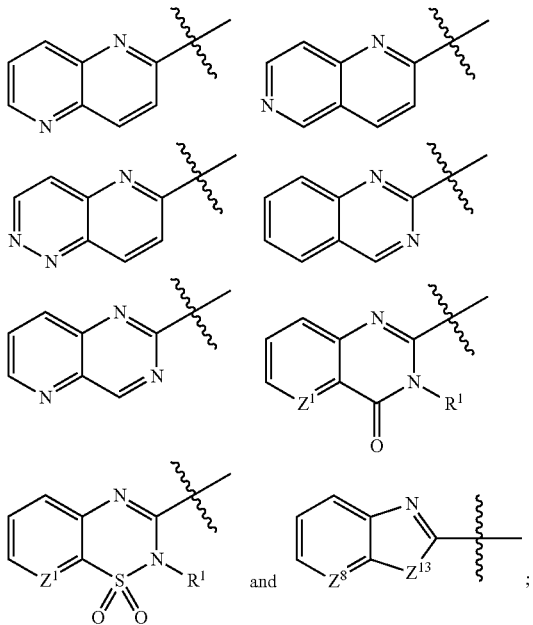

wherein $Z^1$, $Z^8$, $Z^{13}$, and $R^1$ are as defined in the Summary of the Invention.

In certain embodiments, HetAr is a heteroaryl group of formula (a),

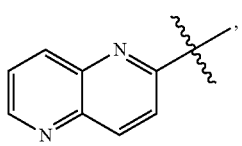

(a)

wherein R is selected from the group consisting of hydrogen, $C_1$-$C_6$ alkyl, and $C_3$-$C_8$ cycloalkyl. Preferably, R is $C_1$-$C_6$ alkyl. More preferably, R is methyl or 2-fluoroethyl. Most preferably, R is [$^{11}$C]methyl or 2-[$^{18}$F]fluoroethyl.

In certain embodiments, HetAr is a heteroaryl group of formula (b),

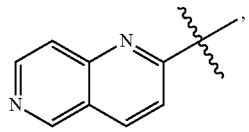

(b)

wherein R is selected from the group consisting of hydrogen, $C_1$-$C_6$ alkyl, and $C_3$-$C_8$ cycloalkyl. Preferably, R is $C_1$-$C_6$ alkyl. More preferably, R is methyl or 2-fluoroethyl. Most preferably, R is [$^{11}$C]methyl or 2-[$^{18}$F]fluoroethyl.

In certain embodiments, HetAr is a heteroaryl group of formula (c), (c)

wherein R is selected from the group consisting of hydrogen, $C_1$-$C_6$ alkyl, and $C_3$-$C_8$ cycloalkyl. Preferably, R is $C_1$-$C_6$ alkyl. More preferably, R is methyl or 2-fluoroethyl. Most preferably, R is [$^{11}$C]methyl or 2-[$^{18}$F]fluoroethyl.

In certain embodiments, HetAr is a heteroaryl group of formula (d), (d)

wherein R is selected from the group consisting of hydrogen, $C_1$-$C_6$ alkyl, and $C_3$-$C_8$ cycloalkyl. Preferably, R is $C_1$-$C_6$ alkyl. More preferably, R is methyl or 2-fluoroethyl. Most preferably, R is [$^{11}$C]methyl or 2-[$^{18}$F]fluoroethyl.

In certain embodiments, HetAr is a heteroaryl group of formula (e),

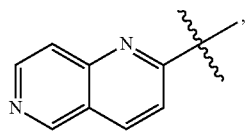

(e)

wherein R is selected from the group consisting of hydrogen, $C_1$-$C_6$ alkyl, and $C_3$-$C_8$ cycloalkyl. Preferably, R is $C_1$-$C_6$ alkyl. More preferably, R is methyl or 2-fluoroethyl. Most preferably, R is [$^{11}$C]methyl or 2-[$^{18}$F]fluoroethyl.

In certain embodiments, HetAr is a heteroaryl group of formula (f),

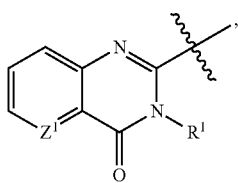

(f)

wherein R is selected from the group consisting of hydrogen, $C_1$-$C_6$ alkyl, and $C_3$-$C_8$ cycloalkyl; $Z^1$ is N or CH; and $R^1$ is selected from the group consisting of hydrogen, $C_1$-$C_6$ alkyl, and $C_3$-$C_8$ cycloalkyl. Preferably, R is $C_1$-$C_6$ alkyl and $R^1$ is $C_1$-$C_6$ alkyl. More preferably, at least one of R and $R^1$ is methyl or 2-fluoroethyl. Most preferably, one of R and $R^1$ is [$^{11}$C]methyl or 2-[$^{18}$F]fluoroethyl.

In certain embodiments, HetAr is a heteroaryl group of formula (g),

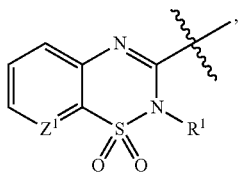

(g)

wherein R is selected from the group consisting of hydrogen, $C_1$-$C_6$ alkyl, and $C_3$-$C_8$ cycloalkyl; $Z^1$ is N or CH; and $R^1$ is selected from the group consisting of hydrogen, $C_1$-$C_6$ alkyl, and $C_3$-$C_8$ cycloalkyl. Preferably, R is $C_1$-$C_6$ alkyl and $R^1$ is $C_1$-$C_6$ alkyl. More preferably, at least one of R and $R^1$ is methyl or 2-fluoroethyl. Most preferably, one of R and $R^1$ is [$^{11}$C]methyl or 2-[$^{18}$F]fluoroethyl.

In certain embodiments, HetAr is a heteroaryl group of formula (h),

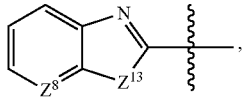

(h)

wherein R is selected from the group consisting of hydrogen, $C_1$-$C_6$ alkyl, and $C_3$-$C_8$ cycloalkyl; $Z^8$ is N or CH; $Z^{13}$ is $NR^1$, $CHR^3$, or O; $R^1$ is selected from the group consisting of hydrogen, $C_1$-$C_6$ alkyl, and $C_3$-$C_8$ cycloalkyl; and $R^3$ is selected from the group consisting of hydrogen, $C_1$-$C_6$ alkyl, and $C_3$-$C_8$ cycloalkyl. Preferably, when $Z^{13}$ is O, R is $C_1$-$C_6$ alkyl, more preferably R is methyl or 2-fluoroethyl, and most preferably R is [$^{11}$C]methyl or 2-[$^{18}$F]-fluoroethyl. Preferably, when $Z^{13}$ is $NR^1$, R is $C_1$-$C_6$ alkyl and $R^1$ is $C_1$-$C_6$ alkyl, more preferably at least one of R and $R^1$ is methyl or 2-fluoroethyl, and most preferably one of R and $R^1$ is [$^{11}$C]methyl or 2-[$^{18}$F]fluoroethyl. Preferably, when $Z^{13}$ is $CHR^3$, R is $C_1$-$C_6$ alkyl and $R^3$ is $C_1$-$C_6$ alkyl, more preferably at least one of R and $R^3$ is methyl or 2-fluoroethyl, and most preferably one of R and $R^3$ is [$^{11}$C]methyl or 2-[$^{18}$F]fluoroethyl.

Specific embodiments contemplated as part of the invention also include, but are not limited to, compounds of formula (I), as defined, for example:
2-((4-(1-methyl-4-(pyridin-4-yl)-1H-pyrazol-3-yl)phenoxy)methyl)-1,5-naphthyridine;
2-((4-(1-(2-fluoroethyl)-4-pyridin-4-yl)-1H-pyrazol-3-yl)phenoxy)methyl)-1,5-naphthyridine;
2-((4-(1-methyl-4-(pyridin-4-yl)-1H-pyrazol-3-yl)phenoxy)methyl)-1,6-naphthyridine;
2-((4-(1-(2-fluoroethyl)-4-pyridin-4-yl)-1H-pyrazol-3-yl)phenoxy)methyl)-1,6-naphthyridine;
6-((4-(1-methyl-4-(pyridin-4-yl)-1H-pyrazol-3-yl)phenoxy)methyl)pyrido[3,2-c]pyridazine;
6-((4-(1-(2-fluoroethyl)-4-(pyridin-4-yl)-1H-pyrazol-3-yl)phenoxy)methyl)pyrido[3,2-c]pyridazine;
2-((4-(1-(2-fluoroethyl)-4-(pyridin-4-yl)-1H-pyrazol-3-yl)phenoxy)methyl)quinazoline;
2-((4-(1-methyl-4-(pyridin-4-yl)-1H-pyrazol-3-yl)phenoxy)methyl)pyrido[3,2-d]pyrimidine;
2-((4-(1-(2-fluoroethyl)-4-(pyridin-4-yl)-1H-pyrazol-3-yl)phenoxy)methyl)pyrido[3,2-d]pyrimidine;
3-methyl-2-((4-(1-methyl-4-(pyridin-4-yl)-1H-pyrazol-3-yl)phenoxy)methyl)quinazolin-4(3H)-one;
2-((4-(1-(2-fluoroethyl)-4-(pyridin-4-yl)-1H-pyrazol-3-yl)phenoxy)methyl)-3-methylquinazolin-4(3H)-one;
3-(2-fluoroethyl)-2-((4-(1-methyl-4-(pyridin-4-yl)-1H-pyrazol-3-yl)phenoxy)methyl)quinazolin-4(3H)-one;
3-methyl-2-((4-(1-methyl-4-(pyridin-4-yl)-1H-pyrazol-3-yl)phenoxy)methyl)pyrido[3,2-d]pyrimidin-4(3H)-one;
2-((4-(1-(2-fluoroethyl)-4-(pyridin-4-yl)-1H-pyrazol-3-yl)phenoxy)methyl)-3-methylpyrido[3,2-d]pyrimidin-4(3H)-one;
3-(2-fluoroethyl)-2-((4-(1-methyl-4-(pyridin-4-yl)-1H-pyrazol-3-yl)phenoxy)methyl)pyrido[3,2-d]pyrimidin-4(3H)-one;
1,1-dioxo-2-methyl-3-((4-(1-methyl-4-(pyridin-4-yl)-1H-pyrazol-3-yl)phenoxy)methyl)-2H-benzo[e][1,2,4]thiadiazine;
1,1-dioxo-2-methyl-3-((4-(1-(2-fluoroethyl)-4-(pyridin-4-yl)-1H-pyrazol-3-yl)phenoxy)methyl)-2H-benzo[e][1,2,4]thiadiazine;
1,1-dioxo-2-(2-fluoroethyl)-3-((4-(1-methyl-4-(pyridin-4-yl)-1H-pyrazol-3-yl)phenoxy)methyl)-2H-benzo[e][1,2,4]thiadiazine;
2-((4-(1-methyl-4-(pyridin-4-yl)-1H-pyrazol-3-yl)phenoxy)methyl)benzo[d]oxazole;
2-((4-(1-(2-fluoroethyl)-4-(pyridin-4-yl)-1H-pyrazol-3-yl)phenoxy)methyl)benzo[d]oxazole;
2-((4-(1-(2-fluoroethyl)-4-(pyridin-4-yl)-1H-pyrazol-3-yl)phenoxy)methyl)-1-methyl-1H-benzo[d]imidazole;
1-(2-fluoroethyl)-2-((4-(1-methyl-4-(pyridin-4-yl)-1H-pyrazol-3-yl)phenoxy)methyl)-1H-benzo[d]imidazole;
2-((4-(1-methyl-4-(pyridin-4-yl)-1H-pyrazol-3-yl)phenoxy)methyl)oxazolo[5,4-b]pyridine;
2-((4-(1-(2-fluoroethyl)-4-(pyridin-4-yl)-1H-pyrazol-3-yl)phenoxy)methyl)oxazolo[5,4-b]pyridine;
3-methyl-2-((4-(1-methyl-4-(pyridin-4-yl)-1H-pyrazol-3-yl)phenoxy)methyl)-3H-imidazo[4,5-b]pyridine;
2-((4-(1-(2-fluoroethyl)-4-(pyridin-4-yl)-1H-pyrazol-3-yl)phenoxy)methyl)-3-methyl-3H-imidazo[4,5-b]pyridine;
3-(2-fluoroethyl)-2-((4-(1-methyl-4-(pyridin-4-yl)-1H-pyrazol-3-yl)phenoxy)methyl)-3H-imidazo[4,5-b]pyridine;
2-((4-(1-[$^{11}$C]methyl-4-(pyridin-4-yl)-1H-pyrazol-3-yl)phenoxy)methyl)-1,5-naphthyridine;
2-((4-(1-(2-[$^{18}$F]fluoroethyl)-4-pyridin-4-yl)-1H-pyrazol-3-yl)phenoxy)methyl)-1,5-naphthyridine;
2-((4-(1-[$^{11}$C]methyl-4-(pyridin-4-yl)-1H-pyrazol-3-yl)phenoxy)methyl)-1,6-naphthyridine;
2-((4-(1-(2-[$^{18}$F]fluoroethyl)-4-(pyridin-4-yl)-1H-pyrazol-3-yl)phenoxy)methyl)-1,6-naphthyridine;
6-((4-(1-[$^{11}$C]methyl-4-(pyridin-4-yl)-1H-pyrazol-3-yl)phenoxy)methyl)pyrido[3,2-c]pyridazine;

6-((4-(1-(2-[$^{18}$F]fluoroethyl)-4-(pyridin-4-yl)-1H-pyrazol-3-yl)phenoxy)methyl)pyrido[3,2-c]pyridazine;
2-((4-(1-(2-[$^{18}$F]fluoroethyl)-4-(pyridin-4-yl)-1H-pyrazol-3-yl)phenoxy)methyl)quinazoline;
2-((4-(1-[$^{11}$C]methyl-4-(pyridin-4-yl)-1H-pyrazol-3-yl)phenoxy)methyl)pyrido[3,2-d]pyrimidine;
2-((4-(1-(2-[$^{18}$F]fluoroethyl)-4-(pyridin-4-yl)-1H-pyrazol-3-yl)phenoxy)methyl)pyrido[3,2-d]pyrimidine;
3-methyl-2-((4-(1-[$^{11}$C]methyl-4-(pyridin-4-yl)-1H-pyrazol-3-yl)phenoxy)methyl)quinazolin-4(3H)-one;
2-((4-(1-(2-[$^{18}$F]fluoroethyl)-4-(pyridin-4-yl)-1H-pyrazol-3-yl)phenoxy)methyl)-3-methylquinazolin-4(3H)-one;
3-[$^{11}$C]methyl-2-((4-(1-methyl-4-(pyridin-4-yl)-1H-pyrazol-3-yl)phenoxy)methyl)quinazolin-4(3H)-one;
3-(2-[$^{18}$F]fluoroethyl)-2-((4-(1-methyl-4-(pyridin-4-yl)-1H-pyrazol-3-yl)phenoxy)methyl)quinazolin-4(3H)-one;
3-methyl-2-((4-(1-[$^{11}$C]methyl-4-(pyridin-4-yl)-1H-pyrazol-3-yl)phenoxy)methyl)pyrido[3,2-d]pyrimidin-4(3H)-one;
2-((4-(1-(2-[$^{18}$F]fluoroethyl)-4-(pyridin-4-yl)-1H-pyrazol-3-yl)phenoxy)methyl)-3-methylpyrido[3,2-d]pyrimidin-4(3H)-one;
3-[$^{11}$C]methyl-2-((4-(1-methyl-4-(pyridin-4-yl)-1H-pyrazol-3-yl)phenoxy)methyl)pyrido[3,2-d]pyrimidin-4(3H)-one;
3-(2-[$^{18}$F]fluoroethyl)-2-((4-(1-methyl-4-(pyridin-4-yl)-1H-pyrazol-3-yl)phenoxy)methyl)pyrido[3,2-d]pyrimidin-4(3H)-one;
1,1-dioxo-2-methyl-3-((4-(1-[$^{11}$C]methyl-4-(pyridin-4-yl)-1H-pyrazol-3-yl)phenoxy)methyl)-2H-benzo[e][1,2,4]thiadiazine;
1,1-dioxo-2-methyl-3-((4-(1-(2-[$^{18}$F]fluoroethyl)-4-(pyridin-4-yl)-1H-pyrazol-3-yl)phenoxy)methyl)-2H-benzo[e][1,2,4]thiadiazine;
1,1-dioxo-2-[$^{11}$C]methyl-3-((4(4-(1-methyl-4-(pyridin-4-yl)-1H-pyrazol-3-yl)phenoxy)methyl)-2H-benzo[e][1,2,4]thiadiazine;
1,1-dioxo-2-(2-[$^{18}$F]fluoroethyl)-3-((4(4-(1-methyl-4-(pyridin-4-yl)-1H-pyrazol-3-yl)phenoxy)methyl)-2H-benzo[e][1,2,4]thiadiazine;
2-((4-(1-[$^{11}$C]methyl-4-(pyridin-4-yl)-1H-pyrazol-3-yl)phenoxy)methyl)benzo[d]oxazole;
2-((4-(1-(2-[$^{18}$F]fluoroethyl)-4-(pyridin-4-yl)-1H-pyrazol-3-yl)phenoxy)methyl)benzo[d]oxazole;
2-((4-(1-(2-[$^{18}$F]fluoroethyl)-4-(pyridin-4-yl)-1H-pyrazol-3-yl)phenoxy)methyl)-1-methyl-1H-benzo[d]imidazole;
1-(2-[$^{18}$F]fluoroethyl)-2-(4-(1-methyl-4-(pyridin-4-yl)-1H-pyrazol-3-yl)phenoxy)methyl)-1H-benzo[d]imidazole;
2-((4-(1-[$^{11}$C]methyl-4-(pyridin-4-yl)-1H-pyrazol-3-yl)phenoxy)methyl)oxazolo[5,4-b]pyridine;
2-((4-(1-(2-[$^{18}$F]fluoroethyl)-4-(pyridin-4-yl)-1H-pyrazol-3-yl)phenoxy)methyl)oxazolo[5,4-b]pyridine;
3-methyl-2-((4-(1-[$^{11}$C]methyl-4-(pyridin-4-yl)-1H-pyrazol-3-yl)phenoxy)methyl)-3H-imidazo[4,5-b]pyridine;
2-((4-(1-(2-[$^{18}$F]fluoroethyl)-4-(pyridin-4-yl)-1H-pyrazol-3-yl)phenoxy)methyl)-3-methyl-3H-imidazo[4,5-b]pyridine;
3-[$^{11}$C]methyl-2-((4-(1-methyl-4-(pyridin-4-yl)-1H-pyrazol-3-yl)phenoxy)methyl)-3H-imidazo[4,5-b]pyridine;
3-(2-[$^{18}$F]fluoroethyl)-2-((4-(1-methyl-4-(pyridin-4-yl)-1H-pyrazol-3-yl)phenoxy)methyl)-3H-imidazo[4,5-b]pyridine; and
2-((4-(1-(2-fluoroethyl)-4-(pyridin-4-yl)-1H-pyrazol-3-yl)phenoxy)methyl)-5-[$^{3}$H]benzo[d]oxazole.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). Individual cis or trans isomers of compounds of the invention may be prepared synthetically from commercially available starting materials using selective organic transformations, or by prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen and deuterium, or $^{11}$C, $^{12}$C and $^{13}$C.

Methods for Preparing Compounds of the Invention

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-9.

Scheme 1

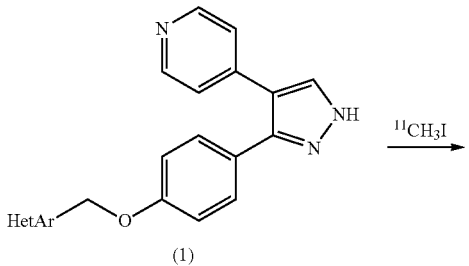

(1)

-continued

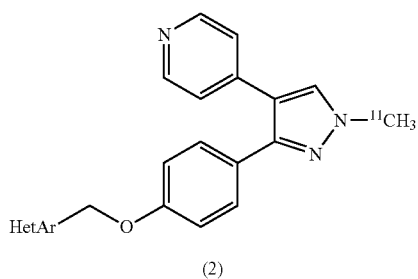

(2)

[¹¹C]methylated compounds of formula (2), wherein HetAr is as defined in formula (I), can be prepared as described in Scheme 1. Des-methyl compounds of formula (I), prepared using methodologies described herein or known to those of ordinary skill in the art, when treated with [¹¹C] methyl iodide in the presence of a base will provide compounds of formula (2). A mixture of isomers resulting from ¹¹C-methylation at either of the pyrazole nitrogens can be separated chromatographically. The [¹¹C]methyl iodide can be prepared by methodologies known to those of ordinary skill in the art, such as for example, by halogenation of ¹¹C methane in a gas phase process, or by reducing cyclotron-produced [¹¹C]carbon dioxide with lithium aluminum hydride followed by hydriodic acid treatment.

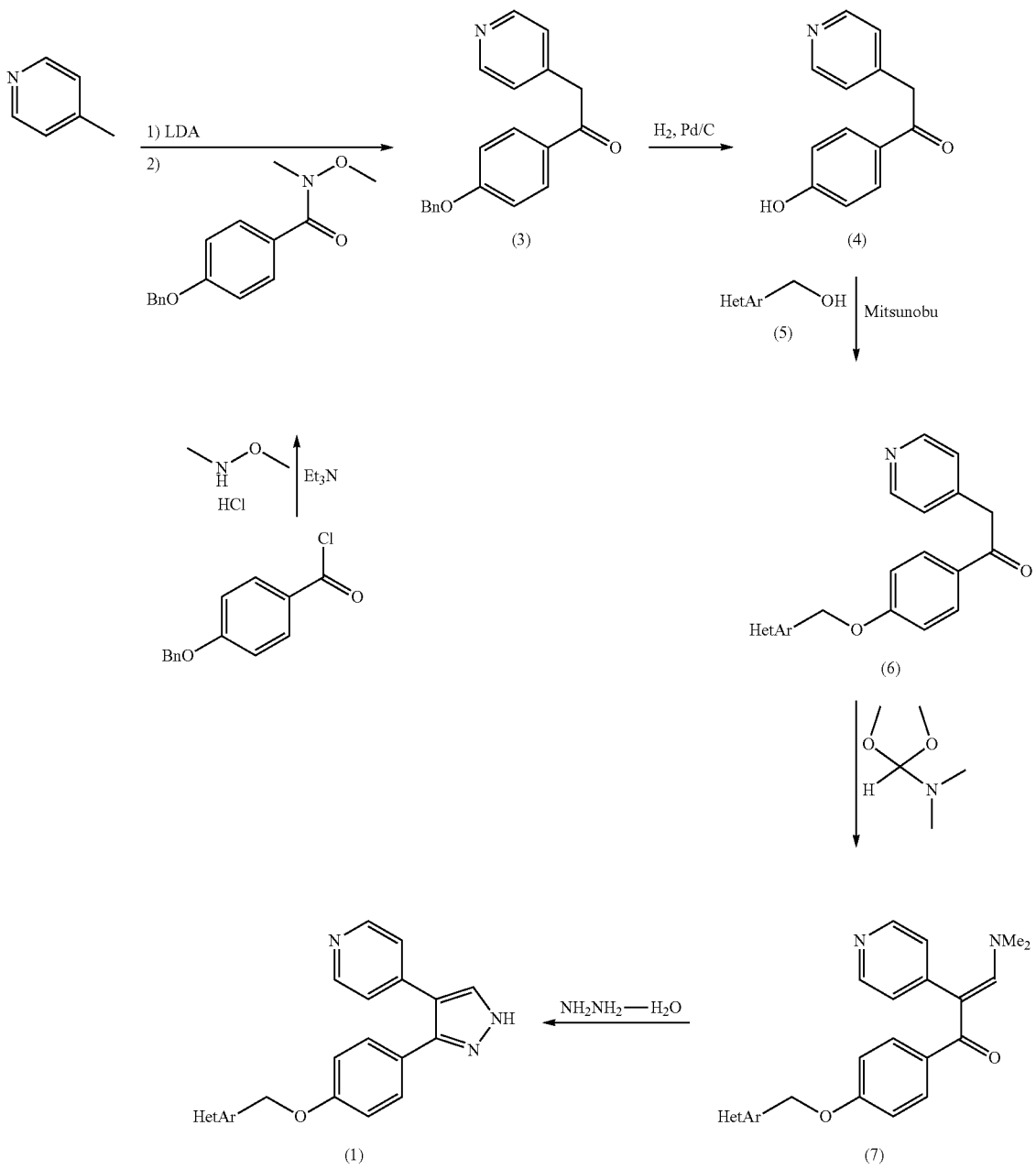

Des-methyl compounds of formula (1) can be prepared as described in Scheme 2. Treatment of 4-methylpyridine with lithium diisopropylamide (LDA) followed by 4-(benzyloxy)-N-methoxy-N-methylbenzamide will provide a compound of formula (3). The 4-(benzyloxy)-N-methoxy-N-methylbenzamide can be prepared by reacting 4-(benzyloxy)benzoyl chloride with N,O-dimethylhydroxylamine hydrochloride in the presence of triethylamine. The benzyl group of the compound of formula (3) can be removed via treatment with hydrogen over palladium/carbon, thereby providing phenolic compounds of formula (4). Using standard Mitsunobu reaction conditions known to those skilled in the art and widely available in the literature, reaction between compounds of formula (4) and heteroaromatic methanol compounds of formula (5) will provide compounds of formula (6). The heteroaromatic compounds of formula (5) may be selected from commercially available compounds or compounds obtainable by methods known in the art. Optionally, heteroaromatic compounds of formula (5) can be prepared from hydrolysis of commercially available halomethylheteroaryls or from reduction of heteroarylcarbaldehydes. If the appropriate halomethylheteroaryls or heteroarylcarbaldehydes are not commercially available, either may be prepared from the corresponding methyl substituted heteroaryl compound by treatment with N-bromosuccinimide (NBS) or N-chlorosuccinimide (NCS) for the halomethyl compounds, or with selenium dioxide for the carbaldehydes. Treatment of compounds of formula (6) with 1,1-dimethoxy-N,N-dimethylmethanamine will provide compounds of formula (7). Compounds of formula (7), when treated with hydrazine, will provide compounds of formula (1).

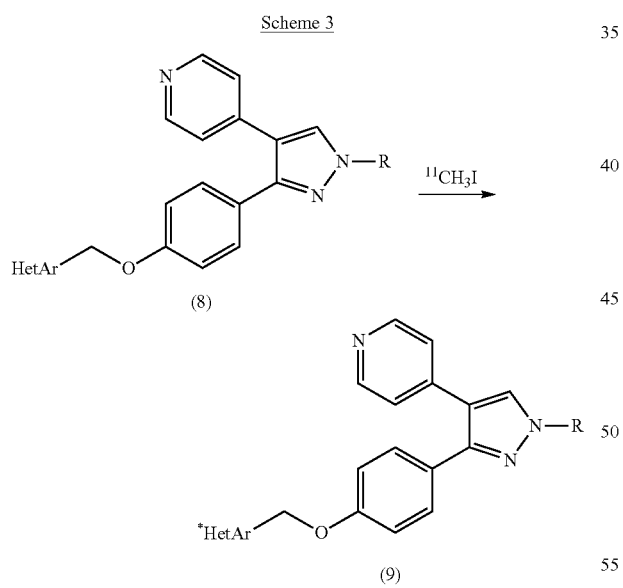

Compounds of formula (9) wherein HetAr includes a $^{11}$C-label can be prepared as described in Scheme 3. Compounds of formula (8), wherein HetAr comprises a functional group capable of undergoing alkylation (e.g., a primary or secondary amine), when treated with [$^{11}$C]methyl iodide in the presence of a base will provide heteroaromatic compounds of formula (9) comprising a carbon-radiolabel. In instances where the pyrazole nitrogen is unsubstituted (i.e., R=H), radiolabeling can also occur at the pyrazole nitrogen. Accordingly, in certain embodiments, preferably R is other than hydrogen in order to direct radiolabeling to the HetAr group. Mixtures of isomers resulting from $^{11}$C-methylation at either of the pyrazole nitrogens or at the HetAr group can be separated chromatographically.

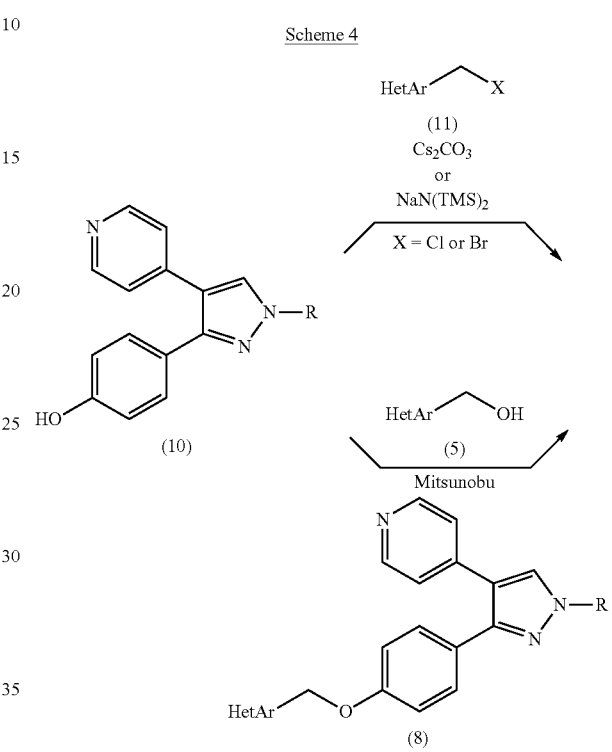

Compounds of formula (8) can be prepared as described in Scheme 4. Compounds of formula (10) when reacted with a heteroaromatic alkyl halide of formula (11) under basic conditions, or alternatively, with a heteroaromatic methanol compound of formula (5) under Mitsunobu conditions, will provide compounds of formula (8). Optionally, the functional group in the heteroaromatic compounds of formula (11) designated for alkylation with [$^{11}$C]methyl iodide can be protected as appropriate prior to the alkylation or Mitsunobu reactions of Scheme 4 in order to avoid interference with the alkylation or Mitsunobu processes. For example, where the heteroaromatic compound of formula (11) is selected from the group consisting of compounds of formulae (11a), (11b) and (11c),

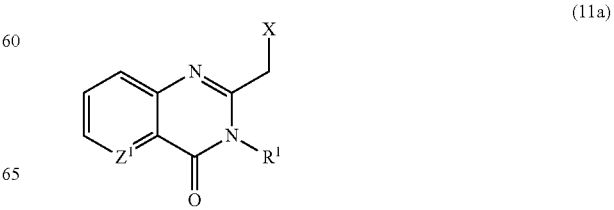

-continued (11b)

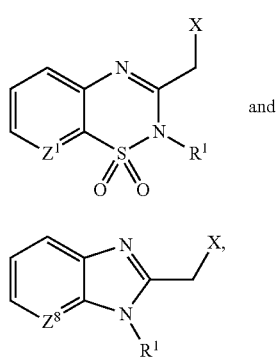

and (11c)

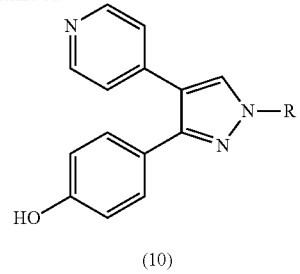

(10)

$R^1$ can be hydrogen, or a nitrogen-protecting group designed for removal after the ether linkage is established between the compound of formula (10) and the compound of formula (11). Likewise, in certain embodiments, the R substituent group in the compound of formula (10) can be other than hydrogen in order to avoid interference with the alkylation or Mitsunobu processes.

Compounds of formula (10), wherein R is hydrogen, methyl or ethyl can be prepared as described in Scheme 5. The compound of formula (3), when treated with 1,1-dimethoxy-N,N-dimethylmethanamine will provide compounds of formula (12). Compounds of formula (12), when treated with hydrazine, methyl hydrazine, or ethyl hydrazine will provide, respectively, compounds of formula (13) wherein R is hydrogen, methyl, or ethyl. The benzyl group of the compound of formula (13) can be removed via treatment with hydrogen over palladium/carbon, thereby providing phenolic compounds of formula (10).

Scheme 5

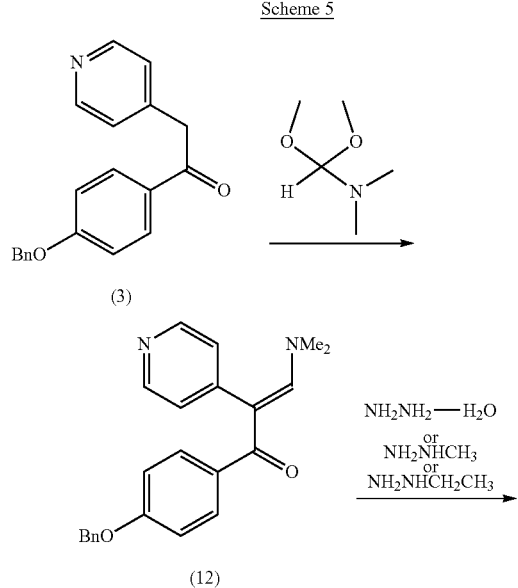

Scheme 6

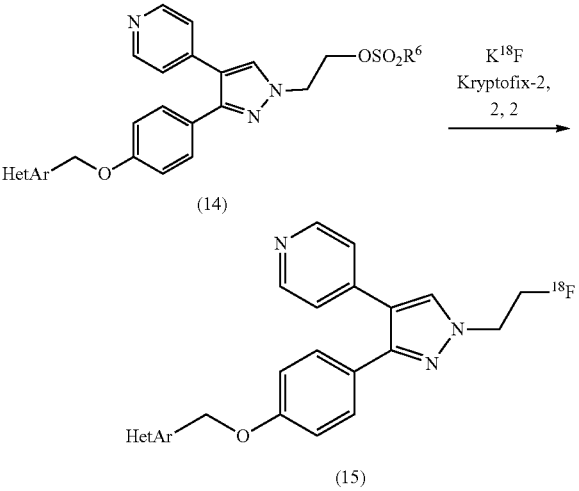

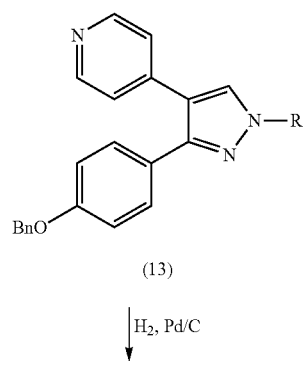

$^{18}$F-labeled compounds of formula (15), wherein HetAr is as defined in formula (I), can be prepared as described in Scheme 6. A sulfonate compound of formula (14) wherein $R^6$ is selected from —CH$_3$, 4-CH$_3$-Ph-, and 4-NO$_2$-Ph-, when treated with [$^{18}$F]potassium fluoride in the presence of Kryptofix-2,2,2 will provide $^{18}$F-labeled compounds of formula (15). The [$^{18}$F]fluoride source can be generated in a cyclotron by standard methods known by those skilled in the art. Although mesylate ($R^6$=CH$_3$), tosylate ($R^6$=4-CH$_3$-Ph), and nosylate ($R^6$=4-NO$_2$-Ph) sulfonate groups are preferred leaving groups in the fluorination, other suitable leaving groups can be used as appropriate.

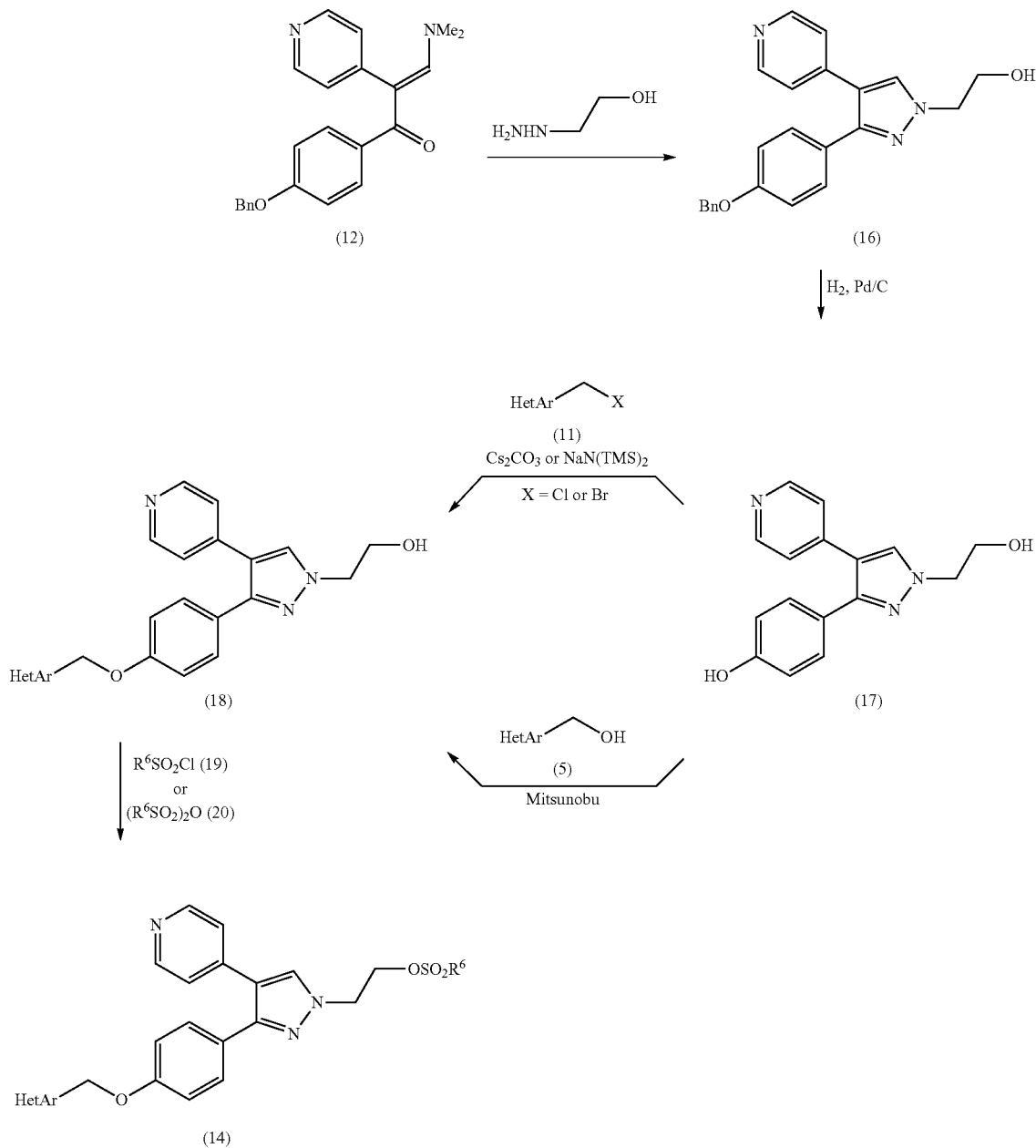

The sulfonate compounds of formula (14) can be prepared as described in Scheme 7. The compounds of formula (12), when treated with 2-hydroxyethylhydrazine, will provide compounds of formula (16). The benzyl group of the compounds of formula (16) can be removed via treatment with hydrogen over palladium/carbon, thereby providing phenolic compounds of formula (17). Compounds of formula (17), when combined with either compounds of formula (5) under Mitsunobu conditions, or compounds of formula (11) under basic alkylating conditions, will provide compounds of formula (18). Treatment of the compounds of formula (18) with a sulfonyl chloride of formula (19) (e.g., methanesulfonyl chloride) or a sulfonic anhydride of formula (20) (e.g., methanesulfonic anhydride, toluenesulfonic anhydride) in the presence of a base will provide sulfonate compounds of formula (14).

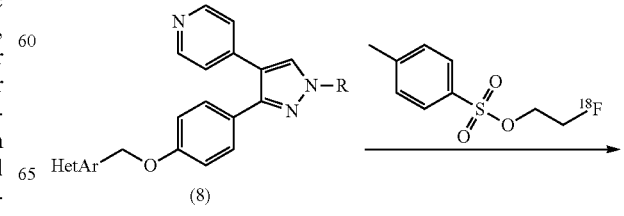

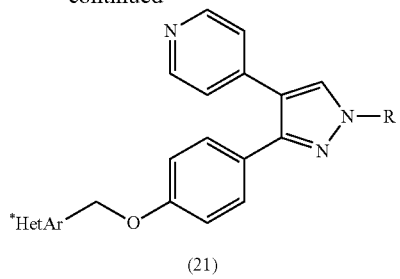

(21)

Compounds of formula (21) wherein HetAr includes a $^{18}$F-label can be prepared as described in Scheme 8. Compounds of formula (8), wherein HetAr comprises a functional group capable of undergoing alkylation (e.g., a primary or secondary amine), when treated with [$^{18}$F]fluoroethyl tosylate will provide heteroaromatic compounds of formula (21) comprising a $^{18}$F-labeled fluoroethyl group. In instances where the pyrazole nitrogen is unsubstituted (i.e., R=H), radiolabeling can also occur at the pyrazole nitrogen. Accordingly, in certain embodiments, preferably R is other than hydrogen in order to direct radiolabeling to the HetAr group. Mixtures of isomers resulting from $^{18}$F-fluoroethyl alkylation at either of the pyrazole nitrogens or at the HetAr group can be separated chromatographically. The [$^{18}$F]fluoroethyl tosylate can be prepared from [$^{18}$F]fluoride generated in a cyclotron by methods known to those skilled in the art.

Scheme 9

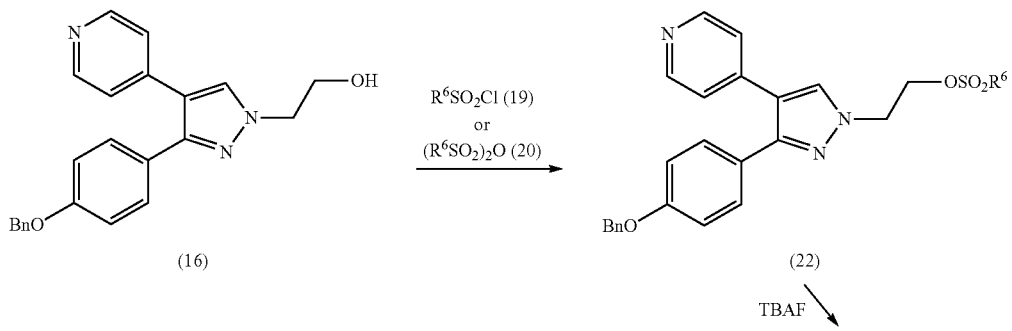

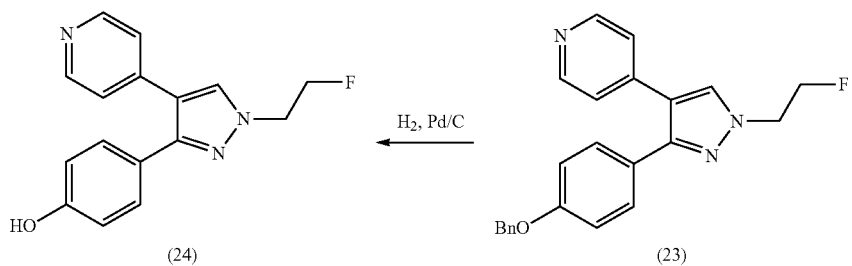

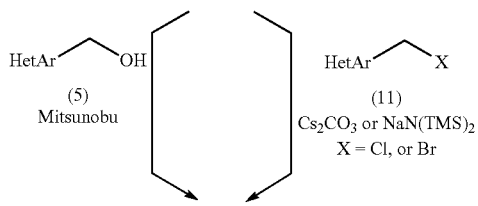

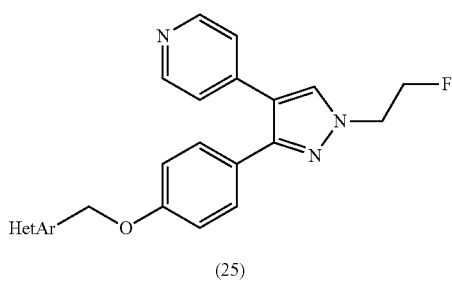

Non-radiolabeled compounds of formula (I) can be prepared as described according to Schemes 1-8. For example, compounds of formula (I) wherein R is ($^{12}$C)methyl can be prepared by following the synthetic sequences of Schemes 4 and 5. Compounds of formula (I) wherein R is 2-($^{19}$F)fluoroethyl can be prepared by following the synthetic sequences of Schemes 6 and 7, or alternatively, that of Scheme 9. Compounds of formula (16), when treated with a sulfonyl chloride of formula (19) (e.g., methanesulfonyl chloride) or a sulfonic anhydride of formula (20) (e.g., methanesulfonic anhydride, toluenesulfonic anhydride) will provide sulfonate compounds of formula (22). Treatment of compounds of formula (22) with tetrabutylammonium fluoride (TBAF) will provided fluorinated compounds of formula (23). The benzyl group of compounds of formula (23) can be removed with hydrogen over palladium/carbon, thereby providing phenolic compounds of formula (24). The ether linkage between compounds of formula (24) and compounds of formula (5) or (11) can be formed with Mitsunobu conditions or alkylating conditions, respectively, to provide compounds of formula (25).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Where compounds of the invention have at least one basic nitrogen, the compounds of the invention may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzensulfonic, carbonic, fumaric, maleic, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added.

The compounds of the invention can be used in the form of a pharmaceutically acceptable prodrug. The pharmaceutical compositions of the invention can contain compounds of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of PDE10A in cells, the compounds described in the invention can affect physiological processes in humans and animals. In this way, the compounds and compositions described in the invention are useful for treating and preventing diseases and disorders modulated by PDE10A. Typically, treatment or prevention of such diseases and disorders can be effected by selectively modulating PDE10A in a mammal, by administering a compound or composition of the invention, either alone or in combination with another active agent as part of a therapeutic regimen.

The compounds of the invention, including but not limited to those specified in the examples, possess an affinity for PDE10A and therefore, the compounds of the invention may be useful for the treatment and prevention of diseases or conditions such as certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. The compounds of the invention may be useful for the treatment of diabetes and related disorders such as obesity by regulating the cAMP signaling system. The compounds of the invention may be useful in preventing neurons from undergoing apoptosis by raising cAMP and cGMP levels and, thus, might possess anti-inflammatory properties. Neurodegenerative disorders that may be treatable with compounds of the invention include, but are not limited to, Alzheimer's disease, Huntington's disease, Parkinson's disease, multiple sclerosis, stroke and spinal cord injury. The growth of cancer cells is inhibited by cAMP and cGMP. Thus by raising cAMP and cGMP, compounds of the invention may also be useful for the treatment of different solid tumors and hematological malignancies such as renal cell carcinoma or breast cancer.

Compounds of the invention are particularly useful for treating and preventing a condition or disorder affecting memory or cognition, for example Alzheimer's disease, attention-deficit hyperactivity disorder, schizophrenia, or the cognitive deficits of schizophrenia or Alzheimer's disease.

The hypotheses around the physiological role of PDE10A and the therapeutic utility of PDE10A inhibitors derive in part from studies with papaverine, the first extensively profiled pharmacological compound for this target. See, e.g., Siuciak et al., "Inhibition of the striatum-enriched phosphodiesterase PDE10A: A novel approach to the treatment of psychosis", Neuropharmacology, v. 51, no. 2, August 2006, pp. 386-396. The PDE10A inhibitor papaverine was shown to be active in several antipsychotic models. Papaverine potentiated the cataleptic effect of the D2 receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Also, a method of treating certain neurologic and psychiatric disorders with the selective PDE10 inhibitor papaverine was disclosed (WO 03/0032579). In particular, the method relates to psychotic disorders such as schizophrenia, delusional disorders and drug-induced psychosis; to anxiety disorders such as panic and obsessive-compulsive disorder; and to movement disorders including Parkinson's disease and Huntington's disease. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. See, e.g., Rodefer et al., Eur. J. Neurosci., 4 (2005) 1070-1076.

More recent references to the usefulness of PDE10A inhibitors for the treatment of schizophrenia include: 1) Schmidt, C. J.; Chapin, D. S.; Cianfrogna, J.; Corman, M. L.; Hajos, M.; Harms, J. F.; Hoffman, W. E.; Lebel, L. A.; McCarthy, S. A.; Nelson, F. R.; Proulx-LaFrance, C.; Majchrzak, A. D.; Ramirez, A. D.; Schmidt, K.; Seymour, P. A.; Siuciak, J. A.; Tingley, F. D., III; Williams, R. D.; Verhoest, P. R.; Menniti, F. S. Preclinical Characterization of Selective Phosphodiesterase 10A Inhibitors: A New Therapeutic Approach to the Treatment of Schizophrenia. J. Pharm. Exp. Ther. 2008, 325 (2), 681-690; and 2) Jan Kehler and Jacob Nielsen, PDE10A Inhibitors: Novel Therapeutic Drugs for Schizophrenia, Current Pharmaceutical Design, 2011, 17, 137-150.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide, prodrug, or radiolabeled form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 30 mg/kg/day. For purposes of oral administration, more preferable doses can be in the range of from about 0.0003 to about 1 mg/kg/day. If desired, the effective daily dose can be divided into multiple doses for purposes of administration; consequently, single dose compositions may contain such amounts or submultiples thereof to make up the daily dose.

Compounds and compositions of the invention also are useful as diagnostic tools. The ability of PET (positron emission tomography) and sPECT (single photon emission computed tomography) to probe the degree of receptor occupancy in humans and animals by endogenous ligands or drugs is widely recognized. This constitutes the use of PET as a biomarker to assess efficacy of pharmacological interventions with drugs. The topic and use of positron-emitting ligands for these purposes has been generally reviewed, for example in "PET ligands for assessing receptor occupancy in vivo" Burns, et al Annual Reports in Medicinal Chemistry (2001), 36, 267-276; "Ligand-receptor interactions as studied by PET: implications for drug development" by Jarmo Hietala, Annals of Medicine (Helsinki) (1999), 31(6), 438-443; "Positron emission tomography neuroreceptor imaging as a tool in drug discovery, research and development" Burns, et al. Current Opinion in Chemical Biology (1999), 3(4), 388-394. The compounds of the invention, synthesized with $^{11}$C, $^{18}$F, or other positron-emitting isotopes are suitable ligand tools for PET; a number of positron-emitting reagents have been synthesized, are available, and are known to those skilled in the art. Especially suitable compounds of the invention for this use are those wherein a $^{11}$CH$_3$ group can be incorporated in by reaction with $^{11}$CH$_3$I. Also, especially suitable compounds of the use are those wherein a $^{18}$F group can be incorporated into the compound by reaction with $^{18}$F-fluoride anion. The incorporation of $^{11}$CH$_3$ can be carried out according to a method such as that described in Example 10. In a like manner, other compounds of formula (I) can be prepared for use in PET studies. The incorporation of $^{18}$F can be carried out according to a method such as that described in Example 11. In a like manner, other compounds of formula (I) can be prepared for use in PET studies. Among compounds of the invention that are suitable for use as ligands for PET studies are $^3$H, $^{18}$F and $^{11}$C isotopes of compounds of the invention, including, but not limited to 2-((4-(1-[$^{11}$C]methyl-4-(pyridin-4-yl)-1H-pyrazol-3-yl)phenoxy)methyl)-1,5-naphthyridine;

2-((4-(1-(2-[$^{18}$F]fluoroethyl)-4-pyridin-4-yl)-1H-pyrazol-3-yl)phenoxy)methyl)-1,5-naphthyridine;

2-((4-(1-[$^{11}$C]methyl-4-(pyridin-4-yl)-1H-pyrazol-3-yl)phenoxy)methyl)-1,6-naphthyridine;

2-((4-(1-(2-[$^{18}$F]fluoroethyl)-4-pyridin-4-yl)-1H-pyrazol-3-yl)phenoxy)methyl)-1,6-naphthyridine;

6-((4-(1-[$^{11}$C]methyl-4-(pyridin-4-yl)-1H-pyrazol-3-yl)phenoxy)methyl)pyrido[3,2-c]pyridazine;

6-((4-(1-(2-[$^{18}$F]fluoroethyl)-4-(pyridin-4-yl)-1H-pyrazol-3-yl)phenoxy)methyl)pyrido[3,2-c]pyridazine;

2-((4-(1-(2-[$^{18}$F]fluoroethyl)-4-(pyridin-4-yl)-1H-pyrazol-3-yl)phenoxy)methyl)quinazoline;

2-((4-(1-[$^{11}$C]methyl-4-(pyridin-4-yl)-1H-pyrazol-3-yl)phenoxy)methyl)pyrido[3,2-d]pyrimidine;

2-((4-(1-(2-[$^{18}$F]fluoroethyl)-4-(pyridin-4-yl)-1H-pyrazol-3-yl)phenoxy)methyl)pyrido[3,2-d]pyrimidine;

3-methyl-24(4-(1-[$^{11}$C]methyl-4-(pyridin-4-yl)-1H-pyrazol-3-yl)phenoxy)methyl)quinazolin-4(3H)-one;

2-((4-(1-(2-[$^{18}$F]fluoroethyl)-4-(pyridin-4-yl)-1H-pyrazol-3-yl)phenoxy)methyl)-3-methylquinazolin-4(3H)-one;

3-[$^{11}$C]methyl-2-((4-(1-methyl-4-(pyridin-4-yl)-1H-pyrazol-3-yl)phenoxy)methyl)quinazolin-4(3H)-one;

3-(2-[$^{18}$F]fluoroethyl)-2-((4-(1-methyl-4-(pyridin-4-yl)-1H-pyrazol-3-yl)phenoxy)methyl)quinazolin-4(3H)-one;

3-methyl-2-((4-(1-[$^{11}$C]methyl-4-(pyridin-4-yl)-1H-pyrazol-3-yl)phenoxy)methyl)pyrido[3,2-d]pyrimidin-4(3H)-one;

2-((4-(1-(2-[$^{18}$F]fluoroethyl)-4-(pyridin-4-yl)-1H-pyrazol-3-yl)phenoxy)methyl)-3-methylpyrido[3,2-d]pyrimidin-4(3H)-one;

3-[$^{11}$C]methyl-2-((4-(1-methyl-4-(pyridin-4-yl)-1H-pyrazol-3-yl)phenoxy)methyl)pyrido[3,2-d]pyrimidin-4(3H)-one;

3-(2-[$^{18}$F]fluoroethyl)-2-((4-(1-methyl-4-(pyridin-4-yl)-1H-pyrazol-3-yl)phenoxy)methyl)pyrido[3,2-d]pyrimidin-4(3H)-one;

1,1-dioxo-2-methyl-3-((4(4-(1-[$^{11}$C]methyl-4-(pyridin-4-yl)-1H-pyrazol-3-yl)phenoxy)methyl)-2H-benzo[e][1,2,4]thiadiazine;

1,1-dioxo-2-methyl-3-((4(4-(1-(2-[$^{18}$F]fluoroethyl)-4-(pyridin-4-yl)-1H-pyrazol-3-yl)phenoxy)methyl)-2H-benzo[e][1,2,4]thiadiazine;

1,1-dioxo-2-[$^{11}$C]methyl-3-((4(4-(1-methyl-4-(pyridin-4-yl)-1H-pyrazol-3-yl)phenoxy)methyl)-2H-benzo[e][1,2,4]thiadiazine;

1,1-dioxo-2-(2-[$^{18}$F]fluoroethyl)-3-((4(4-(1-methyl-4-(pyridin-4-yl)-1H-pyrazol-3-yl)phenoxy)methyl)-2H-benzo[e][1,2,4]thiadiazine;

2-((4-(1-[$^{11}$C]methyl-4-(pyridin-4-yl)-1H-pyrazol-3-yl)phenoxy)methyl)benzo[d]oxazole;

2-((4-(1-(2-[$^{18}$F]fluoroethyl)-4-(pyridin-4-yl)-1H-pyrazol-3-yl)phenoxy)methyl)benzo[d]oxazole;

2-((4-(1-(2-[$^{18}$F]fluoroethyl)-4-(pyridin-4-yl)-1H-pyrazol-3-yl)phenoxy)methyl)-1-methyl-1H-benzo[d]imidazole;

1-(2-[$^{18}$F]fluoroethyl)-2-((4-(1-methyl-4-(pyridin-4-yl)-1H-pyrazol-3-yl)phenoxy)methyl)-1H-benzo[d]imidazole;

2-((4-(1-[$^{11}$C]methyl-4-(pyridin-4-yl)-1H-pyrazol-3-yl)phenoxy)methyl)oxazolo[5,4-b]pyridine;

2-((4-(1-(2-[$^{18}$F]fluoroethyl)-4-(pyridin-4-yl)-1H-pyrazol-3-yl)phenoxy)methyl)oxazolo[5,4-b]pyridine;

3-methyl-2-((4-(1-[$^{11}$C]methyl-4-(pyridin-4-yl)-1H-pyrazol-3-yl)phenoxy)methyl)-3H-imidazo[4,5-b]pyridine;

2-((4-(1-(2-[$^{18}$F]fluoroethyl)-4-(pyridin-4-yl)-1H-pyrazol-3-yl)phenoxy)methyl)-3-methyl-3H-imidazo[4,5-b]pyridine;

3-[$^{11}$C]methyl-2-((4-(1-methyl-4-(pyridin-4-yl)-1H-pyrazol-3-yl)phenoxy)methyl)-3H-imidazo[4,5-b]pyridine;

3-(2-[$^{18}$F]fluoroethyl)-2-((4-(1-methyl-4-(pyridin-4-yl)-1H-pyrazol-3-yl)phenoxy)methyl)-3H-imidazo[4,5-b]pyridine; and 2-((4-(1-(2-fluoroethyl)-4-(pyridin-4-yl)-1H-pyrazol-3-yl)phenoxy)methyl)-5-[$^3$H]benzo[d]oxazole.

The compounds and processes of the invention will be better understood by reference to the following examples, which are intended as an illustration of and not a limitation upon the scope of the invention.

EXAMPLES

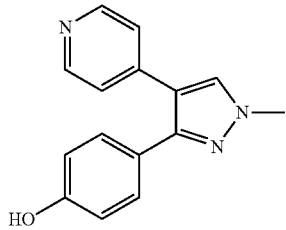

Intermediate 1

4-(1-methyl-4-(pyridin-4-yl)-1H-pyrazol-3-yl)phenol

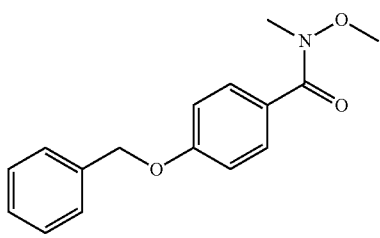

Intermediate 1A 4-(benzyloxy)-N-methoxy-N-methylbenzamide

A stirred suspension of 4-(benzyloxy)benzoic acid (CAS#1486-51-7, Aldrich #512354, 5 g, 21.91 mmol) and N,N-dimethylformamide (0.254 mL, 3.29 mmol) in dichloromethane (50 mL) was chilled to 0° C. To this stirred mixture was added dropwise oxalyl chloride (3.84 mL, 43.9 mmol). The reaction mixture was stirred for 18 hours, while slowly warming to ambient temperature. Volatiles were removed under reduced pressure to give a white solid (5.3 g, 98%). $^1$H NMR (300 MHz, CDCl$_3$) δ 8.11-8.05 (m, 2H), 7.45-7.32 (m, 5H), 7.06-7.01 (m, 2H), 5.16 (s, 2H). This crude material was used without further purification by adding CH$_2$Cl$_2$ (70 mL) and N,O-dimethylhydroxylamine hydrochloride (2.51 g, 25.8 mmol). The reaction mixture was cooled to 0° C. and treated dropwise with Et$_3$N (8.98 mL, 64.4 mmol). After 1 h at 0° C., the mixture was stirred at room temperature (RT) for 18 h. The reaction mixture was filtered free of insoluble salts, washed with dilute aqueous HCl, then with dilute aqueous sodium carbonate, and dried over MgSO$_4$. Drying agent was removed by filtration and the filtrate was concentrated under reduced pressure to give a white solid (5.45 g, 93%). $^1$H NMR (300 MHz, methanol-d$_4$) δ 7.69-7.62 (m, 2H), 7.47-7.27 (m, 5H), 7.07-7.01 (m, 2H), 5.13 (s, 2H), 3.58 (s, 3H), 3.33 (s, 3H). MS (DCI—NH$_3$) m/z=272 (M+H)$^+$, m/z=289 (M+NH$_4$)$^+$.

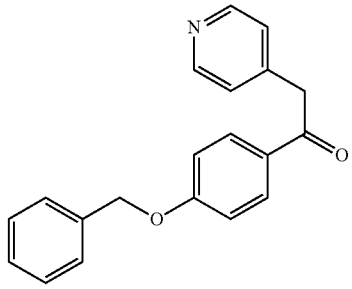

Intermediate 1B 1-(4-(benzyloxy)phenyl)-2-(pyridin-4-yl)ethanone

An oven-dried, 3-neck, 250 mL round bottom flask equipped with a magnetic stirbar, addition funnel, and internal thermometer was cooled to ambient temperature under a stream of dry nitrogen. The flask was charged with lithium diisopropylamide, 1.8M solution in THF/heptane/ethylbenzene (22.07 mL, 39.7 mmol), diluted with THF (30 mL), and the solution was chilled to 0° C. To this stirred, 0° C. solution was added dropwise via syringe a solution of 4-methylpyridine (3.87 mL, 39.7 mmol) in THF (25 mL). After the addition was complete the reaction mixture was stirred at 0° C. for 30 minutes. The reaction mixture was then further chilled to −78° C. To this stirred, −78° C. solution was added dropwise via the addition funnel a solution of 4-(benzyloxy)-N-methoxy-N-methylbenzamide (4.9 g, 18.06 mmol) in THF (30 mL). The resulting reaction mixture was stirred at −78° C. for 2 hours. At this point the reaction was quenched with 4.5 equivalents of acetic acid (4.7 mL) added dropwise to the −78° C. reaction mixture. The reaction was then allowed to slowly warm to ambient temperature overnight. Desired product had precipitated from the reaction mixture. Saturated aqueous sodium bicarbonate was added to the reaction mixture. The two layers were filtered to collect the white, insoluble product (3.765 g, 68.7%), then the layers were separated. The aqueous layer was extracted with EtOAc. The combined EtOAc extracts were diluted with CHCl$_3$ to better solubilize the product, then dried (MgSO$_4$), and filtered. The filtrate was concentrated under reduced pressure to give a pale yellow solid. This solid was rinsed with Et$_2$O repeatedly to remove 4-methylpyridine. The pale yellow solid weighed 1.456 g (26.7%, 95% overall). $^1$H NMR (300 MHz, CDCl$_3$) δ 9.55 (dd, J=4.5, 1.5, 2H), 8.00-7.94 (m, 2H), 7.45-7.31 (m, 5H), 7.19 (d, J=5.9, 2H), 7.05-6.99 (m, 2H), 5.14 (s, 2H), 4.22 (s, 2H). MS (DCI—NH$_3$) m/z=304 (M+H)$^+$.

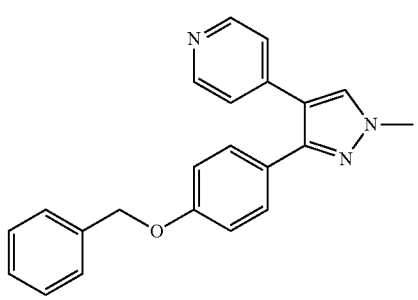

Intermediate 1C

4-(3-(4-(benzyloxy)phenyl)-1-methyl-1H-pyrazol-4-yl)pyridine

Dimethoxymethyl dimethylamine (9.84 mL) was added to a solution of Intermediate 1B, 1-(4-(benzyloxy)phenyl)-2-(pyridin-4-yl)ethanone (15 g) in toluene (150 mL). The reaction mixture was heated at reflux for 1 h. The solution was cooled to ambient temperature, and concentrated under reduced pressure. The residue was dissolved in EtOH (150 mL) and methyl hydrazine (5.27 mL) was added. The resulting solution was heated at reflux for 2 h. After cooling to ambient temperature, the solid residue was collected by filtration and re-crystallized from EtOAc to yield 4-(3-(4-(benzyloxy)phenyl)-1-methyl-1H-pyrazol-4-yl)pyridine (8 g, 47%).

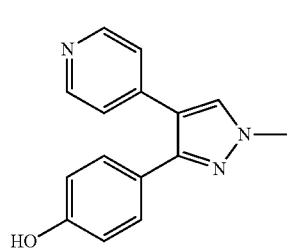

Intermediate 1

4-(1-methyl-4-(pyridin-4-yl)-1H-pyrazol-3-yl)phenol

Pd/C (3 g) was added to a solution of Intermediate 1C, 4-(3-(4-(benzyloxy)phenyl)-1-methyl-1H-pyrazol-4-yl)pyridine (7.6 g) in EtOAc/EtOH (35 mL+35 mL). The mixture was stirred in an autoclave at 5 atm $H_2$ for 48 h. Pd/C was filtered off and the filtrate was concentrated under reduced pressure to yield the crude product. Purification by flash chromatography afforded pure Intermediate 1, 4-(1-methyl-4-(pyridin-4-yl)-1H-pyrazol-3-yl)phenol (5 g, 89%). $^1$H NMR (300 MHz, methanol-$d_4$) δ 8.36 (dd, J=4.7, 1.6, 2H), 7.99 (s, 1H), 7.29 (dd, J=4.7, 1.7, 2H), 7.25-7.20 (m, 2H), 6.83-6.77 (m, 2H), 3.95 (s, 3H). MS (DCI—$NH_3$) m/z=252 (M+H)$^+$. (Note: Experimental details for Intermediate 1 are also published in *Journal of Medicinal Chemistry* 2009, 52(16), 5188-5196, Compound 24).

Intermediate 2

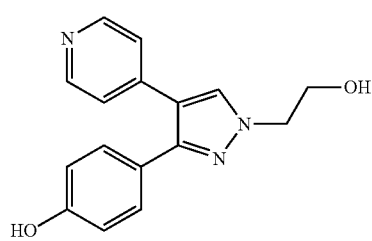

4-(1-(2-hydroxyethyl)-4-(pyridin-4-yl)-1H-pyrazol-3-yl)phenol

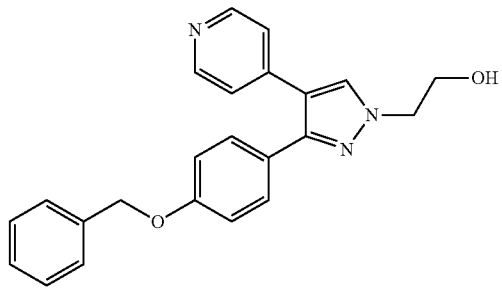

Intermediate 2A

2-(3-(4-(benzyloxy)phenyl)-4-(pyridin-4-yl)-1H-pyrazol-1-yl)ethanol

Dimethoxymethyl dimethylamine (23.26 mL) was added to a solution of Intermediate 1B, 1-(4-(benzyloxy)phenyl)-2-(pyridin-4-yl)ethanone (35.4 g) in toluene (400 mL). The reaction mixture was heated at reflux for 1 h. The solution was cooled to ambient temperature, and concentrated under reduced pressure. The residue was dissolved in EtOH (350 mL) and 2-hydroxyethylhydrazine (15.82 mL) was added. The resulting solution was heated at reflux for 2 h. After concentration under reduced pressure, the residue was purified by flash column chromatography to yield 2-(3-(4-(benzyloxy)phenyl)-4-(pyridin-4-yl)-1H-pyrazol-1-yl)ethanol (8.5 g, 39%).

Intermediate 2

4-(1-(2-hydroxyethyl)-4-(pyridin-4-yl)-1H-pyrazol-3-yl)phenol

Pd/C (3 g) was added to a solution of Intermediate 2A, 2-(3-(4-(benzyloxy)phenyl)-4-(pyridin-4-yl)-1H-pyrazol-1-yl)ethanol (7.5 g) in EtOAc/EtOH (35 mL+35 mL). The mixture was stirred in autoclave at 5 atm $H_2$ for 48 h. Pd/C was filtered off and the filtrate was concentrated under reduced pressure to yield the crude product. Purification by flash column chromatography afforded pure Intermediate 2,4-(1-(2-hydroxyethyl)-4-(pyridin-4-yl)-1H-pyrazol-3-yl)phenol (5 g, 88%).

Intermediate 3

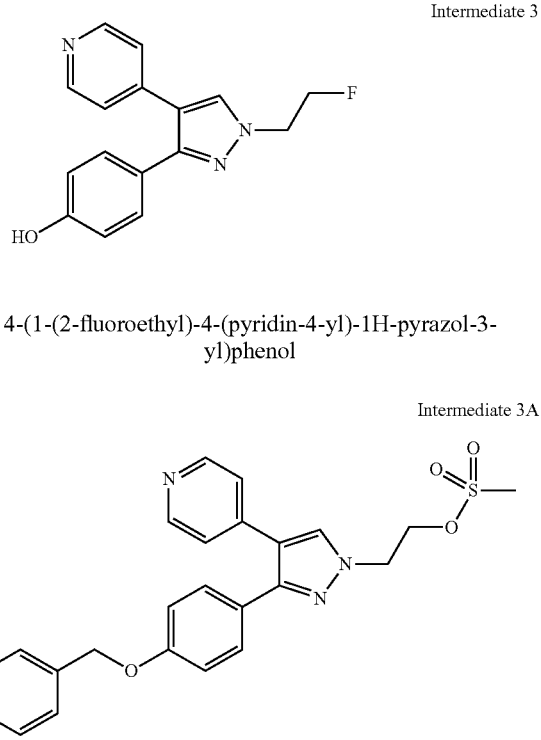

4-(1-(2-fluoroethyl)-4-(pyridin-4-yl)-1H-pyrazol-3-yl)phenol

Intermediate 3A 2-(3-(4-(benzyloxy)phenyl)-4-(pyridin-4-yl)-1H-pyrazol-1-yl)ethyl methanesulfonate Intermediate 2,4-(1-(2-hydroxyethyl)-4-(pyridin-4-yl)-1H-pyrazol-3-yl)phenol (8.15 g) was dissolved in DCM (100 mL), and NEt₃ (4.59 mL) was added. The solution was cooled to 0° C. Methanesulfonyl chloride (2.07 mL) was added dropwise, and the mixture was allowed to warm to ambient temperature. The reaction mixture was washed first with citric acid, then with water. The organic layer was dried (MgSO₄), filtered, and concentrated under reduced pressure to yield 2-(3-(4-(benzyloxy)phenyl)-4-(pyridin-4-yl)-1H-pyrazol-1-yl)ethyl methanesulfonate (8.6 g, 97%).

Intermediate 3B

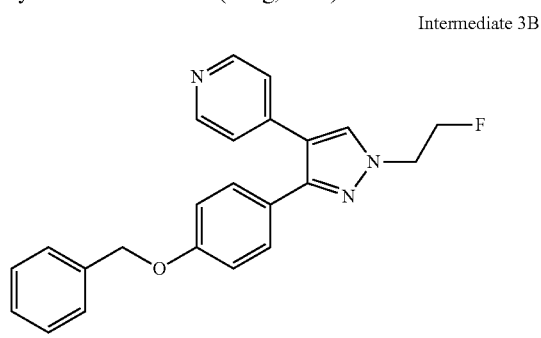

4-(3-(4-(benzyloxy)phenyl)-1-(2-fluoroethyl)-1H-pyrazol-4-yl)pyridine

Intermediate 3A, 2-(3-(4-(benzyloxy)phenyl)-4-(pyridin-4-yl)-1H-pyrazol-1-yl)ethyl methanesulfonate (11 g) was added to a 1M solution of tetrabutylammonium fluoride in THF (150 mL) and the reaction mixture was stirred overnight at ambient temperature. The reaction mixture was concentrated under reduced pressure and the residue was purified by flash column chromatography to obtain the desired Intermediate 3B, 4-(3-(4-(benzyloxy)phenyl)-1-(2-fluoroethyl)-1H-pyrazol-4-yl)pyridine (2.1 g, 23%) and the side product 4-(3-(4-(benzyloxy)phenyl)-1-vinyl-1H-pyrazol-4-yl)pyridine (2.0 g, 30%).

Intermediate 3

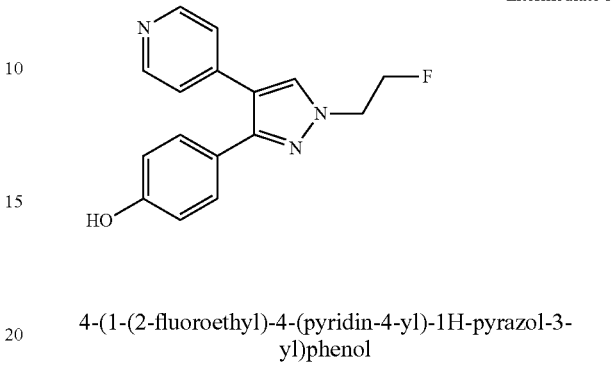

4-(1-(2-fluoroethyl)-4-(pyridin-4-yl)-1H-pyrazol-3-yl)phenol

Pd/C (1 g) was added to a solution of Intermediate 3B, 4-(3-(4-(benzyloxy)phenyl)-1-(2-fluoroethyl)-1H-pyrazol-4-yl)pyridine (2.1 g) in EtOAc/EtOH (30 mL+30 mL). The mixture was stirred in autoclave at 2.5 atm H₂ for 18 h. Pd/C was filtered off and the filtrate was concentrated under reduced pressure to yield the crude product. Purification by flash column chromatography afforded the pure product, 4-(1-(2-fluoroethyl)-4-(pyridin-4-yl)-1H-pyrazol-3-yl)phenol (1.46 g, 92%). $^1$H NMR (300 MHz, methanol-$d_4$) δ 8.37 (dd, J=4.6, 1.6, 2H), 8.08 (s, 1H), 7.31 (dd, J=4.6, 1.7, 2H), 7.27-7.22 (m, 2H), 6.83-6.78 (m, 2H), 4.81 (dt, J=47.1, 4.7, 2H), 4.49 (dt, J=26.6, 4.7, 2H). MS (DCI—NH₃) m/z=284 (M+H)⁺. (Note: Alternative preparation experimental details published in *Journal of Medicinal Chemistry* 2011, 54, 5820-5835, Compound 8b)

Intermediate 4

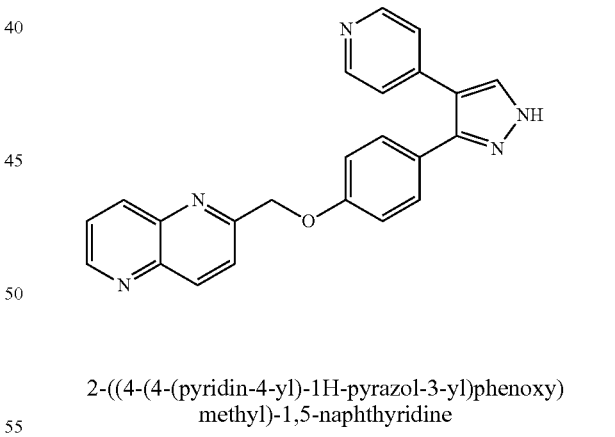

2-((4-(4-(pyridin-4-yl)-1H-pyrazol-3-yl)phenoxy)methyl)-1,5-naphthyridine

Intermediate 4A

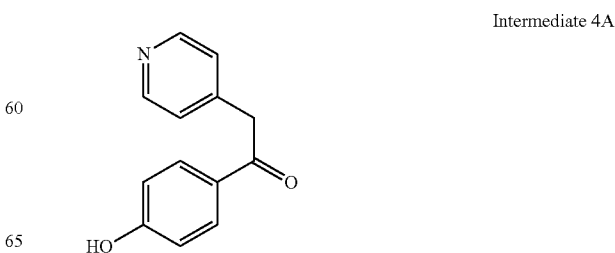

1-(4-hydroxyphenyl)-2-(pyridin-4-yl)ethanone

Intermediate 1B, 1-(4-(benzyloxy)phenyl)-2-(pyridin-4-yl)ethanone (5.22 g, 17.21 mmol) and solvent THF (60 mL) were added to 20% Pd(OH)$_2$—C, wet (1.044 g, 7.43 mmol) in a 250 mL stainless steel pressure bottle. The reaction mixture was stirred for 3 hr at 30 psi and ambient temperature. HPLC indicated that both starting material and product were present, so MeOH (10 mL) was added and the reaction was run for an additional 1 h. The reaction mixture was filtered through a nylon membrane and the filtrate was concentrated under reduced pressure to give a pale yellow solid (3.13 g, 85% yield). Much of the yellow color was removed by rinsing with MeOH. After the MeOH rinses, the solid was rinsed with Et$_2$O, then dried in a vacuum oven at 50° C. for 4 hours. This vacuum-dried sample weighed 2.071 g (56.4%). $^1$H NMR (300 MHz, DMSO-d$_6$) δ 10.38 (br s, 1H), 8.52-8.45 (m, 2H), 7.96-7.89 (m, 2H), 7.29-7.24 (m, 2H), 6.90-6.83 (m, 2H), 4.35 (s, 2H). MS (DCI—NH$_3$) m/z=214 (M+H)$^+$, m/z=231 (M+NH$_4$)$^+$.

Intermediate 4B

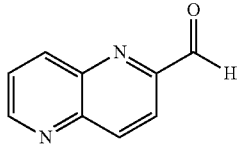

1,5-naphthyridine-2-carbaldehyde

A 100 mL round bottom flask equipped with a condenser (with a calcium sulfate drying tube) and a magnetic stirbar was charged with 2-methyl-1,5-naphthyridine (CAS#7675-32-3, Synchem-OHG #CDP146FP1, 433 mg, 3.0 mmol). Dioxane (10 mL) was added to give a stirred solution, then selenium dioxide (366 mg, 3.3 mmol) was added and the reaction mixture was heated to reflux with an oil bath. The stirred reaction mixture was maintained at reflux for 2 h, then cooled to ambient temperature and filtered through diatomaceous earth. The filtrate was concentrated under reduced pressure and the residue was purified by column chromatography on an Analogix IF-280 (Varian SF25-60 g, 100:0 to 0:100 hexane/EtOAc). Fractions #10-17 were combined and concentrated under reduced pressure to give a white solid that was dried overnight in a vacuum oven at ambient temperature. The dried solid Intermediate 4B, 1,5-naphthyridine-2-carbaldehyde weighed 229 mg (48%). $^1$H NMR (300 MHz, CDCl$_3$) δ 10.25 (d, J=0.9 Hz, 1H), 9.12 (dd, J=4.2, 1.6 Hz, 1H), 8.60-8.54 (m, 2H), 8.28 (d, J=8.7 Hz, 1H), 7.77 (dd, J=8.6, 4.2 Hz, 1H). MS (DCI—NH$_3$) m/z=159 (M+H)$^+$, m/z=176 (M+NH$_4$)$^+$.

Intermediate 4C

(1,5-naphthyridin-2-yl)methanol

A 100 mL round bottom flask equipped with a magnetic stirbar was charged with Intermediate 4B, 1,5-naphthyridine-2-carbaldehyde (200 mg, 1.265 mmol). Ethanol (12.6 mL) was added to give a solution. To this stirred solution was added, portionwise, sodium borohydride (47.8 mg, 1.265 mmol). The reaction mixture was stirred at ambient temperature for 15 minutes, then quenched with aqueous sodium bicarbonate. Volatiles were removed under reduced pressure and the residue was partitioned between EtOAc and water. The aqueous layer was extracted once more with EtOAc, then the combined organic layers were dried (MgSO$_4$) and filtered. The filtrate was concentrated under reduced pressure to give (1,5-naphthyridin-2-yl)methanol as a pale yellow solid that was purified by eluting through a plug of silica gel with 100% EtOAc. After evaporation of the solvent under reduced pressure, an off white solid was obtained, which was dried in a vacuum oven at ambient temperature for 3 days to give (1,5-naphthyridin-2-yl)methanol (142 mg, 70%). $^1$H NMR (300 MHz, methanol-d$_4$) δ 8.94 (dd, J=4.3, 1.6 Hz, 1H), 8.47-8.40 (m, 2H), 7.96 (d, J=8.8 Hz, 1H), 7.79 (dd, J=8.6, 4.3 Hz, 1H), 4.91 (s, 2H). MS (DCI—NH$_3$) m/z=161 (M+H)$^+$, m/z=178 (M+NH$_4$)$^+$.

Intermediate 4D

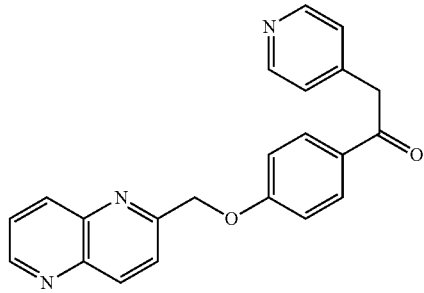

1-(4-((1,5-naphthyridin-2-yl)methoxy)phenyl)-2-(pyridin-4-yl)ethanone

Intermediate 4C, (1,5-naphthyridin-2-yl)methanol (142 mg, 0.887 mmol), Intermediate 4A, 1-(4-hydroxyphenyl)-2-(pyridin-4-yl)ethanone (158 mg, 0.739 mmol), and triphenylphosphine (310 mg, 1.182 mmol) were dissolved in dioxane (6 mL). To this stirred solution was added di-tert-butyl azodicarboxylate (272 mg, 1.182 mmol). The reaction mixture was stirred overnight at ambient temperature under a dry nitrogen atmosphere. The reaction mixture was diluted with aqueous sodium bicarbonate and extracted with CHCl$_3$. The combined organic layers were dried (MgSO$_4$) and filtered. The filtrate was concentrated under reduced pressure to give a yellow oil. The oil was purified by column chromatography on an Analogix IF-280 (Varian SF25-80 g, 100% DCM to 97:3 DCM/2M NH$_3$ in MeOH). Fractions #10-22 were combined and concentrated under reduced pressure to give 1-(4-((1,5-naphthyridin-2-yl)methoxy)phenyl)-2-(pyridin-4-yl)ethanone as a pale green solid (104.5 mg, 39.8%). $^1$H NMR (300 MHz, CDCl$_3$) δ 9.00 (dd, J=4.2, 1.6 Hz, 1H), 8.55 (dd, J=4.5, 1.6 Hz, 2H), 8.48-8.43 (m, 1H), 8.39 (ddd, J=8.5, 1.6, 0.9 Hz, 1H), 8.01-7.95 (m, 2H), 7.90-7.86 (m, 1H), 7.68 (dd, J=4.5, 1.5 Hz, 2H), 7.12-7.06 (m, 2H), 5.47 (s, 2H), 4.22 (s, 2H). MS (DCI—NH$_3$) m/z=356 (M+H)$^+$.

Intermediate 4

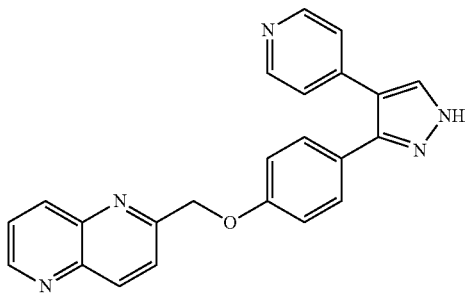

2-((4-(4-(pyridin-4-yl)-1H-pyrazol-3-yl)phenoxy)methyl)-1,5-naphthyridine

In a 5 mL round bottom flask equipped with a magnetic stirbar and a condenser with a calcium sulfate drying tube was stirred at reflux for 18 hours a mixture of Intermediate 4D, 1-(4-((1,5-naphthyridin-2-yl)methoxy)phenyl)-2-(pyridin-4-yl)ethanone (104 mg, 0.293 mmol) and N,N-dimethylformamide dimethyl acetal (1.0 mL, 7.53 mmol). The reaction mixture was checked by TLC (95:5 EtOAc/MeOH). The spot for starting material had been replaced by a lower Rf spot. Volatiles were removed under reduced pressure to give a brown oil, 1-(4-((1,5-naphthyridin-2-yl)methoxy)phenyl)-3-(dimethylamino)-2-(pyridin-4-yl)prop-2-en-1-one (120 mg, 0.292 mmol) that was dissolved in methanol (2.5 mL) and stirred at ambient temperature. Hydrazine monohydrate (0.02127 mL, 0.438 mmol) was added via syringe and the reaction mixture was stirred at reflux for 2 hours. Another 1.5 equivalents of hydrazine monohydrate was added and stirring at reflux was continued an additional 2 hours. Volatiles were removed under reduced pressure to give a tan solid that was rinsed with water 3 times then stirred with $Et_2O$ overnight. The $Et_2O$ was decanted away and the remaining solid was partitioned between $CHCl_3$ and brine. The aqueous layer was extracted once more with $CHCl_3$ and the combined organic layers were dried ($MgSO_4$) and filtered. The filtrate was concentrated under reduced pressure to give a crude, bright yellow solid. This solid was purified by column chromatography on an Analogix IF-280 (Agilent SF15-24 g, 100% DCM to 98:2 DCM/2M $NH_3$ in MeOH). Fractions #5-20 were combined and concentrated under reduced pressure to give a pale yellow solid. The solid was dissolved in warm $CHCl_3$ and the resulting solution was filtered and concentrated under reduced pressure. The solid residue was rinsed with $Et_2O$, then dissolved in a minimum of hot MeOH. The solution was placed in a 0° C. freezer to induce crystallization. Intermediate 4, 2-((4-(4-(pyridin-4-yl)-1H-pyrazol-3-yl)phenoxy)methyl)-1,5-naphthyridine was obtained by filtration as white crystals (16.5 mg, 14.9%). $^1$H NMR (300 MHz, methanol-$d_4$) δ 8.98 (dd, J=4.2, 1.6 Hz, 1H), 8.48 (dd, J=8.6, 1.8 Hz, 2H), 8.36 (dd, J=4.7, 1.6 Hz, 2H), 8.02 (d, J=8.8 Hz, 1H), 7.97 (br s, 1H), 7.82 (dd, J=8.5, 4.3 Hz, 1H), 7.42-7.36 (m, 2H), 7.33 (d, J=5.9 Hz, 2H), 7.16 (d, J=7.3 Hz, 2H), 5.47 (s, 2H). MS (ESI) m/z=380 (M+H)$^+$.

Intermediate 5

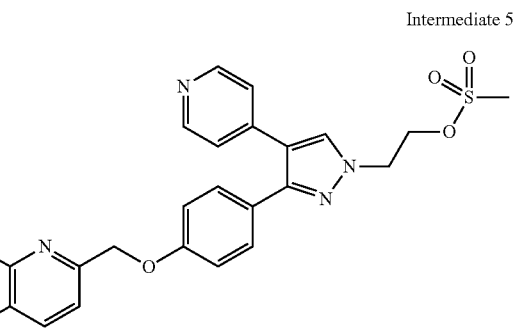

2-(3-(4-((1,5-naphthyridin-2-yl)methoxy)phenyl)-4-(pyridin-4-yl)-1H-pyrazol-1-yl)ethyl methanesulfonate Intermediate 5A

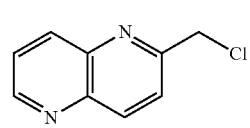

2-(chloromethyl)-1,5-naphthyridine

A mixture of 2-methyl-1,5-naphthyridine (CAS#7675-32-3, Synchem-OHG #CDP146FP1, 998 mg, 6.92 mmol), NCS (1109 mg, 8.31 mmol), and benzoyl peroxide (84 mg, 0.347 mmol) in $CCl_4$ (34 mL) was stirred at reflux for 17 h. The reaction mixture was checked by TLC (100% EtOAc). Volatiles were removed under reduced pressure and the residue was partitioned between EtOAc and saturated aqueous sodium bicarbonate. The organic layer was washed with brine, dried ($MgSO_4$), and filtered. The filtrate was concentrated under reduced pressure and the residue was purified by column chromatography on an Analogix IF-280 (Agilent SF15-24 g, 7:3 to 3:7 hexane/EtOAc). Fractions #7-8 were combined and concentrated under reduced pressure to give the undesired byproduct, 2-(dichloromethyl)-1,5-naphthyridine, as an off-white solid (113 mg, 7.7% yield). Fractions #12-18 were combined and concentrated under reduced pressure to give the desired 2-(chloromethyl)-1,5-naphthyridine as an off-white solid (472 mg, 38.2%). $^1$H NMR (300 MHz, $CDCl_3$) δ 8.99 (dd, J=4.2, 1.6, 1H), 8.45 (d, J=8.8, 1H), 8.38 (ddd, J=8.5, 1.5, 0.8, 1H), 7.85 (d, J=8.7, 1H), 7.66 (dd, J=8.6, 4.2, 1H), 4.86 (s, 2H). MS (DCI—$NH_3$) m/z=179 (M+H)$^+$, m/z=196 (M+$NH_4$)$^+$, m/z=213 (M+$NH_4$+$NH_3$)$^+$.

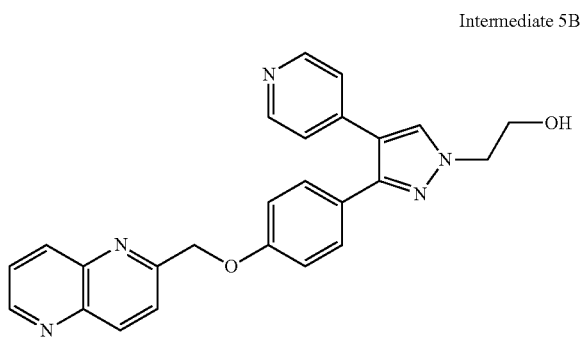 [SMILES: OCCn1cc(-c2ccncc2)c(-c2ccc(OCc3ccc4ncccc4n3)cc2)n1]

Intermediate 5B

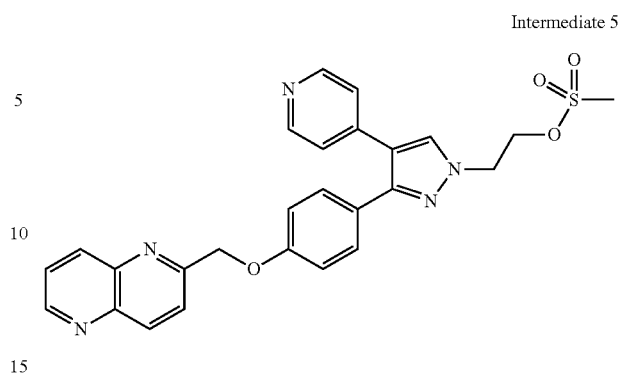

Intermediate 5

2-(3-(4-((1,5-naphthyridin-2-yl)methoxy)phenyl)-4-(pyridin-4-yl)-1H-pyrazol-1-yl)ethanol An oven-dried, 50 mL round bottom flask equipped with a magnetic stirbar was cooled to ambient temperature under a stream of dry nitrogen. The flask was charged with Intermediate 2,4-(1-(2-hydroxyethyl)-4-(pyridin-4-yl)-1H-pyrazol-3-yl)phenol (157 mg, 0.560 mmol) and DMF (4 mL) was added to give a solution. To this stirred solution was added sodium bis(trimethylsilyl)amide, 1.0 M solution in THF (0.560 mL, 0.560 mmol). After stirring for 15 minutes, the reaction mixture was treated dropwise with a solution of Intermediate 5A, 2-(chloromethyl)-1,5-naphthyridine (100 mg, 0.560 mmol) in THF (2 mL). The vial containing this solution was rinsed with DMF (1 mL) and this rinse was also added to the reaction mixture. The reaction mixture was stirred under a dry nitrogen atmosphere at ambient temperature for 2 hours. An aliquot was partitioned between water and EtOAc. The organic layer was checked by TLC (95:5 DCM/2M NH$_3$ in MeOH). A new spot with an Rf intermediate between the two starting materials had formed, although some unreacted starting material was evident. The reaction mixture was stirred an additional 17 h. Volatiles were removed under reduced pressure and the residue was partitioned between CHCl$_3$ and aqueous sodium carbonate. The aqueous layer was extracted once more with CHCl$_3$, then the combined organic layers were washed twice with brine. The CHCl$_3$ layer was dried (MgSO$_4$) and filtered. The filtrate was concentrated under reduced pressure to give a pink solid. The solid was purified by column chromatography on an Analogix IF-280 (Agilent SF15-24 g, 98:2 to 95:5 DCM/2M NH$_3$ in MeOH). Fractions #5-9 were combined and concentrated under reduce pressure to give a pale pink solid that was stored in a vacuum oven at ambient temperature to provide dry 2-(3-(4-((1,5-naphthyridin-2-yl)methoxy)phenyl)-4-(pyridin-4-yl)-1H-pyrazol-1-yl)ethanol (157.8 mg, 66.6%). $^1$H NMR (300 MHz, methanol-d$_4$) δ 8.98 (dd, J=4.2, 1.5 Hz, 1H), 8.51-8.46 (m, 2H), 8.35 (dd, J=4.6, 1.6 Hz, 2H), 8.06 (s, 1H), 8.02 (d, J=8.8 Hz, 1H), 7.82 (dd, J=8.6, 4.3 Hz, 1H), 7.41-7.35 (m, 2H), 7.29 (dd, J=4.6, 1.6 Hz, 2H), 7.15-7.09 (m, 2H), 5.46 (s, 2H), 4.29 (t, J=5.3 Hz, 2H), 3.95 (t, J=5.3 Hz, 2H). MS (DCI—NH$_3$) m/z=424 (M+H)$^+$.

2-(3-(4-((1,5-naphthyridin-2-yl)methoxy)phenyl)-4-(pyridin-4-yl)-1H-pyrazol-1-yl)ethyl methanesulfonate Method 1: A stirred solution of Intermediate 5B, 2-(3-(4-((1,5-naphthyridin-2-yl)methoxy)phenyl)-4-(pyridin-4-yl)-1H-pyrazol-1-yl)ethanol in DCM is cooled at 0° C. Pyridine (12 equivalents) and methanesulfonyl chloride (8 equivalents) are added and the reaction mixture is stirred at 0° C. for 1 h. The mixture is quenched with water and extracted with more DCM. The organic solvent is separated, dried (MgSO$_4$), and concentrated under reduced pressure. The crude residue is purified by silica gel column chromatography. The desired fractions are collected and concentrated under reduced pressure to yield 2-(3-(4-((1,5-naphthyridin-2-yl)methoxy)phenyl)-4-(pyridin-4-yl)-1H-pyrazol-1-yl)ethyl methanesulfonate.

Method 2: A solution of Intermediate 5B, 2-(3-(4-((1,5-naphthyridin-2-yl)methoxy)phenyl)-4-(pyridin-4-yl)-1H-pyrazol-1-yl)ethanol in DCM stirred at 0° C. Pyridine (11 equivalents) is added to the reaction mixture followed by methanesulfonic anhydride (8 equivalents) and stirring is continued for 4 h at 0° C. The solvent is evaporated by flushing with nitrogen then the crude mixture is redissolved in MeOH, diluted with water, and purified by solid phase extraction. Residual water is removed by azeotropic distillation with MeCN, and the mixture is dried overnight in a vacuum oven at ambient temperature.

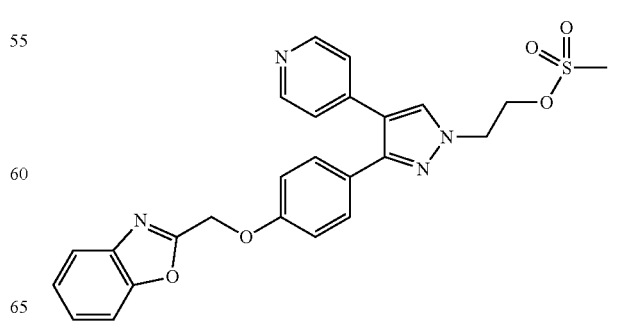

Intermediate 6

2-(3-(4-(benzo[d]oxazol-2-ylmethoxy)phenyl)-4-(pyridin-4-yl)-1H-pyrazol-1-yl)ethyl methanesulfonate Intermediate 6A

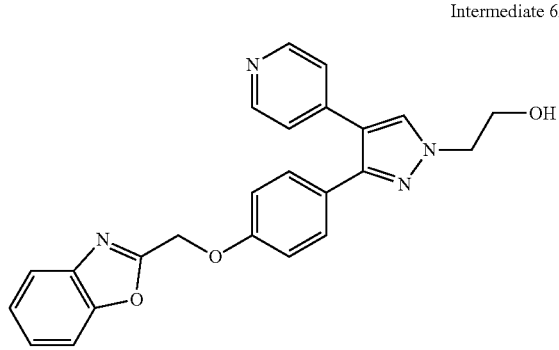

2-(3-(4-(benzo[d]oxazol-2-ylmethoxy)phenyl)-4-(pyridin-4-yl)-1H-pyrazol-1-yl)ethanol A mixture of Intermediate 2,4-(1-(2-hydroxyethyl)-4-(pyridin-4-yl)-1H-pyrazol-3-yl)phenol (84 mg, 0.298 mmol) in DMF (2 mL) was stirred under dry nitrogen while chilling to 0° C. Sodium bis(trimethylsilyl)amide, 1.0 M solution in THF (0.298 mL, 0.298 mmol) was added to the reaction mixture, resulting in formation of a precipitate. The ice/water bath was removed and the reaction mixture was stirred for 15 minutes as much of the precipitate dissolved. A solution of 2-(chloromethyl)benzo[d]oxazole (CA S#41014-43-1, Bionet #12Y-0817, 50 mg, 0.298 mmol) in THF (1 mL) was then added dropwise to the reaction mixture, turning it a deep purple color. When the addition was complete, the reaction mixture was stirred at 40° C. for 30 minutes. TLC (95:5 DCM/2M NH$_3$ in MeOH) indicated that a higher Rf spot had formed so the reaction mixture was diluted with aqueous sodium carbonate and extracted with EtOAc. The organic layer was washed with brine, dried (MgSO$_4$), and filtered. The filtrate was concentrated under reduced pressure to give a golden oil. The oil was purified by column chromatography on an Analogix IF-280 (Agilent SF10-4 g, 100% DCM to 98:2 DCM/2M NH$_3$ in MeOH). Fractions #13-17 were combined and concentrated under reduced pressure to give 2-(3-(4-(benzo[d]oxazol-2-ylmethoxy)phenyl)-4-(pyridin-4-yl)-1H-pyrazol-1-yl)ethanol as an off-white solid (79 mg, 64.2%). $^1$H NMR (300 MHz, methanol-d$_4$) δ 8.34 (dd, J=4.6, 1.6 Hz, 2H), 8.06 (s, 1H), 7.76-7.69 (m, 1H), 7.68-7.61 (m, 1H), 7.48-7.35 (m, 4H), 7.28 (dd, J=4.6, 1.6 Hz, 2H), 7.15-7.09 (m, 2H), 5.43 (s, 2H), 4.28 (t, J=5.3 Hz, 2H), 3.95 (t, J=5.3 Hz, 2H). MS (ESI+) m/z=413 (M+H)$^+$.

Intermediate 6

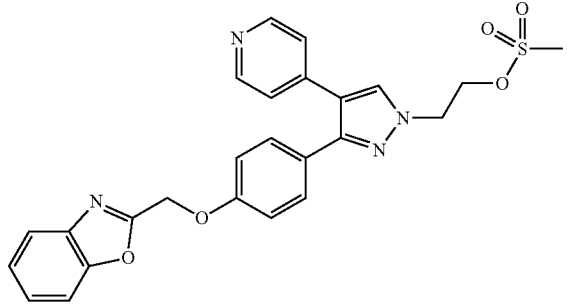

2-(3-(4-(benzo[d]oxazol-2-ylmethoxy)phenyl)-4-(pyridin-4-yl)-1H-pyrazol-1-yl)ethyl methanesulfonate Intermediate 6 is prepared by the methods described for the final step leading to Intermediate 5, substituting Intermediate 6A, 2-(3-(4-(benzo[d]oxazol-2-ylmethoxy)phenyl)-4-(pyridin-4-yl)-1H-pyrazol-1-yl)ethanol in place of Intermediate 5B.

Intermediate 7

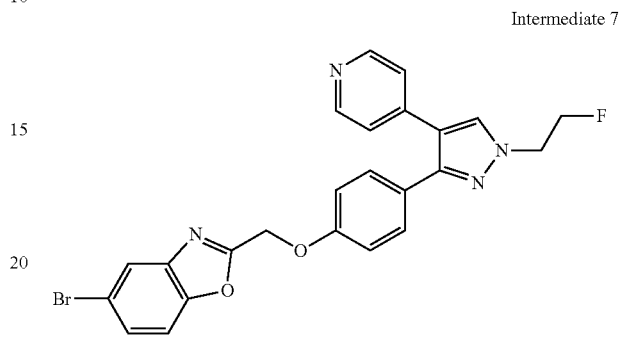

5-bromo-2-((4-(1-(2-fluoroethyl)-4-(pyridin-4-yl)-1H-pyrazol-3-yl)phenoxy)methyl)benzo[d]oxazole A mixture of Intermediate 3,4-(1-(2-fluoroethyl)-4-(pyridin-4-yl)-1H-pyrazol-3-yl)phenol (57 mg, 0.201 mmol) and cesium carbonate (197 mg, 0.604 mmol) in DMF (2 mL) was stirred at ambient temperature under a dry nitrogen atmosphere for 15 minutes. A solution of 5-bromo-2-(chloromethyl)benzo[d]oxazole (CAS#110704-48-8, Bionet #GC-0713, 54.6 mg, 0.221 mmol) in THF (0.5 mL) was added dropwise to the reaction mixture. When the addition was complete the reaction mixture was stirred at ambient temperature for 74 hours. The reaction mixture was diluted with water and extracted with EtOAc (3×30 mL). The combined organic layers were washed with brine (2×50 mL), then dried over MgSO$_4$. The drying agent was removed by filtration and the filtrate was concentrated under reduced pressure to give a golden oil that was purified by column chromatography on an Analogix IF-280 (Agilent SF15-24 g, 100% DCM to 96:4 DCM/2M NH$_3$ in MeOH). Fractions #7-14 were combined and concentrated under reduced pressure to give 5-bromo-2-((4-(1-(2-fluoroethyl)-4-(pyridin-4-yl)-1H-pyrazol-3-yl)phenoxy)methyl)benzo[d]oxazole as a white solid (53.1 mg, 53.5%). $^1$H NMR (300 MHz, methanol-d$_4$) δ 8.36 (d, J=6.0, 2H), 8.09 (s, 1H), 7.90 (dd, J=1.6, 0.7, 1H), 7.63-7.55 (m, 2H), 7.43-7.36 (m, 2H), 7.29 (dd, J=4.7, 1.6, 2H), 7.15-7.09 (m, 2H), 5.43 (s, 2H), 4.81 (dt, J=47.1, 4.7, 2H), 4.51 (dt, J=26.6, 4.9, 1H). MS (DCI—NH$_3$) m/z=493 (M+H)$^+$.

Intermediate 8

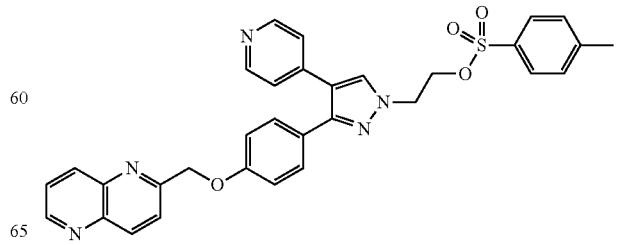

2-(3-(4-((1,5-naphthyridin-2-yl)methoxy)phenyl)-4-(pyridin-4-yl)-1H-pyrazol-1-yl)ethyl 4-methylbenzenesulfonate An oven-dried, 25 mL round bottom flask, equipped with a magnetic stirbar, was cooled to ambient temperature under a stream of dry nitrogen. The flask was charged with Intermediate 5B, 2-(3-(4-((1,5-naphthyridin-2-yl)methoxy)phenyl)-4-(pyridin-4-yl)-1H-pyrazol-1-yl)ethanol (134.5 mg, 0.318 mmol) and p-toluenesulfonic anhydride (114 mg, 0.349 mmol). DCM (3 mL) was added to give a solution that was stirred while cooling with an ice/water bath. Triethylamine (0.0531 mL, 0.381 mmol) was added by syringe and the reaction mixture turned a red-orange color. Stirring at 0° C. was continued for 10 minutes, then the ice/water bath was removed and the reaction mixture was allowed to reach ambient temperature. The reaction mixture was stirred at ambient temperature for 5 hours. The reaction mixture was diluted with DCM and washed with water. The organic layer was then washed with dilute aqueous sodium bicarbonate solution. The organic layer was dried (MgSO$_4$) and filtered. The filtrate was concentrated under reduced pressure to give a pink solid that was purified by column chromatography on an Analogix IF-280 (Agilent SF15-24 g, 100% EtOAc to 50:50 EtOAc/acetonitrile). Fractions #1-36 were combined and concentrated under reduced pressure to give a white solid that was stored overnight under a stream of dry nitrogen. The solid was dissolved in DCM and the mixture was filtered. The filtrate was transferred to a tared, 4 mL screw cap vial. Solvent was evaporated to provide a white solid (158 mg, 86% yield). NMR and MS of this solid indicated that there was some minor contamination by the N-vinyl-pyrazole byproduct resulting from elimination. This white solid was dissolved in hot EtOAc. Treatment with Et$_2$O caused some oiling out. The solution was decanted away and partially concentrated to give 2-(3-(4-((1,5-naphthyridin-2-yl)methoxy)phenyl)-4-(pyridin-4-yl)-1H-pyrazol-1-yl)ethyl 4-methylbenzenesulfonate as a white solid (67.5 mg, 36.9%) that was collected by filtration and rinsed with Et$_2$O, NMR indicated that the compound was pure with no sign of the N-vinyl-pyrazole contaminant being present. $^1$H NMR (300 MHz, CDCl$_3$) δ 8.99 (dd, J=4.2, 1.6 Hz, 1H), 8.50 (s, 2H), 8.44 (d, J=8.8 Hz, 1H), 8.38 (ddd, J=8.5, 1.5, 0.7 Hz, 1H), 7.93 (d, J=8.8 Hz, 1H), 7.69-7.64 (m, 2H), 7.60 (s, 1H), 7.33-7.28 (m, 2H), 7.22 (d, J=8.0 Hz, 2H), 7.15 (d, J=4.9 Hz, 2H), 7.03-6.98 (m, 2H), 5.43 (s, 2H), 4.47-4.39 (m, 4H), 2.32 (s, 3H). MS (+ESI) m/z=578 (M+H)$^+$.

2-(3-(4-(benzo[d]oxazol-2-ylmethoxy)phenyl)-4-(pyridin-4-yl)-1H-pyrazol-1-yl)ethyl 4-methylbenzenesulfonate A stirred solution of 2-(3-(4-(benzo[d]oxazol-2-ylmethoxy)phenyl)-4-(pyridin-4-yl)-1H-pyrazol-1-yl)ethanol (71 mg, 0.172 mmol) and p-toluenesulfonic anhydride (61.8 mg, 0.189 mmol) in DCM (1.5 mL) in a 4 mL screw cap vial under a dry nitrogen atmosphere was chilled with an ice/water bath. To this stirred reaction mixture was added triethylamine (0.0288 mL, 0.207 mmol) via syringe. The reaction mixture was stirred at 0° C. for 10 minutes, then the ice/water bath was removed and stirring was continued at ambient temperature for 4.5 hours. A TLC check (80:20 CHCl$_3$/CH$_3$CN) indicated that a higher Rf spot had formed. The reaction mixture was washed with water and then with aqueous sodium bicarbonate solution. After a brine wash, the organic layer was dried (MgSO$_4$) and filtered. The filtrate was concentrated under reduced pressure and the residue was purified by column chromatography on an Analogix IF-280 (Agilent SF15-12 g, 60:40 CHCl$_3$/acetonitrile). Fractions #3-8 were combined and concentrated under reduced pressure to give a white solid that was crystallized from EtOAc/Et$_2$O. Two crystal batches were combined to provide 2-(3-(4-(benzo[d]oxazol-2-ylmethoxy)phenyl)-4-(pyridin-4-yl)-1H-pyrazol-1-yl)ethyl 4-methylbenzenesulfonate as white crystals (44 mg, 45%). $^1$H NMR (300 MHz, CDCl$_3$) δ 8.50 (d, J=4.2 Hz, 2H), 7.79-7.73 (m, 1H), 7.69-7.64 (m, 2H), 7.60 (s, 1H), 7.59-7.54 (m, 1H), 7.42-7.34 (m, 2H), 7.34-7.29 (m, 2H), 7.22 (d, J=8.1 Hz, 2H), 7.14 (d, J=5.5 Hz, 2H), 7.07-7.01 (m, 2H), 5.35 (s, 2H), 4.47 4.39 (m, 4H), 2.32 (s, 3H). MS (+ESI) m/z=567 (M+H)$^+$.

Intermediate 10

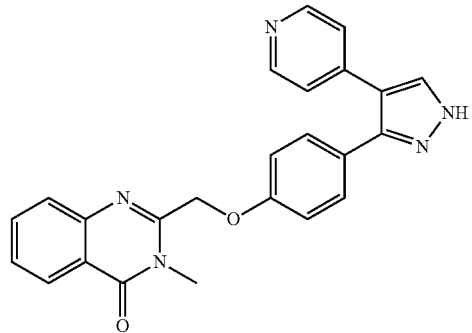

3-methyl-2-((4-(4-(pyridin-4-yl)-1H-pyrazol-3-yl)phenoxy)methyl)quinazolin-4(3H)-one Intermediate 10A

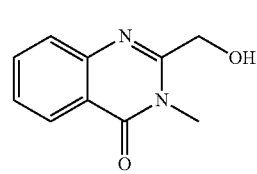

2-(hydroxymethyl)-3-methylquinazolin-4(3H)-one

The title compound is prepared by the method published in *Journal of Organic Chemistry* 1964, 29, 582-584 (see compound IVa).

Intermediate 9

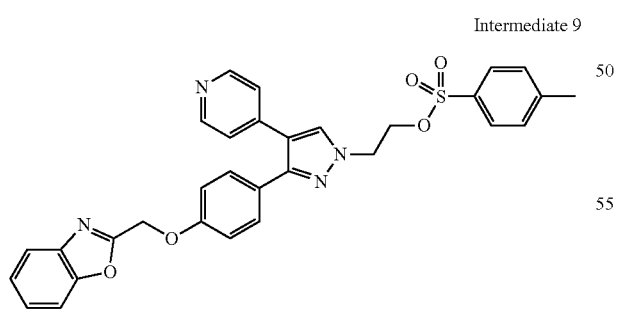

Intermediate 10B

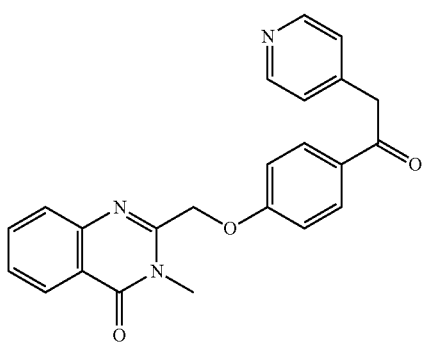

3-methyl-2-((4-(2-(pyridin-4-yl)acetyl)phenoxy)methyl)quinazolin-4(3H)-one

The title compound is prepared by the method of Intermediate 4D, substituting Intermediate 10A, 2-(hydroxymethyl)-3-methylquinazolin-4(3H)-one, in place of Intermediate 4C, (1,5-naphthyridin-2-yl)methanol.

Intermediate 10

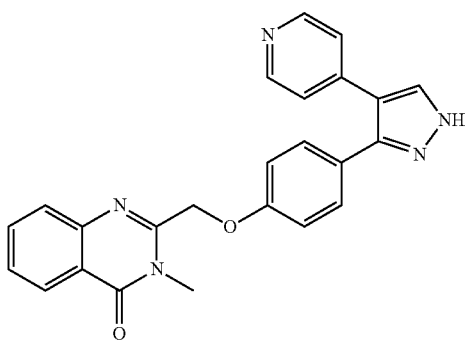

3-methyl-2-((4-(4-(pyridin-4-yl)-1H-pyrazol-3-yl)phenoxy)methyl)quinazolin-4(3H)-one The title compound is prepared by the method of Intermediate 4, substituting Intermediate 10B, 3-methyl-2-((4-(2-(pyridin-4-yl)acetyl)phenoxy)methyl)-quinazolin-4(3H)-one, in place of Intermediate 4D, 1-(4-(((1,5-naphthyridin-2-yl)methoxy)phenyl)-2-(pyridin-4-yl)ethanone.

Intermediate 11

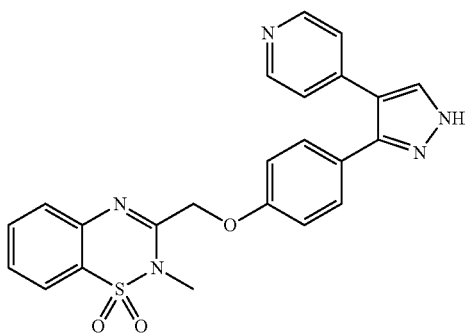

1,1-dioxo-2-methyl-3-((4-(4-(pyridin-4-yl)-1H-pyrazol-3-yl)phenoxy)methyl)-2H-benzo[e][1,2,4]thiadiazine Intermediate 11A

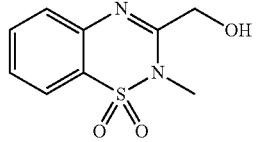

(1,1-dioxo-2-methyl-2H-benzo[e][1,2,4]thiadiazin-3-yl)methanol

The title compound is prepared by a two step procedure.
Step 1: N-methylation of a DMF solution of methyl 1,1-dioxo-2H-benzo[e][1,2,4]thiadiazine-3-carboxylate (CAS#1251923-55-3, Enamine #EN300-64179) by iodomethane in the presence of a base such as NaN(TMS)₂ or Cs₂CO₃ provides methyl 1,1-dioxo-2-methyl-2H-benzo[e][1,2,4]thiadiazine-3-carboxylate.
Step 2: Reduction of methyl 1,1-dioxo-2-methyl-2H-benzo[e][1,2,4]thiadiazine-3-carboxylate with a reducing agent such as LAH or NaBH₄ provides Intermediate 11A, (1,1-dioxo-2-methyl-2H-benzo[e][1,2,4]thiadiazin-3-yl)methanol.

Intermediate 11B

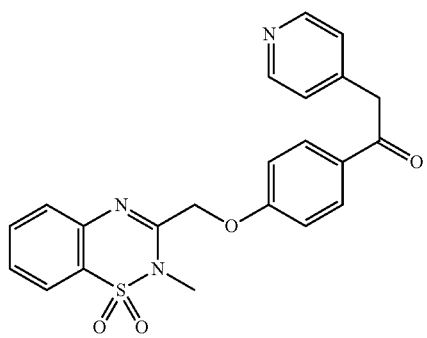

1-(4-(((1,1-dioxo-2-methyl-2H-benzo[e][1,2,4]thiadiazin-3-yl)methoxy)phenyl)-2-(pyridin-4-yl)ethanone The title compound is prepared by the method of Intermediate 4D, substituting Intermediate 11A, (1,1-dioxo-2-methyl-2H-benzo[e][1,2,4]thiadiazin-3-yl)methanol, in place of Intermediate 4C, (1,5-naphthyridin-2-yl)methanol.

Intermediate 11

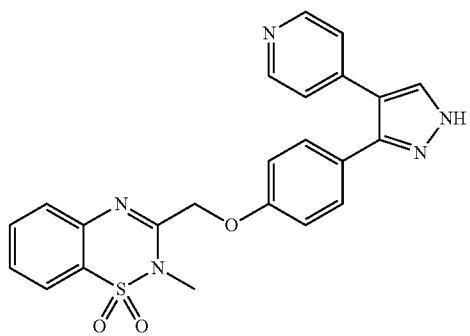

1,1-dioxo-2-methyl-3-((4-(4-(pyridin-4-yl)-1H-pyrazol-3-yl)phenoxy)methyl)-2H-benzo[e][1,2,4]thiadiazine The title compound is prepared by the method of Intermediate 4, substituting Intermediate 11B, 1-(4-((1,1-dioxo-2-methyl-2H-benzo[e][1,2,4]thiadiazin-3-yl)methoxy)phenyl)-2-(pyridin-4-yl)ethanone, in place of Intermediate 4D, 1-(4-((1,5-naphthyridin-2-yl)methoxy)phenyl)-2-(pyridin-4-yl)ethanone.

Intermediate 12

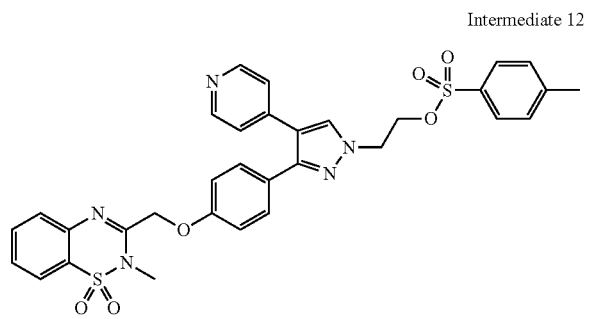 [SMILES: Cc1ccc(S(=O)(=O)OCCn2cc(-c3ccncc3)c(-c3ccc(OCC4=Nc5ccccc5S(=O)(=O)N4C)cc3)n2)cc1]

2-(3-(4-((1,1-dioxo-2-methyl-2H-benzo[e][1,2,4]thiadiazin-3-yl)methoxy)phenyl)-4-(pyridin-4-yl)-1H-pyrazol-1-yl)ethyl 4-methylbenzenesulfonate Intermediate 12A

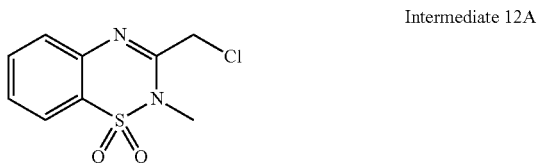

1,1-dioxo-3-(chloromethyl)-2-methyl-2H-benzo[e][1,2,4]thiadiazine

The title compound is prepared by diazomethane methylation of 1,1-dioxo-3-(chloromethyl)-2H-benzo[e][1,2,4]thiadiazine (CAS#37162-65-5, Enamine #EN300-62803) by the method published in *Farmaco, Edicione Scientifica* 1966, 21, 430-442 (see compound XVI).

Intermediate 12B

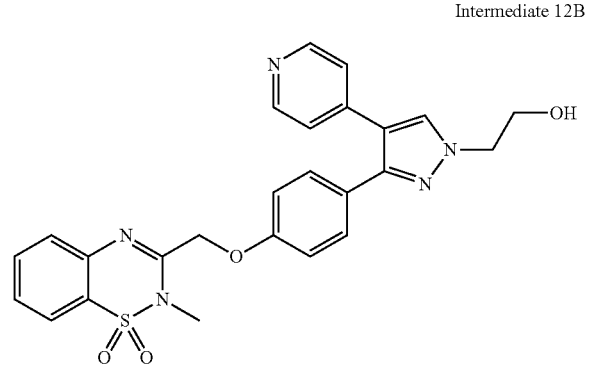 [SMILES: CN1C(COc2ccc(-c3nn(CCO)cc3-c3ccncc3)cc2)=Nc2ccccc2S1(=O)=O]

2-(3-(4-((1,1-dioxo-2-methyl-2H-benzo[e][1,2,4]thiadiazin-3-yl)methoxy)phenyl)-4-(pyridin-4-yl)-1H-pyrazol-1-yl)ethanol The title compound is prepared by the method of Intermediate 5B, substituting Intermediate 12A, 1,1-dioxo-3-(chloromethyl)-2-methyl-2H-benzo[e][1,2,4]thiadiazine in place of Intermediate 5A, 2-(chloromethyl)-1,5-naphthyridine.

Intermediate 12

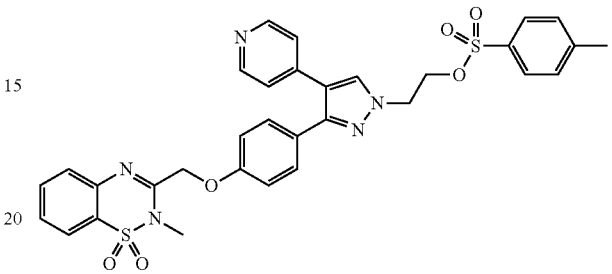

2-(3-(4-((1,1-dioxo-2-methyl-2H-benzo[e][1,2,4]thiadiazin-3-yl)methoxy)phenyl)-4-(pyridin-4-yl)-1H-pyrazol-1-yl)ethyl 4-methylbenzenesulfonate The title compound is prepared by the method of Intermediate 8, substituting Intermediate 12B, 2-(3-(4-((1,1-dioxo-2-methyl-2H-benzo[e][1,2,4]thiadiazin-3-yl)methoxy)phenyl)-4-(pyridin-4-yl)-1H-pyrazol-1-yl)ethanol, in place of Intermediate 5B, 2-(3-(4-((1,5-naphthyridin-2-yl)methoxy)phenyl)-4-(pyridin-4-yl)-1H-pyrazol-1-yl)ethanol.

Intermediate 13

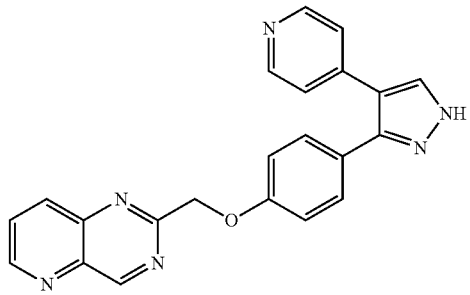

2-((4-(4-(pyridin-4-yl)-1H-pyrazol-3-yl)phenoxy)methyl)pyrido[3,2-d]pyrimidine Intermediate 13A

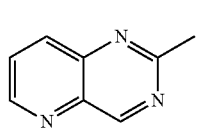

2-methylpyrido[3,2-d]pyrimidine

Dechlorination of 4-chloro-2-methylpyrido[3,2-d]pyrimidine (CAS#56128-29-1, HDH Pharma, Inc. #16414) by hydrogenolysis in the presence of catalytic Pd/C provides 2-methylpyrido[3,2-d]pyrimidine.

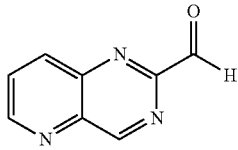

Intermediate 13B pyrido[3,2-d]pyrimidine-2-carbaldehyde

Oxidation with selenium dioxide by the method of Intermediate 4B, substituting 2-methylpyrido[3,2-d]pyrimidine, in place of 2-methyl-1,5-naphthyridine provides pyrido[3,2-d]pyrimidine-2-carb aldehyde.

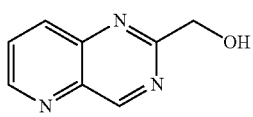

Intermediate 13C pyrido[3,2-d]pyrimidin-2-ylmethanol

Reduction with sodium borohydride by the method of Intermediate 4C, substituting pyrido[3,2-d]pyrimidine-2-carbaldehyde, in place of Intermediate 4B, 1,5-naphthyridine-2-carbaldehyde provides pyrido[3,2-d]pyrimidin-2-ylmethanol.

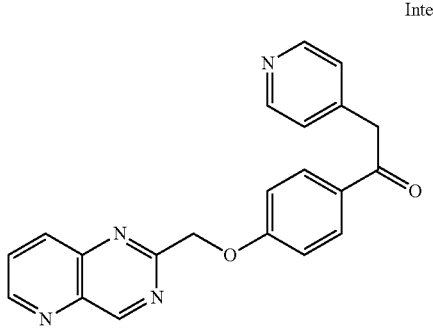

Intermediate 13D 2-(pyridin-4-yl)-1-(4-(pyrido[3,2-d]pyrimidin-2-ylmethoxy)phenyl)ethanone The title compound is prepared by the method of Intermediate 4D, substituting Intermediate 13C, pyrido[3,2-d]pyrimidin-2-ylmethanol, in place of Intermediate 4C, (1,5-naphthyridin-2-yl)methanol.

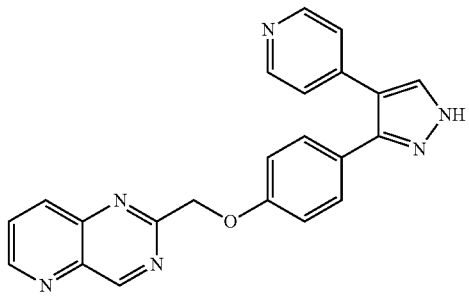

Intermediate 13

2-((4-(4-(pyridin-4-yl)-1H-pyrazol-3-yl)phenoxy)methyl)pyrido[3,2-d]pyrimidine

The title compound is prepared by the method of Intermediate 4, substituting Intermediate 13D, 2-(pyridin-4-yl)-1-(4-(pyrido[3,2-d]pyrimidin-2-ylmethoxy)phenyl)ethanone, in place of Intermediate 4D, 1-(4-((1,5-naphthyridin-2-yl)methoxy)phenyl)-2-(pyridin-4-yl)ethanone.

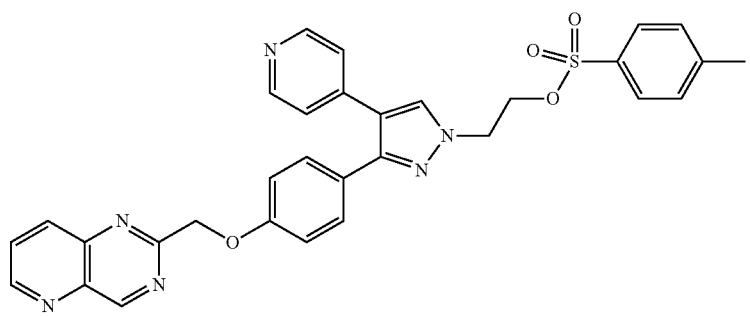

Intermediate 14

2-(4-(pyridin-4-yl)-3-(4-(pyrido[3,2-d]pyrimidin-2-ylmethoxy)phenyl)-1H-pyrazol-1-yl)ethyl 4-methyl-benzenesulfonate Intermediate 14A

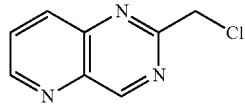

2-(chloromethyl)pyrido[3,2-d]pyrimidine

The title compound is prepared by the method of Intermediate 5A substituting Intermediate 13A, 2-methylpyrido[3,2-d]pyrimidine, in place of 2-methyl-1,5-naphthyridine.

Intermediate 14B

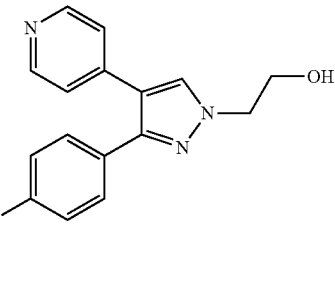

2-(4-(pyridin-4-yl)-3-(4-(pyrido[3,2-d]pyrimidin-2-ylmethoxy)phenyl)-1H-pyrazol-1-yl)ethanol The title compound is prepared by the method of Intermediate 5B, substituting Intermediate 14A, 2-(chloromethyl)pyrido[3,2-d]pyrimidine, in place of Intermediate 5A, 2-(chloromethyl)-1,5-naphthyridine.

Intermediate 14

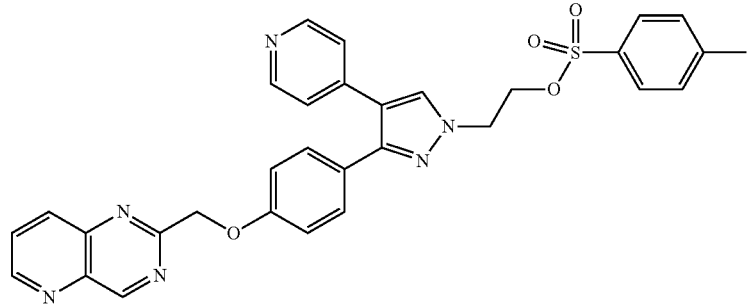

2-(4-(pyridin-4-yl)-3-(4-(pyrido[3,2-d]pyrimidin-2-ylmethoxy)phenyl)-1H-pyrazol-1-yl)ethyl 4-methyl-benzenesulfonate The title compound is prepared by the method of Intermediate 8, substituting Intermediate 14B, 2-(4-(pyridin-4-yl)-3-(4-(pyrido[3,2-d]pyrimidin-2-ylmethoxy)phenyl)-1H-pyrazol-1-yl)ethanol, in place of Intermediate 5B, 2-(3-(4-((1,5-naphthyridin-2-yl)methoxy)phenyl)-4-(pyridin-4-yl)-1H-pyrazol-1-yl)ethanol.

Intermediate 15

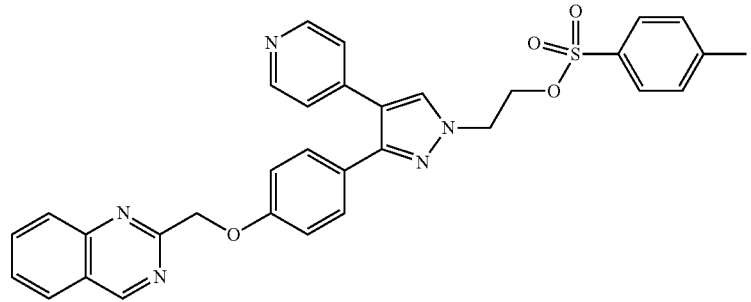

2-(4-(pyridin-4-yl)-3-(4-(quinazolin-2-ylmethoxy) phenyl)-1H-pyrazol-1-yl)ethyl 4-methylbenzenesulfonate

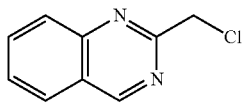

Intermediate 15A

2-(chloromethyl)quinazoline

The title compound was prepared by the method described in *Journal of the Chemical Society, C. Organic* 1966, 234-239.

Step 1: A solution of 2-aminobenzaldehyde (0.969 g, 8 mmol) and pyridine (1.618 mL, 20.00 mmol) in benzene (8 mL) was stirred at 5° C. under a dry nitrogen atmosphere. A solution of chloroacetyl chloride (0.765 mL, 9.60 mmol) in benzene (4 mL) was added dropwise to the reaction mixture. When the addition was complete, the reaction mixture was allowed to warm to 20° C., then was stirred at that temperature for 15 minutes. The reaction mixture was then washed with water (3×20 mL). The combined aqueous layers were extracted once with EtOAc (15 mL). The combined organic layers were dried ($Na_2SO_4$) and filtered. The filtrate was concentrated under reduced pressure to give a pale yellow solid. The solid was checked by TLC (9:1 hexane/EtOAc). A new spot with Rf lower than the starting material was evident. The crude solid was treated with THF/$Et_2O$ to provide the intermediate, 2-chloro-N-(2-formylphenyl)acetamide, as an off-white solid (892 mg, 56.4%) that was collected by filtration. $^1$H NMR (300 MHz, $d_6$-DMSO) δ 11.43 (s, 1H), 10.01 (s, 1H), 8.32 (d, J=8.2 Hz, 1H), 7.94 (dd, J=7.7, 1.6 Hz, 1H), 7.76-7.69 (m, 1H), 7.39 (dt, J=7.5, 1.0 Hz, 1H), 4.47 (s, 2H). MS (DCI—$NH_3$) m/z=198 (M+H)$^+$, m/z=215 (M+$NH_4$)$^+$, m/z=232 (M+$NH_4$+$NH_3$)$^+$.

Step 2: The product of the first step, 2-chloro-N-(2-formylphenyl)acetamide (0.869 g, 4.40 mmol) and ammonia, 7N solution in methanol (4.4 mL, 30.8 mmol) were stirred together at ambient in a sealed tube for 4.5 hours. A TLC (9:1 hexane EtOAc) check indicated that a new lower Rf spot had formed, however, plenty of starting material remained so stirring at ambient temperature was continued for another 19.5 hours, during which time a white precipitate had formed. Volatiles were removed under reduced pressure to give a beige solid that was treated with $CHCl_3$. The portion that was soluble was checked by TLC (7:3 hexane/EtOAc). The major spot in the $CHCl_3$-soluble portion was a new one with lower Rf than the starting material. The $CHCl_3$ mixture was placed in the 0° C. freezer over the weekend. Insoluble material was removed by filtration and the filtrate was concentrated under reduced pressure. The residue was purified by column chromatography on an Analogix IF-280 (Agilent SF10-4 g, 100% $CHCl_3$). The product eluted in fractions #1-10. The product fractions were combined and concentrated under reduced pressure to give 2-(chloromethyl)quinazoline as a white solid (418 mg, 53.2%). $^1$H NMR (300 MHz, $CDCL_3$) δ 9.45 (s, 1H), 8.09 8.04 (m, 1H), 7.99-7.92 (m, 2H), 7.70 (ddd, J=8.0, 6.9, 1.2 Hz, 1H), 4.92 (s, 2H).

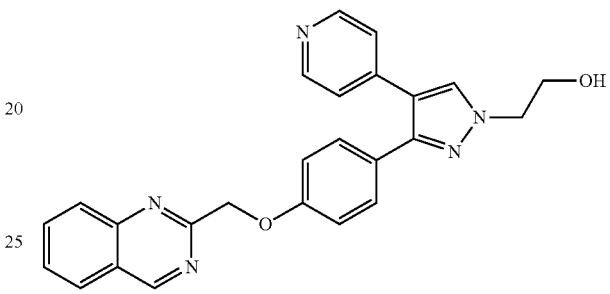

Intermediate 15B

2-(4-(pyridin-4-yl)-3-(4-(quinazolin-2-ylmethoxy) phenyl)-1H-pyrazol-1-yl)ethanol The title compound is prepared by the method of Intermediate 5B, substituting Intermediate 15A, 2-(chloromethyl)quinazoline, in place of Intermediate 5A, 2-(chloromethyl)-1,5-naphthyridine.

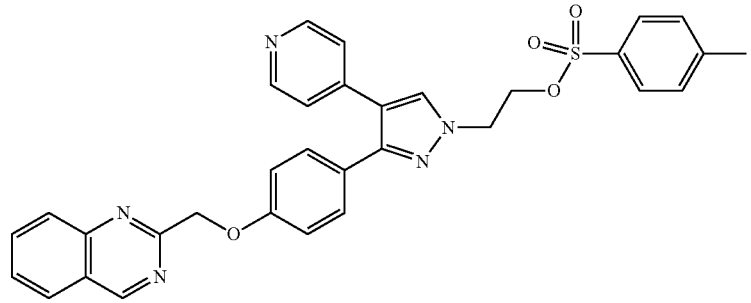

Intermediate 15

2-(4-(pyridin-4-yl)-3-(4-(quinazolin-2-ylmethoxy) phenyl)-1H-pyrazol-1-yl)ethyl 4-methylbenzenesulfonate The title compound is prepared by the method of Intermediate 8, substituting Intermediate 15B, 2-(4-(pyridin-4-yl)-3-(4-(quinazolin-2-ylmethoxy)phenyl)-1H-pyrazol-1-yl)ethanol, in place of Intermediate 5B, 2-(3-(4-((1,5-naphthyridin-2-yl)methoxy)phenyl)-4-(pyridin-4-yl)-1H-pyrazol-1-yl)ethanol.

Example 1

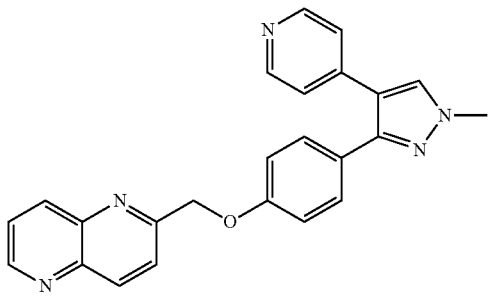 [SMILES: Cn1cc(-c2ccncc2)c(-c2ccc(OCc3ccc4ncccc4n3)cc2)n1]

2-((4-(1-methyl-4-(pyridin-4-yl)-1H-pyrazol-3-yl)phenoxy)methyl)-1,5-naphthyridine A stirred solution of Intermediate 1,4-(1-methyl-4-(pyridin-4-yl)-1H-pyrazol-3-yl)phenol (126 mg, 0.50 mmol) in DMF (3 mL) under a dry nitrogen atmosphere was treated with sodium bis(trimethylsilyl)amide, 1.0M solution in THF (0.550 mL, 0.550 mmol). The reaction mixture was stirred at ambient temperature for 10 minutes, then a solution of Intermediate 5A, 2-(chloromethyl)-1,5-naphthyridine (107 mg, 0.600 mmol) in THF (2 mL) was added dropwise via syringe. The reaction mixture was stirred at ambient temperature for 17 hours. An aliquot was partitioned between EtOAc and water. The organic layer was checked by TLC (95:5 DCM/2M NH$_3$ in MeOH). A faint spot for the starting phenol remained, but the prominent spot with Rf higher than the starting phenol was evident. The reaction mixture was diluted with aqueous sodium carbonate and extracted with EtOAc (2×30 mL). The combined organic layers were then washed with brine (2×60 mL), dried (MgSO$_4$), and filtered. The filtrate was concentrated under reduced pressure and the residue was purified by column chromatography on an Analogix IF-280 (Varian SF25-80 g, 99:1 to 96:4 DCM/2M NH$_3$ in MeOH). Fractions #16-37 were combined and concentrated under reduced pressure. The residue was dissolved in DCM and the resulting solution was filtered. The filtrate was concentrated under reduced pressure to give 2-((4-(1-methyl-4-(pyridin-4-yl)-1H-pyrazol-3-yl)phenoxy)methyl)-1,5-naphthyridine as a white solid (150 mg, 76%). $^1$H NMR (300 MHz, methanol-d$_4$) δ 8.97 (dd, J=4.3, 1.6 Hz, 1H), 8.50-8.45 (m, 2H), 8.35 (dd, J=4.6, 1.6 Hz, 2H), 8.02 (d, J=9.0 Hz, 1H), 8.00 (s, 1H), 7.81 (dd, J=8.5, 4.3 Hz, 1H), 7.39-7.34 (m, 2H), 7.28 (dd, J=4.6, 1.7 Hz, 2H), 7.14-7.08 (m, 2H), 5.45 (s, 2H), 3.96 (s, 3H). MS (DCI—NH$_3$) m/z=394 (M+H)$^+$.

Example 2

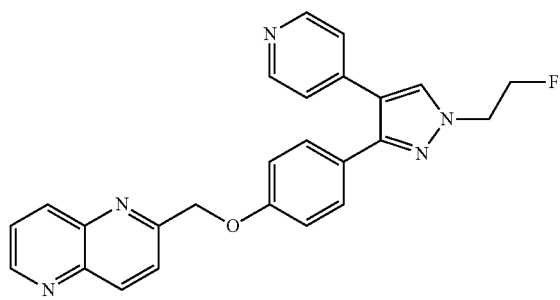 [SMILES: FCCn1cc(-c2ccncc2)c(-c2ccc(OCc3ccc4ncccc4n3)cc2)n1]

2-((4-(1-(2-fluoroethyl)-4-(pyridin-4-yl)-1H-pyrazol-3-yl)phenoxy)methyl)-1,5-naphthyridine A solution of Intermediate 3,4-(1-(2-fluoroethyl)-4-(pyridin-4-yl)-1H-pyrazol-3-yl)phenol (142 mg, 0.5 mmol) in DMF (2 mL) was stirred at 0° C. under a dry nitrogen atmosphere. Sodium bis(trimethylsilyl)amide, 1.0M solution in THF (0.525 mL, 0.525 mmol) was added dropwise to the cold reaction mixture. After stirring at 0° C. for 5 minutes, the reaction mixture was treated dropwise with a solution of Intermediate 5A, 2-(chloromethyl)-1,5-naphthyridine (107 mg, 0.600 mmol) in THF (1 mL). When the addition was complete, the ice/water bath was removed and the reaction mixture was stirred at ambient temperature for 2 hours. A TLC (95:5 DCM/2M NH$_3$ in MeOH) check of the reaction mixture indicated that the starting phenol had been replaced by a major spot with higher Rf. The reaction mixture was partitioned between aqueous sodium carbonate and EtOAc. The aqueous layer was extracted once more with EtOAc, then the combined organic layers were washed twice with brine, dried (MgSO$_4$), and filtered. The filtrate was concentrated under reduced pressure to give a crude solid that, according to LC/MS (AA+ method), was a mixture of desired product (ID: 10, RT=1.43 min) and a nearby (ID: 12, RT=1.54) minor contaminant (the N-vinyl-pyrazole derivative of the product, which is the result of base-induced elimination of HF). The crude solid was purified by column chromatography on an Analogix IF-280 (Agilent SF15-24 g, 100% DCM to 98:2 DCM/2M NH$_3$ in MeOH). Fractions #17-27 were combined and concentrated under reduced pressure to give a white solid that consisted of desired product contaminated with the N-vinyl-pyrazole byproduct. The material was repurified with a preparative reverse phase chromatography system in (Waters XBridge Prep C18, 5 μm OBD, 50×100 mm, 95:5 to 5:95 25 mM aqueous ammonium carbonate/CH$_3$CN). Fractions containing pure product were concentrated under reduced pressure to give a white solid that was left on the rotary evaporator for 15 minutes with the bath temperature equal to 60° C. The resulting white solid residue was treated with acetonitrile and residual water was removed via azeotrope on the rotary evaporator. This process was repeated one more time, then the white solid was dissolved in dichloromethane, dried (MgSO$_4$), and filtered. The filtrate was concentrated under reduced pressure to give 2-((4-(1-(2-fluoroethyl)-4-(pyridin-4-yl)-1H-pyrazol-3-yl)phenoxy)methyl)-1,5-naphthyridine as a white solid (132 mg, 62%). $^1$H NMR (300 MHz, methanol-d$_4$) δ 8.97 (dd, J=4.2, 1.5 Hz, 1H), 8.48 (d, J=8.6 Hz, 2H), 8.36 (dd, J=4.7, 1.6 Hz, 2H), 8.09 (s, 1H), 8.02 (d, J=8.8 Hz, 1H), 7.81 (dd, J=8.5, 4.3 Hz, 1H), 7.42-7.35 (m, 2H), 7.29 (dd, J=4.6, 1.6 Hz, 2H), 7.15-7.09 (m, 2H), 5.45 (s, 2H), 4.81 (dt, J=47.1, 4.7 Hz, 2H), 4.50 (dt, J=26.6, 4.7 Hz, 2H). MS (DCI—NH$_3$) m/z=426 (M+H)$^+$.

Example 3

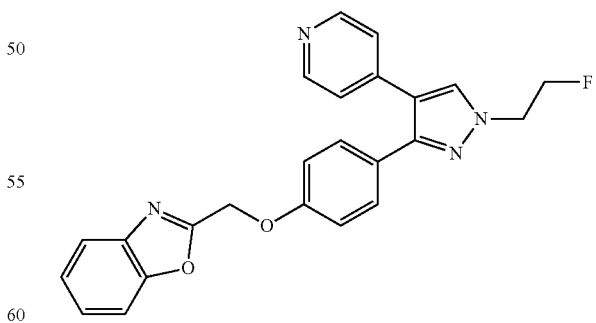

2-((4-(1-(2-fluoroethyl)-4-(pyridin-4-yl)-1H-pyrazol-3-yl)phenoxy)methyl)benzo[d]oxazole A mixture of Intermediate 3,4-(1-(2-fluoroethyl)-4-(pyridin-4-yl)-1H-pyrazol-3-yl)phenol (212 mg, 0.75 mmol) and cesium carbonate (733 mg, 2.250 mmol) in DMF (3.75 mL) was stirred at ambient temperature for 15 minutes. Dropwise addition of a solution of 2-(chloromethyl)benzo[d]oxazole (CAS#41014-43-1, Bionet #12Y-0817, 138 mg, 0.823 mmol) in THF (0.5 mL) to the reaction mixture was followed by stirring at ambient temperature for 16 hours. An aliquot was partitioned between EtOAc and water and the organic layer was checked by TLC (98:2 DCM/2M $NH_3$ in MeOH). The spot for starting phenol was replaced with a higher Rf spot, so the bulk of the reaction mixture was partitioned between EtOAc and water. The organic layer was washed with saturated aqueous sodium carbonate, then washed with brine, then dried ($MgSO_4$), and finally filtered. The filtrate was concentrated under reduced pressure to give a dark brown oil that was purified by column chromatography on an Analogix IF-280 (Varian SF25-80 g, 100% DCM to 98.5:1.5 DCM/2M $NH_3$ in MeOH). Fractions #9-12 were combined and concentrated under reduced pressure and the residue contained product, but also some contaminants. The residue was repurified by column chromatography (Varian SF25-60 g, 99.5:0.5 DCM/2M $NH_3$ in MeOH). Fractions containing pure product (#8-17) were combined and concentrated under reduced pressure to give 2-((4-(1-(2-fluoroethyl)-4-(pyridin-4-yl)-1H-pyrazol-3-yl)phenoxy)methyl)benzo[d]oxazole as a tan solid (124.6 mg, 40.1%). $^1$H NMR (300 MHz, methanol-$d_4$) δ 8.35 (dd, J=4.7, 1.5, 2H), 8.09 (s, 1H), 7.76-7.69 (m, 1H), 7.68-7.61 (m, 1H), 7.48-7.35 (m, 4H), 7.28 (dd, J=4.7, 1.6, 2H), 5.43 (s, 2H), 4.81 (dt, J=47.1, 4.7, 2H), 4.50 (dt, J=26.6, 4.7, 2H). MS (DCI—$NH_3$) m/z=415 (M+H)$^+$.

Example 4

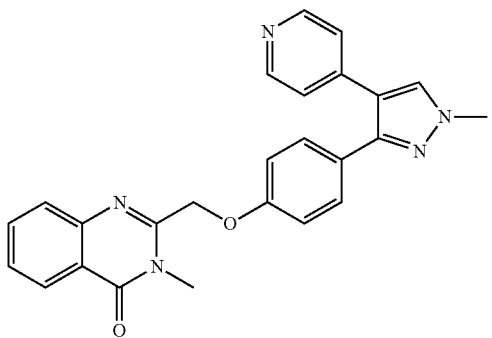 [SMILES: Cn1cc(-c2ccncc2)c(-c2ccc(OCc3nc4ccccc4c(=O)n3C)cc2)n1]

3-methyl-2-((4-(1-methyl-4-(pyridin-4-yl)-1H-pyrazol-3-yl)phenoxy)methyl)quinazolin-4(3H)-one A mixture of Intermediate 1,4-(1-methyl-4-(pyridin-4-yl)-1H-pyrazol-3-yl)phenol (113 mg, 0.450 mmol) and cesium carbonate (390 mg, 1.197 mmol) in DMF (2 mL) was stirred at ambient temperature for 15 minutes. A solution of 2-(chloromethyl)-3-methylquinazolin-4(3H)-one (CAS#199114-62-0, Enamine #EN300-23745, 100 mg, 0.479 mmol) in DMF/THF (1 mL:1 mL) was added dropwise to the stirred reaction mixture. When the addition was complete, the reaction mixture was stirred at ambient temperature for 20 hours. An aliquot was partitioned between water and EtOAc and the organic layer was checked by TLC (98:2 DCM/2M $NH_3$ in MeOH). The spot for the starting phenol was replaced by a higher Rf spot, so the reaction mixture was diluted with water (100 mL) and extracted with EtOAc (2×25 mL). The combined organic extracts were washed with brine (2×50 mL), then dried ($MgSO_4$) and filtered. The filtrate was concentrated under reduced pressure to give an off-white solid that was purified by column chromatography on an Analogix IF-280 (Agilent SF15-24 g, 100% EtOAc to 98:2 EtOAc/MeOH). Fractions #6-28 were combined and concentrated under reduced pressure to give 3-methyl-2-((4-(1-methyl-4-(pyridin-4-yl)-1H-pyrazol-3-yl)phenoxy)methyl)quinazolin-4(3H)-one as a white solid (160.6 mg, 84.3%). $^1$H NMR (300 MHz, methanol-$d_4$) δ 8.34 (dd, J=5.0, 1.2, 2H), 8.26-8.21 (m, 1H), 8.00 (s, 1H), 7.87-7.80 (m, 1H), 7.75-7.70 (m, 1H), 7.60-7.54 (m, 1H), 7.42-7.35 (m, 2H), 7.27 (dd, J=4.9, 1.4, 2H), 7.19-7.13 (m, 2H), 5.31 (s, 2H), 3.96 (s, 3H), 3.74 (s, 3H). MS (DCI—$NH_3$) m/z=424 (M+H)$^+$.

Example 5

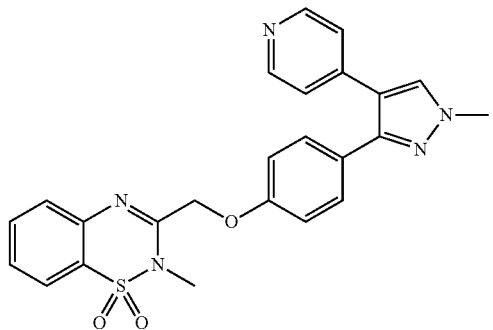 [SMILES: CN1C(COc2ccc(-c3nn(C)cc3-c3ccncc3)cc2)=Nc2ccccc2S1(=O)=O]

1,1-dioxo-2-methyl-3-((4-(1-methyl-4-(pyridin-4-yl)-1H-pyrazol-3-yl)phenoxy)methyl)-2H-benzo[e][1,2,4]thiadiazine The title compound is prepared by the method of Example 1, substituting Intermediate 12A, 1,1-dioxo-3-(chloromethyl)-2-methyl-2H-benzo[e][1,2,4]thiadiazine, in place of Intermediate 5A, 2-(chloromethyl)-1,5-naphthyridine.

Example 6

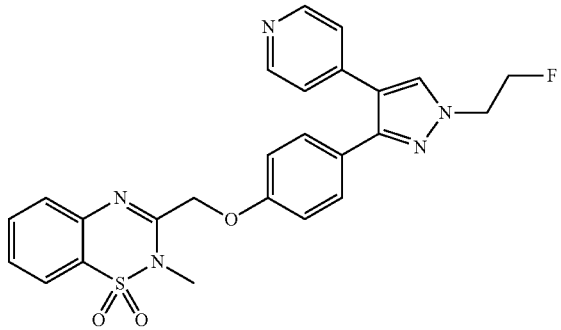 [SMILES: CN1C(COc2ccc(-c3nn(CCF)cc3-c3ccncc3)cc2)=Nc2ccccc2S1(=O)=O]

1,1-dioxo-3-((4-(1-(2-fluoroethyl)-4-(pyridin-4-yl)-1H-pyrazol-3-yl)phenoxy)methyl)-2-methyl-2H-benzo[e][1,2,4]thiadiazine The title compound is prepared by the method of Example 2, substituting Intermediate 12A, 1,1-dioxo-3-(chloromethyl)-2-methyl-2H-benzo[e][1,2,4]thiadiazine, in place of Intermediate 5A, 2-(chloromethyl)-1,5-naphthyridine.

67

Example 7

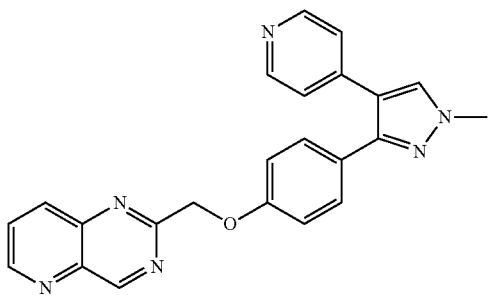

2-((4-(1-methyl-4-(pyridin-4-yl)-1H-pyrazol-3-yl)phenoxy)methyl)pyrido[3,2-d]pyrimidine The title compound is prepared by the method of Example 1, substituting Intermediate 14A, 2-(chloromethyl)pyrido[3,2-d]pyrimidine, in place of Intermediate 5A, 2-(chloromethyl)-1,5-naphthyridine.

Example 8

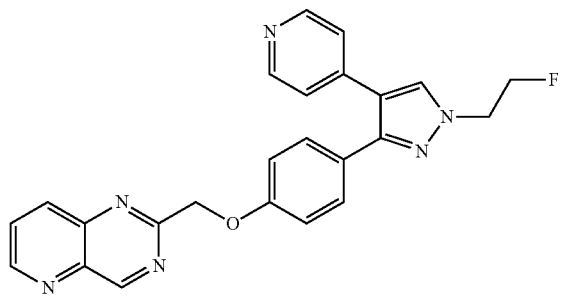

2-((4-(1-(2-fluoroethyl)-4-(pyridin-4-yl)-1H-pyrazol-3-yl)phenoxy)methyl)pyrido[3,2-d]pyrimidine The title compound is prepared by the method of Example 2, substituting Intermediate 14A, 2-(chloromethyl)pyrido[3,2-d]pyrimidine, in place of Intermediate 5A, 2-(chloromethyl)-1,5-naphthyridine.

Example 9

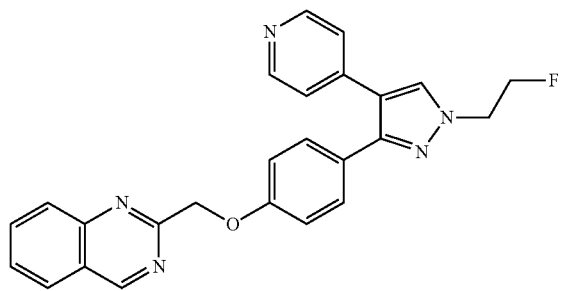 [SMILES: FCCn1cc(-c2ccncc2)c(-c2ccc(OCc3ncc4ccccc4n3)cc2)n1]

68

2-((4-(1-(2-fluoroethyl)-4-(pyridin-4-yl)-1H-pyrazol-3-yl)phenoxy)methyl)quinazoline A mixture of Intermediate 3,4-(1-(2-fluoroethyl)-4-(pyridin-4-yl)-1H-pyrazol-3-yl)phenol, (89 mg, 0.314 mmol) and cesium carbonate (307 mg, 0.942 mmol) in DMF (3 mL) was stirred at ambient temperature for 10 minutes under a dry nitrogen atmosphere. A solution of Intermediate 15A, 2-(chloromethyl)quinazoline, (67.3 mg, 0.377 mmol) in THF (1 mL) was added dropwise to the stirred reaction mixture. After the addition was complete, the reaction mixture was stirred at ambient temperature for 3.5 hours under a dry nitrogen atmosphere. An aliquot was partitioned between water and EtOAc. The organic layer was checked by TLC (95:5 DCM/2M $NH_3$ in MeOH). The spot for the starting phenol was replaced by a major higher Rf spot and a few very minor spots, so the reaction mixture was partitioned between EtOAc and water. The organic layer was washed twice with brine, then dried ($MgSO_4$), and filtered. The filtrate was concentrated under reduced pressure and the residue was purified by column chromatography on an Analogix IF-280 (Varian SF25-80, 100% DCM to 97:3 DCM/2M $NH_3$ in MeOH). Fractions containing product and no yellow color (#11-32) were combined and concentrated under reduced pressure. The residue was dissolved in DCM and filtered. The filtrate was concentrated under reduced pressure to give a pale beige amorphous solid (70.2 mg, 52.5%). Fractions containing product and yellow color (#33-42) were combined and concentrated under reduced pressure separately. The residue was dissolved in DCM and filtered. This filtrate was concentrated under reduced pressure to give a pale yellow amorphous solid, which appeared to be identical (by NMR & MS) to the first batch. Both batches were combined to give 2-((4-(1-(2-fluoroethyl)-4-(pyridin-4-yl)-1H-pyrazol-3-yl)phenoxy)methyl)quinazoline (115 mg, 86%). $^1$H NMR (300 MHz, methanol-$d_4$) δ 9.57 (s, 1H), 8.35 (dd, J=4.6, 1.6 Hz, 2H), 8.15 (dt, J=8.1, 1.0 Hz, 1H), 8.08 (s, 1H), 8.07-8.01 (m, 2H), 7.83-7.73 (m, 1H), 7.40-7.33 (m, 2H), 7.29 (dd, J=4.7, 1.7 Hz, 2H), 7.15-7.09 (m, 2H), 5.48 (s, 2H), 4.81 (dt, J=47.2, 4.7 Hz, 2H), 4.50 (dt, J=26.6, 4.7 Hz, 2H). MS (+ESI) m/z=426 (M+H)$^+$.

Example 10

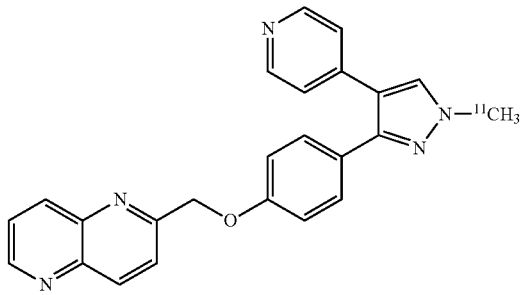 [SMILES: [11CH3]n1cc(-c2ccncc2)c(-c2ccc(OCc3ccc4ncccc4n3)cc2)n1]

2-((4-(1-methyl-4-(pyridin-4-yl)-1H-pyrazol-3-yl)phenoxy)methyl)-1,5-naphthyridine

Example 10A $^{11}CH_3I$

[$^{11}$C]methyl iodide

[$^{11}$C]carbon dioxide is produced by the [$^{14}$N(p,α)$^{11}$C] nuclear reaction using a nitrogen gas target (containing oxygen) and bombarding with protons from a cyclotron. Subsequently, [$^{11}$C]CO$_2$ is converted by catalytic reduction (Ni), to [$^{11}$C]methane. [$^{11}$C]Methane is then converted into [$^{11}$C]methyl iodide by gas phase iodination with iodine.

Example 10

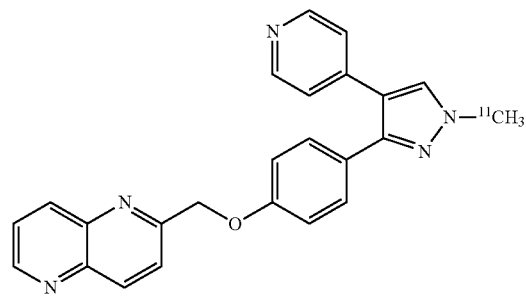 [SMILES: [11CH3]n1cc(-c2ccncc2)c(-c2ccc(OCc3ccc4ncccc4n3)cc2)n1]

2-((4-(1-[$^{11}$C]methyl-4-(pyridin-4-yl)-1H-pyrazol-3-yl)phenoxy)methyl)-1,5-naphthyridine To a solution of the labeling precursor, Intermediate 4, 2-((4-(4-(pyridin-4-yl)-1H-pyrazol-3-yl)phenoxy)methyl)-1,5-naphthyridine (0.5-0.6 mg) in 100 μL of anhydrous N,N-dimethylformamide (DMF) is added tetrabutylammonium hydroxide solution (0.9-1.0 μL of 1M TBAOH in methanol). The solution is vortexed for 1 minute then reacted with Example 10A, [$^{11}$C]methyl iodide at ambient temperature for 5 minutes. The reaction mixture is then loaded onto a semipreparative column and eluted with 0.1 M ammonium formate (no pH adjust)/acetonitrile (55:45) at 5 mL/min. The product peak is collected, diluted with deionized water (50 mL) and loaded onto a conditioned Classic C-18 SepPak. The SepPak is washed with deionized water (10 mL), and the product is eluted with EtOH (1 mL) followed by saline (3 mL), through a 33-mm 0.22-μm Millipore GV filter, into a dose vial containing 7 mL saline and 40 μL of 4.2% NaHCO$_3$.

Example 11

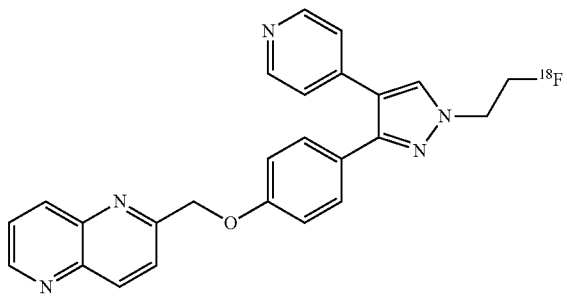 [SMILES: [18F]CCn1cc(-c2ccncc2)c(-c2ccc(OCc3ccc4ncccc4n3)cc2)n1]

2-((4-(1-(2-[$^{18}$F]-fluoroethyl)-4-(pyridin-4-yl)-1H-pyrazol-3-yl)phenoxy)methyl)-1,5-naphthyridine Example 11A K[$^{18}$F]F-kryptofix 222 complex

[$^{18}$F]Fluoride is produced by an [$^{18}$O(p,n)$^{18}$F]reaction by irradiation of enriched [$^{18}$F]H$_2$O in a niobium target using protons from a cyclotron. After irradiation, the resultant [$^{18}$F] F— is separated from [$^{18}$O]H$_2$O using a SepPak anion exchange cartridge. [$^{18}$F]F— is eluted from the cartridge using a mixture of MeCN (0.3 mL) and Kryptofix 222/K$_2$CO$_3$ solution (0.45 mL). The solution is evaporated under a stream of helium at 110° C. by applying conventional heating and further dried by azeotropic distillation using MeCN at a temperature of 110° C.

Example 11

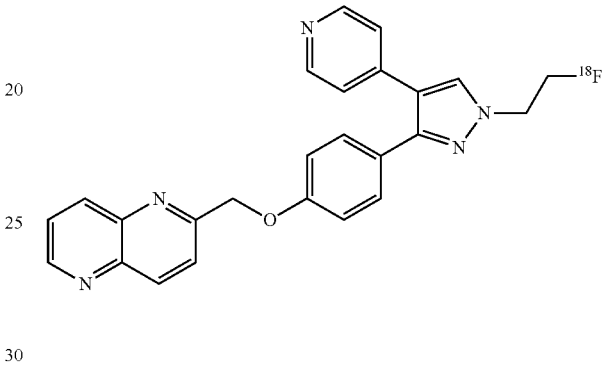

2-((4-(1-(2-[$^{18}$F]-fluoroethyl)-4-(pyridin-4-yl)-1H-pyrazol-3-yl)phenoxy)methyl)-1,5-naphthyridine Method 1: The labeling precursor, Intermediate 5,2-(3-(4-((1,5-naphthyridin-2-yl)methoxy)phenyl)-4-(pyridin-4-yl)-1H-pyrazol-1-yl)ethyl methanesulfonate (5 mg, 10 μmol) in DCM (1 mL) is dissolved in anhydrous DMF (1.5 mL) and used (0.3 mL) for direct nucleophilic radiofluorination. The O-mesyl derivative is added to Example 11A, the dried [$^{18}$F] F—/K$_2$CO$_3$/Kryptofix 222 complex, produced as described above. The nucleophilic substitution reaction is carried out by conventional heating at 90° C. for 15 min. Next, the crude mixture is diluted with water (1.4 mL) and injected onto an HPLC system consisting of a semipreparative C18 column that is eluted with a mixture of 0.05M NaOAc buffer pH 5.5 and EtOH. UV detection of the HPLC eluate was performed at 254 nm. The peak containing the radiolabeled product, Example 11, is collected then diluted with saline to obtain a final EtOH concentration of <10%, and the solution is sterile filtered through a 0.22 μm membrane filter. The purity of the radiotracer is analyzed using an analytical HPLC system consisting of a C18 column eluted with a mixture of 0.05 M NaOAc buffer pH 5.5 and MeCN. UV detection of the HPLC eluate is performed at 254 nm.

Method 2: The title compound is prepared similar to Method 1 above, substituting Intermediate 8, 2-(3-(4-((1,5-naphthyridin-2-yl)methoxy)phenyl)-4-(pyridin-4-yl)-1H-pyrazol-1-yl)ethyl 4-methylbenzenesulfonate, in place of Intermediate 5, 2-(3-(4-((1,5-naphthyridin-2-yl)methoxy) phenyl)-4-(pyridin-4-yl)-1H-pyrazol-1-yl)ethyl methanesulfonate.

Example 12

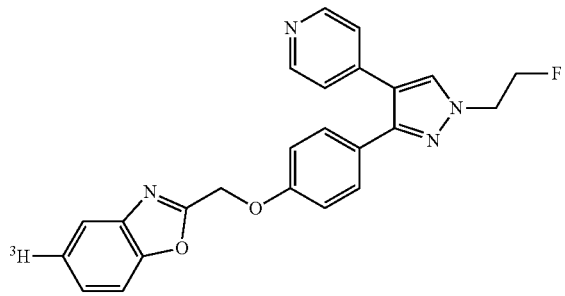 [SMILES: [3H]c1ccc2oc(COc3ccc(-c4nn(CCF)cc4-c4ccncc4)cc3)nc2c1]

2-((4-(1-(2-fluoroethyl)-4-(pyridin-4-yl)-1H-pyrazol-3-yl)phenoxy)methyl)-5-[$^3$H]benzo[d]oxazole The catalyst (10% Pd/C) was weighed into a 5 mL tritium flask. Intermediate 7, 5-bromo-2-((4-(1-(2-fluoroethyl)-4-(pyridin-4-yl)-1H-pyrazol-3-yl)phenoxy)methyl)benzo[d]oxazole, was dissolved in N,N-dimethylacetamide (0.5 mL), then Et$_3$N was added and this solution was transferred to the reaction flask. The flask was attached to the Trisorber, cooled in liquid nitrogen and evacuated. The tritium gas was generated and admitted to the reaction flask. The reaction mixture was stirred for 50 min, then the volatiles were absorbed on the liquid nitrogen-cooled charcoal trap. The reaction mixture was diluted with methanol (~2 mL) and filtered. The methanol was distilled out in vacuo. This process was repeated three times then the liquid residue taken up in methanol (29.3 mCi). RHPLC analysis [from 0.1% TFA: CH$_3$CN (70:30) to 50% CH$_3$CN in 20 min to 100% CH$_3$CN in 22 min hold to 30 min on Phenomenex Luna C18(2), 4.6×250 mm, 1 mL/min, 320 nM UV] showed ~71% desired product at ~10.3 min (there was an apparent by-product at 9.5 min, ~23%). There was <1% unreacted brominated precursor. Coinjection of this crude product solution with the unlabeled standard, lot 1816476-0, showed that it coinjected with the standard at ~10.3 min and that >91% was the desired product (the by-product was apparently a chromatographic anomaly). The product solution was taken to dryness on the vacuum line and the residue taken up in methanol (~0.25 mL). RHPLC (same as before, except no change to 100% CH$_3$CN) showed >94% product (27.4 mCi). RTLC analysis [DCM:MeOH:conc. NH$_4$OH (19:1:0.1) on silica gel] showed >97% product. The product solution was purified by preparative TLC [one 20×20 cm, 250 micron EM silica gel "G" eluted with DCM:MeOH: con NH$_4$OH (190:10:1), product elution with ether] to give a product solution which was taken to dryness in vacuo. The residue was taken up in ethanol (10.0 mL, 16.3 mCi, 1.63 mCi/mL). RHPLC showed >99% radiochemical purity (RT ~10.3 min, two replicates). LC/MS (same as second column except using 0.1% HOFor) confirmed identity as 2-((4-(1-(2-fluoroethyl)-4-(pyridin-4-yl)-1H-pyrazol-3-yl)phenoxy)methyl)-5-[$^3$H]benzo[d]oxazole. MS m/z=417 (M+H)$^+$. Specific activity=20.5 Ci/mmol.

Example 13

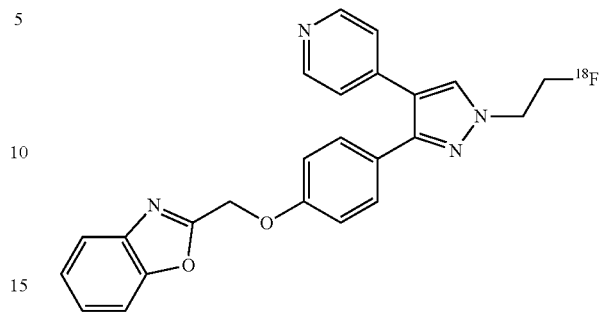

2-((4-(1-(2-[$^{18}$F]fluoroethyl)-4-(pyridin-4-yl)-1H-pyrazol-3-yl)phenoxy)methyl)benzo[d]oxazole Method 1: The title compound is prepared by the method of Example 11, substituting Intermediate 6,2-(3-(4-(benzo[d]oxazol-2-ylmethoxy)phenyl)-4-(pyridin-4-yl)-1H-pyrazol-1-yl)ethyl methanesulfonate, in place of Intermediate 5,2-(3-(4-((1,5-naphthyridin-2-yl)methoxy)phenyl)-4-(pyridin-4-yl)-1H-pyrazol-1-yl)ethyl methanesulfonate.

Method 2: The title compound is prepared similar to Method 1 above, substituting Intermediate 9,2-(3-(4-(benzo[d]oxazol-2-ylmethoxy)phenyl)-4-(pyridin-4-yl)-1H-pyrazol-1-yl)ethyl 4-methylbenzenesulfonate, in place of Intermediate 6,2-(3-(4-(benzo[d]oxazol-2-ylmethoxy)phenyl)-4-(pyridin-4-yl)-1H-pyrazol-1-yl)ethyl methanesulfonate.

Example 14

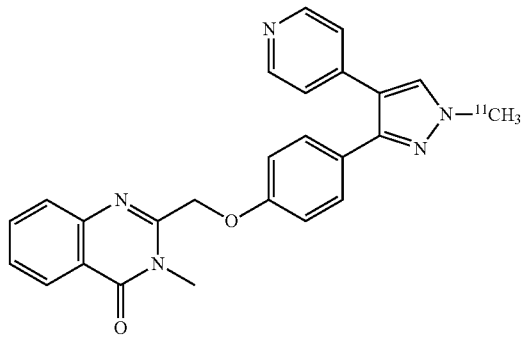 [SMILES: Cn1c(COc2ccc(-c3nn([11CH3])cc3-c3ccncc3)cc2)nc2ccccc2c1=O]

3-methyl-2-((4-(1-[$^{11}$C]methyl-4-(pyridin-4-yl)-1H-pyrazol-3-yl)phenoxy)methyl)quinazolin-4(3H)-one The title compound is prepared by the method of Example 10, substituting Intermediate 10, 3-methyl-2-((4-(4-(pyridin-4-yl)-1H-pyrazol-3-yl)phenoxy)methyl)quinazolin-4(3H)-one, in place of Intermediate 4, 2-((4-(4-(pyridin-4-yl)-1H-pyrazol-3-yl)phenoxy)methyl)-1,5-naphthyridine.

Example 15

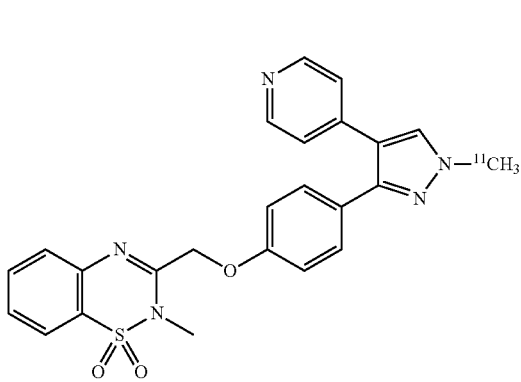 [SMILES: CN1C(COc2ccc(-c3nn([11CH3])cc3-c3ccncc3)cc2)=Nc2ccccc2S1(=O)=O]

1,1-dioxo-2-methyl-3-((4-(1-[$^{11}$C]methyl-4-(pyridin-4-yl)-1H-pyrazol-3-yl)phenoxy)methyl)-2H-benzo[e][1,2,4]thiadiazine The title compound is prepared by the method of Example 10, substituting Intermediate 11, 1,1-dioxo-2-methyl-3-((4-(4-(pyridin-4-yl)-1H-pyrazol-3-yl)phenoxy)methyl)-2H-benzo[e][1,2,4]thiadiazine, in place of Intermediate 4, 2-((4-(4-(pyridin-4-yl)-1H-pyrazol-3-yl)phenoxy)methyl)-1,5-naphthyridine.

Example 16

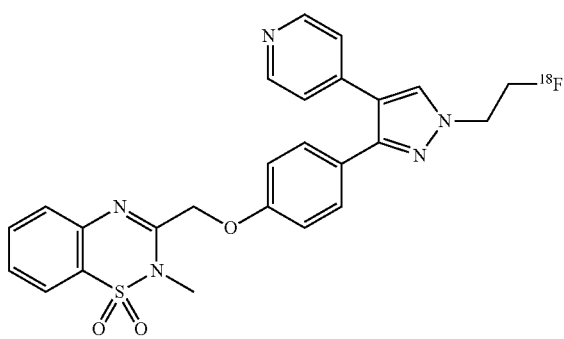 [SMILES: CN1C(COc2ccc(-c3nn(CC[18F])cc3-c3ccncc3)cc2)=Nc2ccccc2S1(=O)=O]

1,1-dioxo-3-((4-(1-(2-[$^{18}$F]fluoroethyl)-4-(pyridin-4-yl)-1H-pyrazol-3-yl)phenoxy)methyl)-2-methyl-2H-benzo[e][1,2,4]thiadiazine The title compound is prepared by method 2 of Example 11, substituting Intermediate 12, 2-(3-(4-((1,1-dioxo-2-methyl-2H-benzo[e][1,2,4]thiadiazin-3-yl)methoxy)phenyl)-4-(pyridin-4-yl)-1H-pyrazol-1-yl)ethyl 4-methylbenzenesulfonate, in place of Intermediate 8, 2-(3-(4-(((1,5-naphthyridin-2-yl)methoxy)phenyl)-4-(pyridin-4-yl)-1H-pyrazol-1-yl)ethyl 4-methylbenzenesulfonate.

Example 17

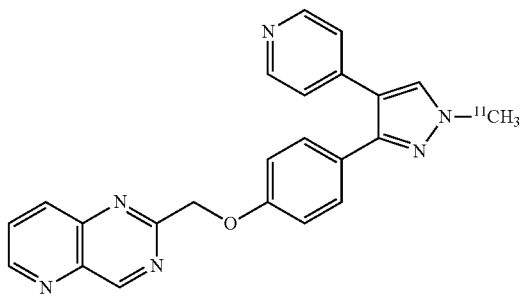 [SMILES: [11CH3]n1cc(-c2ccncc2)c(-c2ccc(OCc3ncc4ncccc4n3)cc2)n1]

2-((4-(1-[$^{11}$C]methyl-4-(pyridin-4-yl)-1H-pyrazol-3-yl)phenoxy)methyl)pyrido[3,2-d]pyrimidine The title compound is prepared by the method of Example 10, substituting Intermediate 13, 2-((4-(4-(pyridin-4-yl)-1H-pyrazol-3-yl)phenoxy)methyl)pyrido[3,2-d]pyrimidine, in place of Intermediate 4, 2-((4-(4-(pyridin-4-yl)-1H-pyrazol-3-yl)phenoxy)methyl)-1,5-naphthyridine.

Example 18

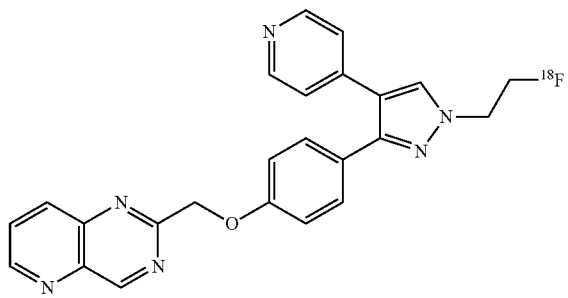 [SMILES: [18F]CCn1cc(-c2ccncc2)c(-c2ccc(OCc3ncc4ncccc4n3)cc2)n1]

2-((4-(1-(2-[$^{18}$F]-fluoroethyl)-4-(pyridin-4-yl)-1H-pyrazol-3-yl)phenoxy)methyl)pyrido[3,2-d]pyrimidine The title compound is prepared by method 2 of Example 11, substituting Intermediate 14, 2-(4-(pyridin-4-yl)-3-(4-(pyrido[3,2-d]pyrimidin-2-ylmethoxy)phenyl)-1H-pyrazol-1-yl)ethyl 4-methylbenzenesulfonate, in place of Intermediate 8, 2-(3-(4-(((1,5-naphthyridin-2-yl)methoxy)phenyl)-4-(pyridin-4-yl)-1H-pyrazol-1-yl)ethyl 4-methylbenzenesulfonate.

Example 19

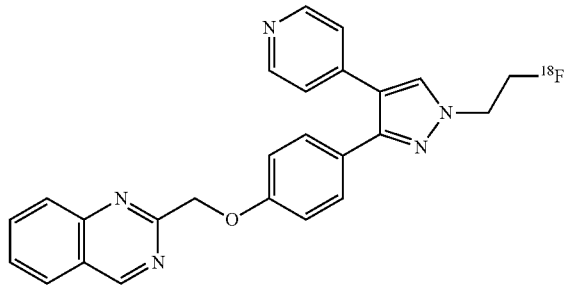 [SMILES: [18F]CCn1cc(-c2ccncc2)c(-c2ccc(OCc3ncc4ccccc4n3)cc2)n1]

2-((4-(1-(2-[$^{18}$F]-fluoroethyl)-4-(pyridin-4-yl)-1H-pyrazol-3-yl)phenoxy)methyl)quinazoline The title compound is prepared by method 2 of Example 11, substituting Intermediate 15, 2-(4-(pyridin-4-yl)-3-(4-(quinazolin-2-ylmethoxy)phenyl)-1H-pyrazol-1-yl)ethyl 4-methylbenzenesulfonate, in place of Intermediate 8, 2-(3-(4-((1,5-naphthyridin-2-yl)methoxy)phenyl)-4-(pyridin-4-yl)-1H-pyrazol-1-yl)ethyl 4-methylbenzenesulfonate.

Determination of Biological Activity

To determine the effectiveness of representative compounds of this invention as PDE10A ligands, the following tests were conducted.

Recombinant PDE proteins were used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH7.5, 10 mM MgCl$_2$, 0.1% bovine serum albumin) containing enzyme and substrate. The PDE enzymes concentration ranged from 10 pM-250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29° C. The reaction was stopped by addition of lysis buffer from assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, IC$_{50}$ value of inhibitor can be obtained by plotting inhibitor concentration against PDE activity at that concentration.

Compounds of the invention are PDE10A ligands that modulate function of PDE10A. Generally, representative compounds of the invention demonstrated binding affinities for the PDE10A of K$_i$<50 nM or <20 nM and frequently <1 nM. For example, Table 1 shows that compounds of Examples 1-4 and 9, which are representative of compounds of the invention, demonstrated PDE10 IC$_{50}$ binding affinities of 1.05 nM, 0.2 nM, 4.70 nM, 2.00 nM, and 0.18 nM, respectively.

Table 1 demonstrates additional characteristics of representative compounds of the invention as compared to three known PDE10A ligands, MP-10, JNJ-41510417, and Janssen B-3 (Tu et al., Bioorg. Med. Chem. 19, 2011, 1666-1673; Celen et al., J. Nucl. Med. 51(10), 2010, 1584-1591; WO 2011/051324.) As shown, compounds of the invention unexpectedly possess superior lipophilic and brain-penetrant properties, and hepatocyte half-lives as compared to the known compounds. Compounds of the invention, particularly the compounds of Examples 1-4 and 9, are less lipophilic than MP-10, JNJ-41510417 and Janssen B-3, as demonstrated by shake flask (SF) log D values. Preferred compounds of the invention have shake flask log D values of less than 4. Compounds of the invention, particularly the compounds of Examples 1-4, are poorer substrates for P-gp, and thus are more brain-penetrant than the two known compounds MP-10 and JNJ-41510417, as demonstrated by their lower Efflux Ratio in the MDCK-MDR1 assay. Preferred compounds of the invention have Efflux Ratios of less than 2.3. Compounds of the invention, particularly the compounds of Examples 1, 2 and 4, have significantly longer human hepatocyte half-lives than MP-10, JNJ-41510417 and Janssen B-3, as demonstrated by human Hepatocyte T$_{1/2}$ values. Longer hepatocyte half-lives may provide advantages in that formation of brain-penetrant, radiolabeled, phenolic metabolites may be slowed.

Accordingly, compounds of the invention are useful as PDE10A PET ligands.

TABLE 1

| Compound | PDE10 IC$_{50}$ (nM) | Rat PK (0.05 mg/kg, iv) | | | MDCK-MDR1 Efflux Ratio (P-gp) | SF log D | Hepatocyte T$_{1/2}$ (min) | Monkey Microsome T$_{1/2}$ (min) |
|---|---|---|---|---|---|---|---|---|
| | | Min. after dose | Free [brain] (ng/g) | Free B/P | | | | |
| 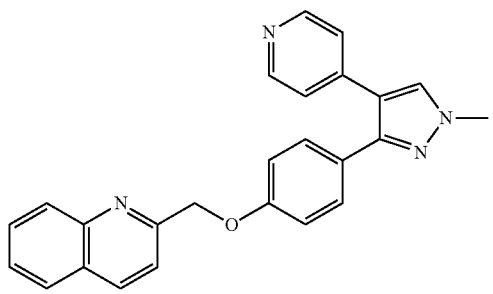 [SMILES: Cn1cc(-c2ccncc2)c(-c2ccc(OCc3ccc4ccccc4n3)cc2)n1] MP-10 | 1.68 | 3<br>5 | 0.054<br>0.098 | 0.32<br>0.22 | 2.51 | 4.28 | R 13.0<br>H 54.9 | 7.0 |

TABLE 1-continued

| Compound | PDE10 IC$_{50}$ (nM) | Rat PK (0.05 mg/kg, iv) | | | MDCK-MDR1 Efflux Ratio (P-gp) | SF log D | Hepatocyte T$_{1/2}$ (min) | Monkey Microsome T$_{1/2}$ (min) |
|---|---|---|---|---|---|---|---|---|
| | | Min. after dose | Free [brain] (ng/g) | Free B/P | | | | |
| JNJ-41510417 | 0.63 | 3<br>5 | 0.168<br>0.034 | 0.40<br>0.19 | 3.92 | 4.47 | R 15.3<br>H 41.7 | 28.0 |
| Janssen B-3 | 0.98 | 3<br>5 | 0.323<br>0.167 | 0.18<br>0.26 | 2.20 | 4.05 | R 9.1<br>H 19.0 | 3.1 |
| Example 1 | 1.05 | 3<br>5 | 0.712<br>0.732 | 0.43<br>0.54 | 0.73 | 3.68 | R 18.7<br>H 215.0 | 27.0 |
| Example 2 | 0.20 | 3<br>5 | 0.692<br>0.184 | 0.20<br>0.13 | 1.95 | 3.71 | R 12.0<br>H 79.0 | 24.0 |

TABLE 1-continued

| Compound | PDE10 IC$_{50}$ (nM) | Rat PK (0.05 mg/kg, iv) | | | MDCK-MDR1 Efflux Ratio (P-gp) | SF log D | Hepatocyte T$_{1/2}$ (min) | Monkey Microsome T$_{1/2}$ (min) |
|---|---|---|---|---|---|---|---|---|
| | | Min. after dose | Free [brain] (ng/g) | Free B/P | | | | |
| Example 3 | 4.70 | 3<br>5 | 0.296<br>0.155 | 0.55<br>0.43 | 2.12 | 3.92 | R 17.6<br>H 50.6 | 23.0 |
| Example 4 | 2.00 | 3<br>5 | 0.213<br>0.166 | 0.14<br>0.15 | 1.52 | 3.49 | R 17.2<br>H 88.5 | 54.0 |
| Example 9 | 0.18 | 3<br>5 | | | 4.84 | 3.50 | R 13.0<br>H 53.0 | |

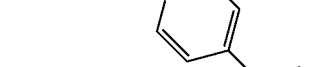

Free B/P = Ratio of free brain concentration divided by free plasma concentration;
SF log D = log D determined by shake flask method;
R = rat;
H = human It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, formulations, or methods of use of the invention, may be made without departing from the spirit and scope thereof.

What is claimed is:

1. A radiolabeled compound of formula (I),

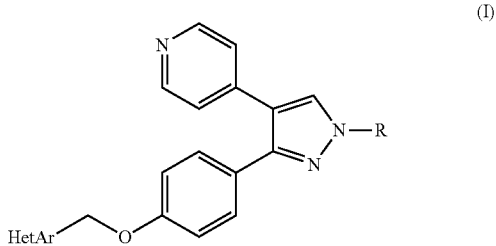
(I)

or a pharmaceutically acceptable salt thereof, wherein
R is selected from the group consisting of hydrogen, $C_1$-$C_6$ alkyl, and $C_3$-$C_8$ cycloalkyl;
HetAr is a heteroaryl group selected from the group consisting of

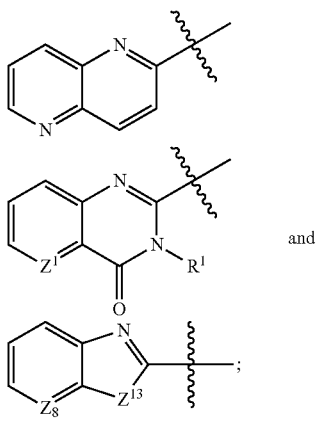

$Z^1$ and $Z^8$ are each $CR^2$;
$Z^{13}$ is O; and
$R^1$ and $R^2$ are each independently selected from the group consisting of hydrogen, halogen, $C_1$-$C_6$ alkyl, and $C_3$-$C_8$ cycloalkyl;
wherein each of the carbon atoms of each alkyl group is substituted with hydrogen or with 0, 1, or 2 substituents selected from acyl, acyloxy, alkoxy, alkoxyalkoxy, alkoxyalkyl, alkoxycarbonyl, alkoxyimino, alkoxysulfonyl, alkylcarbonyl, alkylsulfonyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —$NR_AR_B$, ($NR_AR_B$)carbonyl, ($NR_AR_B$)sulfonyl, —$OS(O)_2$-alkyl, and —$OS(O)_2$—aryl; wherein $R_A$ and $R_B$ are independently selected from hydrogen, alkyl, acyl, cycloalkyl, and formyl;

wherein each of the carbon atoms of each cycloalkyl group is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_AR_B$, ($NR_AR_B$)carbonyl, —$SO_2N(R_{14a})(R_{14b})$, and $N(R_{14a})SO_2(R_{14b})$; wherein $R_A$ and $R_B$ are independently selected from hydrogen, alkyl, acyl, cycloalkyl, and formyl; and wherein $R_{14a}$ and $R_{14b}$ are each independently hydrogen, alkyl, or cycloalkyl.

2. The compound of claim 1, wherein R comprises a radiolabel.

3. The compound of claim 1, wherein HetAr comprises a radiolabel.

4. The compound of claim 1, wherein HetAr is

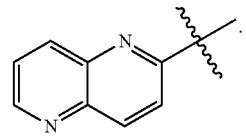 [SMILES: *c1ccc2ncccc2n1]

5. The compound of claim 4, wherein R is $C_1$-$C_6$ alkyl.

6. The compound of claim 5, selected from the group consisting of:

2-((4-(1-[$^{11}$C]methyl-4-(pyridin-4-yl)-1H-pyrazol-3-yl)phenoxy)methyl)-1,5-naphthyridine; and 2-((4-(1-(2-[$^{18}$F]fluoroethyl)-4-(pyridin-4-yl)-1H-pyrazol-3-yl)phenoxy)methyl)-1,5-naphthyridine.

7. The compound of claim 1, wherein HetAr is

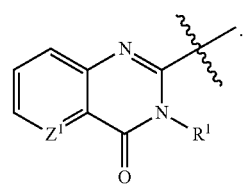

8. The compound of claim 7, wherein
$Z^1$ is CH;
$R^1$ is $C_1$-$C_6$ alkyl; and
R is $C_1$-$C_6$ alkyl.

9. The compound of claim 7, selected from the group consisting of:

3-methyl-2-((4-(1-[$^{11}$C]methyl-4-(pyridin-4-yl)-1H-pyrazol-3-yl)phenoxy)methyl)quinazolin-4(3H)-one;

2-((4-(1-(2-[$^{18}$F]fluoroethyl)-4-(pyridin-4-yl)-1H-pyrazol-3-yl)phenoxy)methyl)-3-methylquinazolin-4(3H)-one;

3-[$^{11}$C]methyl-2-((4-(1-methyl-4-(pyridin-4-yl)-1H-pyrazol-3-yl)phenoxy)methyl)quinazolin-4(3H)-one; and 3-(2-[$^{18}$F]fluoroethyl)-2-((4-(1-methyl-4-(pyridin-4-yl)-1H-pyrazol-3-yl)phenoxy)methyl)quinazolin-4(3H)-one.

10. The compound of claim 1, wherein HetAr is

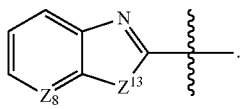

11. The compound of claim 10, wherein
Z$^8$ is CH;
and
R is $C_1$-$C_6$ alkyl.

12. The compound of claim 10, selected from the group consisting of:
2-((4-(1-[$^{11}$C]methyl-4-(pyridin-4-yl)-1H-pyrazol-3-yl)phenoxy)methyl)benzo[d]oxazole; and
2-((4-(1-(2-[$^{18}$F]fluoroethyl)-4-(pyridin-4-yl)-1H-pyrazol-3-yl)phenoxy)methyl)benzo[d]oxazole.

13. A pharmaceutical composition comprising a therapeutically effective amount of a compound of formula (I) according to claim 1, or a pharmaceutically acceptable salt thereof, in combination with a pharmaceutically acceptable carrier.

14. A method for imaging PDE10A in a mammal comprising administering to a subject an effective amount of a compound of claim 1, or a pharmaceutically acceptable salt thereof.

15. The method of claim 14, wherein the compound is selected from the group consisting of:
2-((4-(1-[$^{11}$C]methyl-4-(pyridin-4-yl)-1H-pyrazol-3-yl)phenoxy)methyl)-1,5-naphthyridine;
2-((4-(1-(2-[$^{18}$F]fluoroethyl)-4-(pyridin-4-yl)-1H-pyrazol-3-yl)phenoxy)methyl)-1,5-naphthyridine;
3-methyl-2-((4-(1-[$^{11}$C]methyl-4-(pyridin-4-yl)-1H-pyrazol-3-yl)phenoxy)methyl)quinazolin-4(3H)-one;
2-((4-(1-(2-[$^{18}$F]fluoroethyl)-4-(pyridin-4-yl)-1H-pyrazol-3-yl)phenoxy)methyl)-3-methylquinazolin-4(3H)-one;
3-[$^{11}$C]methyl-2-((4-(1-methyl-4-(pyridin-4-yl)-1H-pyrazol-3-yl)phenoxy)methyl)quinazolin-4(3H)-one;
3-(2-[$^{18}$F]fluoroethyl)-2-((4-(1-methyl-4-(pyridin-4-yl)-1H-pyrazol-3-yl)phenoxy)methyl)quinazolin-4(3H)-one;
2-((4-(1-[$^{11}$C]methyl-4-(pyridin-4-yl)-1H-pyrazol-3-yl)phenoxy)methyl)benzo[d]oxazole; and
2-((4-(1-(2-[$^{18}$F]fluoroethyl)-4-(pyridin-4-yl)-1H-pyrazol-3-yl)phenoxy)methyl)benzo[d]oxazole.

16. The method of claim 15, wherein the compound is selected from the group consisting of:
2-((4-(1-[$^{11}$C]methyl-4-(pyridin-4-yl)-1H-pyrazol-3-yl)phenoxy)methyl)-1,5-naphthyridine;
2-((4-(1-(2-[$^{18}$F]fluoroethyl)-4-(pyridin-4-yl)-1H-pyrazol-3-yl)phenoxy)methyl)-1,5-naphthyridine; and
2-((4-(1-(2-[$^{18}$F]fluoroethyl)-4-(pyridin-4-yl)-1H-pyrazol-3-yl)phenoxy)methyl)benzo[d]oxazole.

17. A compound or a pharmaceutically acceptable salt thereof, wherein the compound is selected from the group consisting of:
2-((4-(1-[$^{11}$C]methyl-4-(pyridin-4-yl)-1H-pyrazol-3-yl)phenoxy)methyl)-1,5-naphthyridine;
2-((4-(1-(2-[$^{18}$F]fluoroethyl)-4-(pyridin-4-yl)-1H-pyrazol-3-yl)phenoxy)methyl)-1,5-naphthyridine;
3-methyl-2-((4-(1-[$^{11}$C]methyl-4-(pyridin-4-yl)-1H-pyrazol-3-yl)phenoxy)methyl)quinazolin-4(3H)-one;
2-((4-(1-(2-[$^{18}$F]fluoroethyl)-4-(pyridin-4-yl)-1H-pyrazol-3-yl)phenoxy)methyl)-3-methylquinazolin-4(3H)-one;
3-[$^{11}$C]methyl-2-((4-(1-methyl-4-(pyridin-4-yl)-1H-pyrazol-3-yl)phenoxy)methyl)quinazolin-4(3H)-one;
3-(2-[$^{18}$F]fluoroethyl)-2-((4-(1-methyl-4-(pyridin-4-yl)-1H-pyrazol-3-yl)phenoxy)methyl)quinazolin-4(3H)-one;
2-((4-(1-[$^{11}$C]methyl-4-(pyridin-4-yl)-1H-pyrazol-3-yl)phenoxy)methyl)benzo[d]oxazole; and
2-((4-(1-(2-[$^{18}$F]fluoroethyl)-4-(pyridin-4-yl)-1H-pyrazol-3-yl)phenoxy)methyl)benzo[d]oxazole.

* * * * *